(12) United States Patent
Tavassoli et al.

(10) Patent No.: US 12,385,902 B2
(45) Date of Patent: Aug. 12, 2025

(54) METHODS FOR GENERATING AND SCREENING COMPARTMENTALISED PEPTIDE LIBRARIES

(71) Applicant: UNIVERSITY OF SOUTHAMPTON, Southampton (GB)

(72) Inventors: Ali Tavassoli, Southampton (GB); Catrin Sohrabi, London (GB); Martin Fischlechner, Vienna (AT)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 0 days.

(21) Appl. No.: 16/487,478

(22) PCT Filed: Feb. 22, 2018

(86) PCT No.: PCT/EP2018/054443
§ 371 (c)(1),
(2) Date: Aug. 21, 2019

(87) PCT Pub. No.: WO2018/154021
PCT Pub. Date: Aug. 30, 2018

(65) Prior Publication Data
US 2020/0049695 A1 Feb. 13, 2020

(30) Foreign Application Priority Data
Feb. 23, 2017 (GB) ...................................... 1702938

(51) Int. Cl.
| | | |
|---|---|---|
| *C07K 1/04* | (2006.01) | |
| *C07K 7/64* | (2006.01) | |
| *C12N 15/10* | (2006.01) | |
| *C40B 40/04* | (2006.01) | |
| *G01N 33/50* | (2006.01) | |
| *C40B 40/10* | (2006.01) | |

(52) U.S. Cl.
CPC ......... *G01N 33/5008* (2013.01); *C07K 1/047* (2013.01); *C07K 7/64* (2013.01); *C12N 15/1075* (2013.01); *C40B 40/04* (2013.01); *C40B 40/10* (2013.01)

(58) Field of Classification Search
CPC ................................ G01N 33/50; C12N 15/10
See application file for complete search history.

(56) References Cited

U.S. PATENT DOCUMENTS

| | | | | |
|---|---|---|---|---|
| 9,562,837 B2 * | 2/2017 | Link | ...................... | C12Q 1/6827 |
| 2007/0077572 A1 * | 4/2007 | Tawfik | ...................... | C40B 40/08 435/7.1 |
| 2007/0207502 A1 * | 9/2007 | Benkovic | ................... | C07K 7/64 435/7.1 |
| 2015/0232827 A1 | 8/2015 | Raab et al. | | |
| 2016/0209421 A1 * | 7/2016 | Suga | ................... | G01N 33/6845 |

FOREIGN PATENT DOCUMENTS

| | | |
|---|---|---|
| CN | 1354788 A | 6/2002 |
| CN | 1378593 A | 11/2002 |
| CN | 102209714 A | 10/2011 |
| CN | 102498115 A | 6/2012 |
| JP | 2008 515421 | 5/2008 |
| WO | WO 2000/036093 | 6/2000 |
| WO | 2004029245 A1 | 4/2004 |
| WO | WO 2006 038035 | 4/2006 |
| WO | WO 2010/052569 | 5/2010 |
| WO | 2011005598 A1 | 1/2011 |
| WO | WO 2011/021038 | 2/2011 |
| WO | WO 2011/114539 | 9/2011 |
| WO | WO 2012156744 | 11/2012 |

OTHER PUBLICATIONS

Lennard et al., Peptides Come Round: Using SICLOPPS Libraries for Early Stage Drug Discovery, Chemistry, A European Journal, 2014, 20, 10608-10614. (Year: 2014).*
Foster et al., Methods for the Creation of Cyclic Peptide Libraries for Use in Lead Discovery, Journal of Biomolecular Screening, 2015, 20(5), 563-576. (Year: 2015).*
Lodish et al., The Life Cycle of Cells, Molecular Cell Biology, 4th Edition, National Library of Medicine, National Institutes of Health, Freeman editor, New York, 2000, 1-3. (Year: 2000).*
Tavassoli et al. Methods and Protocols, Chapter 3, Intracellular Production of Cyclic Peptide Libraries with SICLOPPS, Humana Press, H. Mootz ed., epub Oct. 2016, 27-39. (Year: 2016).*
Addgene, Pouring LB Agar Plates, Addgene, 2016, 1-4. Obtained online at: Addgene: Pouring LB Agar Plates on Apr. 27, 2022. (Year: 2016).*
Young et al., Evolution of Cyclic Peptide Protease Inhibitors, PNAS, 2011, 108(27), 11052-11056. (Year: 2011).*
Fischlechner et al., Evolution of Enzyme Catalysts Caged in Biomimetic Gel-Shell Beads, 2014, 1-6. (Year: 2014).*
NEB Expressions, The Next Generation of Cell-Free Protein Synthesis, New England Biolabs, 2008, vol. 3.1, 1-8. (Year: 2008).*
Passioura et al., Selection-Based Discovery of Druglike Macrocyclic Peptides, Annual Review of Biochemistry, 2014, 83, 727-752. (Year: 2014).*
Torre et al., Multiphase Water-In-Oil Emulsion Droplets for Cell-Free Transcription-Translation, Langmuir, 2014, 30, 5695-5699. (Year: 2014).*

(Continued)

*Primary Examiner* — Amy M Bunker
(74) *Attorney, Agent, or Firm* — Pabst Patent Group LLP

(57) ABSTRACT

A method for co-compartmentalising a cyclic polypeptide with a polynucleotide encoding the cyclic polypeptide, comprising the steps of a) forming a compartment containing a polynucleotide encoding the cyclic polypeptide, b) expressing a polypeptide from the polynucleotide, and c) cyclising the polypeptide. Co-compartmentalised cyclic polypeptides and encoding polynucleotides. Libraries of co-compartmentalised cyclic polypeptide and encoding polynucleotide. Methods for screening libraries of co-compartmentalised cyclic polypeptide and encoding polynucleotide. Incorporation of non-canonical nucleic acids into such libraries.

11 Claims, 25 Drawing Sheets
Specification includes a Sequence Listing.

(56) References Cited

OTHER PUBLICATIONS

PCT International Search Report issued in International Application No. PCT/EP2018/054443, dated Jun. 8, 2018.
PCT International Written Opinion issued in International Application No. PCT/EP2018/054443, dated Jun. 8, 2018.
Tavassoli, "SICLOPPS cyclic peptide libraries in drug discovery," *Current Opinion in Chemical Biology*, 38:30-35, 2017.
Kinsella et al., 2002, "Retrovirally delivered random cyclic peptide libraries yield inhibitors of interleukin-4 signalling in human B cells", *J. Biol. Chem.*, 277(40):37512-37518.
Ryckelynck et al., 2015, "Using droplet-based microfluidics to improve the catalytic properties of RNA under multiple-turnover conditions", *RNA*, 21(3):458-469.
Margulies et al., 2005 "Genome sequencing in microfabricated high-density picolitre reactors"., *Nature*, 437(7057):376-80.

* cited by examiner

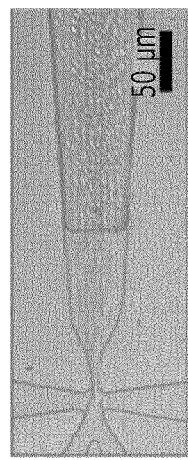
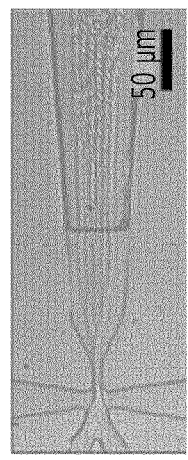
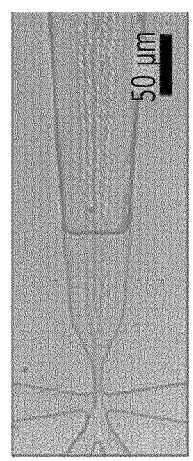
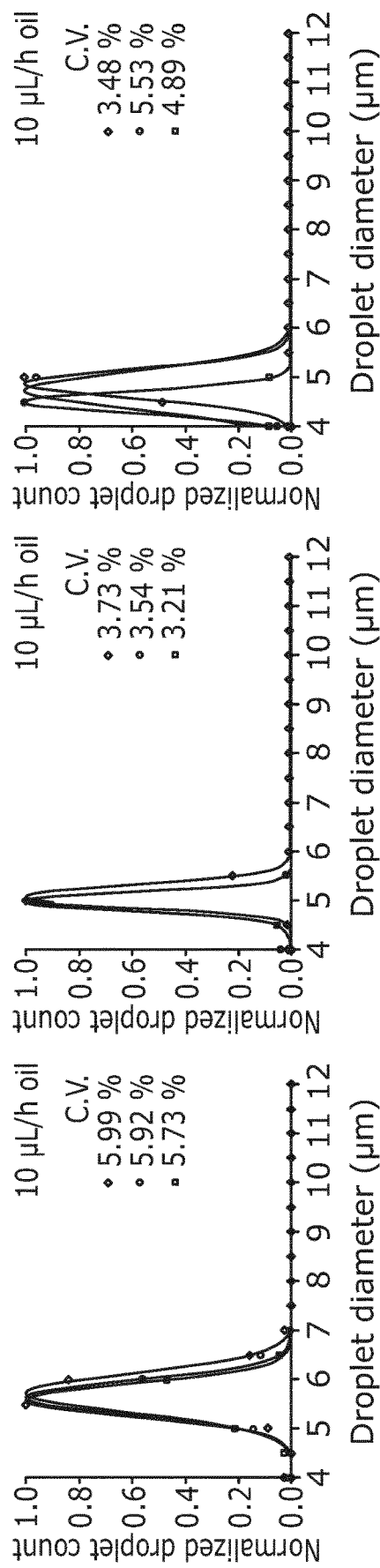
Figure 2D
Figure 2E
Figure 2F

METHODS FOR GENERATING AND SCREENING COMPARTMENTALISED PEPTIDE LIBRARIES

This application is a national phase application under 35 U.S.C. § 371 of International Application No. PCT/EP2018/054443, filed Feb. 22, 2018, which claims the benefit of United Kingdom Patent Application No. 1702938.0, filed Feb. 23, 2017, the entirety of each of which is incorporated herein by reference.

Pursuant to 37 C.F.R. 1.821 (c), a sequence listing is submitted herewith as an ASCII compliant text file named "GJEVP0013US_updated_ST25.txt", created on Aug. 23, 2019 and having a size of ~5 kilobytes. The content of the aforementioned file is hereby incorporated by reference in its entirety.

TECHNICAL FIELD

The present invention relates to the co-compartmentalisation of cyclic peptides with their encoding polynucleotide. In particular, the invention relates to libraries of such compartmentalised cyclic peptides, and methods for the screening, selection, and sorting of compartmentalised cyclic peptides from such libraries.

BACKGROUND TO THE INVENTION

Compartmentalisation of individual samples in aqueous droplets dispersed in an oil phase is a powerful method for high-throughput assays in chemistry and biology. Here the droplet is the equivalent of the test tube. The droplet contains everything needed to assess and decode a particular experiment or profile of a library member. Droplets produced with bulk emulsion techniques are not uniform in size and complications arise in experiments where a quantitative readout is required. Microfluidic devices allow the production of highly monodisperse aqueous droplets, in frequencies up to several (ten-) thousands per second. They are typically 10-200 microns in diameter, corresponding to volumes between 0.5 pL and 4 nL. In addition to droplet formation, the microfluidic format allows a number of other unit operations such as droplet fission, fusion, incubation, analysis and sorting.

Droplet microfluidics deals with the formation of nano- to femto-litre sized oil in water droplets which provide a well-defined and discrete environment that is especially suited to the compartmentalization of single genes, organisms and cells. In particular, miniaturization offers many advantages, including reduced sample consumption, enhanced analytical performance, rapid content mixing, and laminar (streamline) flow.

Aqueous droplets link genotype to phenotype since the compartmentalization they provide mimics that of nature's cells. In each man-made compartment, a single gene is transcribed and translated by cell-free means to give multiple copies of the protein it encodes. This in vitro compartmentalization (IVC) generates "monoclonal units" that are well suited to high-throughput library selections and the identification of novel peptide-based biologics. Since the linkage between genotype and phenotype is not chemically linked but instead co-compartmentalized, a variety of functions (enzymatic, regulatory, inhibitory, binding, and structural) can be selected for. This is advantageous over existing display selection strategies (e.g., bacterial, virus, yeast, and phage display) where selection is based upon binding interactions alone. Since binding does not correlate with inhibition or catalysis, the use of such strategies may inadvertently lead to the selection of poor inhibitors that bind tightly to the enzyme surface, but outside of its active site.

Studies involving in vitro protein expression in emulsified water in oil (w/o) droplets often use green fluorescent protein (GFP) as proof-of-concept. The implementation of microstructured devices for cell-free protein synthesis compartmentalization and GFP expression was first demonstrated by Dittrich et al. Courtois et al later described the utility of integrated chip systems for the storage and on-line detection of droplets containing measureable quantities of in vitro expressed GFP. However, in some cases the isolation of single templates alone does not generate sufficient protein to reach the detection threshold. As with single lacZ genes, expression was undetectable despite the high enzymatic activity of β-galactosidase ($k_{cat}$=187 $s^{-1}$, $K_M$=150 μM). This issue can be overcome through the co-encapsulation of DNA with isothermal amplification systems. On-chip isothermal amplification with Φ29 DNA polymerase is a simple way to generate μg quantities of double stranded DNA. This pre-amplification step involves the co-ordinated fusion of IVTT containing droplets together with those enclosing the amplified DNA, however in many cases the optimal conditions required for DNA amplification, IVTT and any subsequent enzymatic assays differ; for example, components required for successful DNA amplification may inhibit the IVTT. Likewise, it may be necessary to run each process at a different pH value or in different buffer compositions.

Compatibility of different biochemical reactions to each other is a problem when working with water-in-oil droplets. Most biochemical protocols are multi-step processes: solutions are added, samples centrifuged, supernatants removed, pellets washed and so on. Transferring such protocols to droplets is difficult. Although droplet-droplet fusion for adding and/or diluting components can be performed with specialised microfluidic devices, it is practically challenging when large droplet numbers are involved and additional steps (e.g. washing, buffer exchange, addition or removal of reagents) are necessary. Moreover, although droplet fusion is critical for the controlled coalescence of droplet compartments and the initiation of chemical and biological reactions, the process itself is challenging since, for example droplets must achieve both temporal and spatial synchronization for fusion to occur, the stabilizing effects of the utilized surfactants must be overcome and the use of specialized equipment such as electrodes are required for active fusion where the submission of droplets to an electric field induces their coalescence (electro-fusion). This makes droplet fusion difficult or impossible to implement in a continuous workflow An alternative technique for performing multistep compartmentalised reactions in vitro is to use gel beads in microfluidic droplets. These techniques are particularly useful for biochemical processes such as high-throughput screening, directed evolution and genotyping methods.

For example, PCT application number PCT/GB2012/051106 describes the following method for screening a plurality of polypeptides for activity in converting a reporter substrate into a detectable reporter:

1). emulsifying an aqueous reporter solution which comprises a population of polynucleotides, a reporter substrate, and a gel-forming agent into microdroplets, wherein each polynucleotide encodes a product which converts the reporter substrate into a detectable reporter in said microdroplets;

2). solidifying the gel-forming agent within the microdroplet to produce a gel bead comprising the polynucleotide and the detectable reporter produced by the product;

3). de-emulsifying the aqueous microdroplets and resuspending the beads in aqueous detection solution; and 4). detecting, determining or measuring the detectable reporter in one or more beads in said population.

One or more beads from the aqueous solution which contain the detectable reporter or which lack the detectable reporter may be identified and/or isolated. Polynucleotide from the one or more identified beads may be identified, amplified, cloned, sequenced or otherwise investigated. The polynucleotides or nucleic acids may be isolated, for example in plasmids, viruses, or PCR products, or may be comprised in cells or viral particles. The polynucleotides are retained within the gel beads.

In contrast to simple water-in-oil droplets, water-in-oil-in-water (w/o/w) double emulsions provide an internal aqueous compartment for the isolation of biological components along with an aqueous carrier fluid for flow cytometric analysis. Tawfick and Griffiths have previously utilized w/o/w double emulsions as miniaturized micro-reactors for the creation of a genotype-phenotype linkage in directed protein evolution for the identification of potential catalyst "hits" based upon the emergence of product fluorescence, where library members that display the desired activity are subsequently selected for by flow cytometry. However, although numerous microfluidic systems have been developed to make and sort droplets, the operational skill required precludes their ready implementation into a non-specialist setting. Accordingly, we adopt a two-step monodisperse double emulsion droplet methodology as described by Zinchenko et al., which utilizes two independent microfluidics devices with difference surface characteristics for single (hydrophobic device surface coating) and double emulsion droplet formation (hydrophilic device surface coating). The resulting double-emulsion droplets are now suitable for quantitative analysis and sorting via fluorescence activated cell sorting (FACS).

International patent application WO 2000/036093 A2 discloses methods of producing cyclic peptides and splicing intermediates of peptides in a looped conformation. The methods utilize the trans-splicing ability of split inteins to catalyse cyclization of peptides from a precursor peptide having a target peptide interposed between two portions of a split intein. The interaction of the two portions of the split intein creates a catalytically-active intein and also forces the target peptide into a loop configuration that stabilizes the ester isomer of the amino acid at the junction between one of the intein portions and the target peptide. A heteroatom from the other intein portion then reacts with the ester to form a cyclic ester intermediate. The active intein catalyses the formation of an aminosuccinimide that liberates a cyclized form of the target peptide, which spontaneously rearranges to form the thermodynamically favoured backbone cyclic peptide product.

International patent application WO 2012/156744 A2 discloses the use of gel beads in microfluidic droplets to perform multi-step compartmentalised reactions in vitro. Methods may comprise emulsifying an aqueous reporter solution which comprises polynucleotides, a reporter substrate, and a gel-forming agent into microdroplets. Each polynucleotide encodes a product which converts the reporter substrate into a detectable reporter in the microdroplets. The gel-forming agent is then solidified within the microdroplets to produce gel beads comprising both the polynucleotide and the detectable reporter produced by the product. The aqueous microdroplets are then de-emulsified and re-suspended in aqueous detection solution and the reporter detected in one or more beads the population.

Cui, Weitz, Chong, et al. (*Scientific Reports* 6, Article number: 22575) introduced an in vitro two-hybrid system (IVT2H) into microfluidic drops and developed a streamlined mix-and-read drop-IVT2H method to screen a random DNA library. Drop-IVT2H was based on the correlation between the binding affinity of two interacting protein domains and transcriptional activation of a fluorescent reporter. A DNA library encoding potential peptide binders was encapsulated with IVT2H such that single DNA molecules were distributed in individual drops.

Brouzes et al. (PNAS 2009, 106:34, pp. 14195-14200) present a droplet-based microfluidic technology that enables high-throughput screening of single mammalian cells and developed an optically-coded droplet library enabling the identification of the droplets composition during the assay read-out. Using the integrated droplet technology, a drug library was screened for its cytotoxic effect against U937 cells.

Thiele et al. (Lab on a chip, 2014, pages 2651-2652) report the use of hyaluronic acid hydrogel beads for membrane free in vitro transcription/translation. However hyaluronic acid hydrogels, which do not melt, potentially reduce protein yield.

Small linear peptides are useful for investigating various physiological phenomena because they exhibit a wide range of biological activities and can be easily synthesized in almost infinitely variable sequences utilizing conventional techniques in solid phase synthesis and combinatorial chemistry. These qualities also make small linear peptides especially useful for identifying and developing new drugs. For example, large libraries of myriad different small linear peptides can be prepared synthetically and then screened for a particular characteristic in various biological assays. E.g., Scott, J. K. and G. P. Smith, Science 249:386, 1990; Devlin, J. J., et al., Science 24:404, 1990; Furka, A. et al., Int. J. Pept. Protein Res. 37:487, 1991; Lam, K. S., et al., Nature 354:82, 1991. Those peptides within the library that exhibit the particular characteristic can then be isolated as candidates for further study. Sequencing can then be used to characterize selected peptides by, for example, an associated polynucleotide.

Despite these advantages, only a handful of small linear peptides have been developed into widely-used pharmaceutical drugs. One reason for this is that small linear peptides are usually cleared from the body too rapidly to be of therapeutic value Ring closure, or cyclization, can reduce the rate at which peptides are degraded in vivo and therefore dramatically improve their pharmacokinetic properties. Synthetic methods for producing large numbers of different peptides of infinitely variable amino acid sequences greatly facilitates the identification of particular cyclic peptides as candidates for new drugs.

Various methods for producing cyclic peptides have been described. For example, chemical reaction protocols, such as those described in U.S. Pat. Nos. 4,033,940 and 4,102,877, have been devised to produce circularized peptides. In other techniques, biological and chemical methods are combined to produce cyclic peptides. These latter methods involve first expressing linear precursors of cyclic peptides and then adding of an exogenous agent such as a protease or a nucleophilic reagent to chemically convert these linear precursors into cyclic peptides. See, e.g., Camerero, J. A., and Muir, T. W., J. Am. Chem. Society. 121:5597 (1999); Wu, H. et al, Proc. Natl. Acad. Sci. USA, 95:9226 (1998).

Once produced, cyclic peptides can be screened for pharmacological activity. For example, a library containing large numbers of different cyclic peptides can be prepared and then screened for a particular characteristic, such as the ability to bind a specific target ligand. The library is mixed with the target ligand, and those members of the library that bind to the target ligand can be isolated and identified by sequencing an associated polynucleotide. Similarly, libraries of cyclic peptides can be added to assays for a specific biological activity. Those cyclic peptides which modulate the biological activity can then be isolated and identified by sequencing.

Cyclic peptide libraries are increasingly used in high-throughput screens for the identification of inhibitors of a variety of challenging targets. Methods for the generation of such libraries can be divided in two, either genetically encoded approaches—such as phage display or SICLOPPS (Split-Intein Circular Ligation Of Peptides and Proteins)—or chemically synthesized libraries that need to be tagged with a deconvolution code—typically, unique nucleic acid (e.g. RNA or DNA) codes are used to identify each member of the library.

Recent advances in molecular biology have allowed some molecules to be co-selected according to their properties along with the nucleic acids that encode them. The selected nucleic acids can subsequently be cloned for further analysis or use, or subjected to additional rounds of mutation and selection.

Common to these methods is the establishment of large libraries of nucleic acids. Molecules having the desired characteristics (activity) can be isolated through selection regimes that select for the desired activity of the encoded polypeptide, such as a desired biochemical or biological activity, for example binding activity.

Phage display technology has been highly successful at providing a vehicle that allows for the selection of a displayed protein by providing the essential link between nucleic acid and the activity of the encoded polypeptide (Smith, 1985; Bass et al., 1990; McCafferty et al., 1990; for review see Clackson and Wells, 1994). Filamentous phage particles act as genetic display packages with proteins on the outside and the polynucleotides which encode them on the inside. The tight linkage between nucleic acid and the activity of the encoded polypeptide is a result of the assembly of the phage within bacteria. As individual bacteria are rarely multiply infected, in most cases all the phage produced from an individual bacterium will carry the same polynucleotide and display the same protein.

However, phage display relies upon the creation of nucleic acid libraries in vivo in bacteria. Thus, the practical limitation on library size allowed by phage display technology is of the order of $10^7$ to $10^{11}$, even taking advantage of λ phage vectors with excisable filamentous phage replicons. The technique has mainly been applied to selection of molecules with binding activity. A small number of proteins with catalytic activity have also been isolated using this technique, however, selection was not directly for the desired catalytic activity, but either for binding to a transition-state analogue (Widersten and Mannervik, 1995) or reaction with a suicide inhibitor (Soumillion et al., 1994; Janda et al., 1997). More recently there have been some examples of enzymes selected using phage-display by product formation (Atwell & Wells, 1999; Demartis et al., 1999; Jestin et al., 1999; Pederson, et al., 1998), but in all these cases selection was not for multiple turnover.

While larger libraries can be generated by mRNA display, these libraries are also limited to affinity based screening and suffer from the same shortcomings as phage display.

mRNA display is a technique for linking genotype and phenotype by covalently coupling an mRNA as genotype and a peptide molecule as phenotype using a cell-free translation system (in vitro transcription/translation system), and applied by coupling a synthesized peptide molecule and an mRNA encoding it via puromycin, which is an analogue of the 3' end of a tyrosyl-tRNA.

In mRNA display (see Szostak, J. W. and Roberts, R. W., U.S. Pat. No. 6,258,558, the contents of which are incorporated herein by reference in their entirety), each mRNA molecule in the library is modified by the covalent addition of a puromycin-like moiety at its 3' terminus. The puromycin-like moiety is an aminoacyl-tRNA acceptor stem analog that functions as a peptidyl acceptor, and can be added to a growing polypeptide chain by the peptidyl transferase activity of a ribosome translating the mRNA. During in vitro translation, the mRNA and the encoded polypeptide become covalently linked through the puromycin-like moiety, creating an RNA-polypeptide fusion. After selecting a fusion molecule by binding of its polypeptide component to a target (i.e. by screening), the RNA component of the selected fusion molecule can be amplified using PCR, and then characterized. Several other methods have been developed to produce a physical linkage between a polypeptide and its encoding nucleic acid to facilitate selection and amplification (see Yanagawa, H., Nemoto, N., Miyamoto, E., and Husimi, Y., U.S. Pat. No. 6,361,943; Nemoto, H., Miyamoto-Sato, E., Husimi, H., and Yanagawa, H. (1997). FEBS Lett. 414:405-408; Gold, L., Tuerk, C., Pribnow, D., and Smith, J. D., U.S. Pat. Nos. 5,843,701 and 6,194,550; Williams, R. B., U.S. Pat. No. 6,962,781; Baskerville, S. and Bartel, D. P. (2002). Proc. Natl. Acad. Sci. USA 99:9154-9159; Baskerville, D. S. and Bartel, D. P., U.S. Pat. No. 6,716,973; Sergeeva, A. et al. (2006). Adv. Drug Deliv. Rev. 58:1622-1654; the contents of each of which are incorporated herein by reference in their entirety).

mRNA display is a particularly useful method for creating large libraries of peptides.

In mRNA display, an mRNA containing puromycin preliminarily attached to its 3' end via a suitable linker is introduced into a cell-free translation system to synthesize a peptide from the mRNA so that the puromycin is fused to the C-terminus of a growing peptide chain as a substrate for peptidyl transfer reaction on a ribosome. The translated peptide molecule is fused to the mRNA via the puromycin moiety. Puromycin is characterized in that it forms an amide bond to the nascent peptide rather than an ester bond, unlike the 3' end of an aminoacyl-tRNA. Thus, the conjugate of the puromycin and the peptide fused to each other on the ribosome is resistant to hydrolysis and stable.

In mRNA display, it is necessary to attach puromycin to the 3' end of the mRNA. This attachment may take place by first preparing a puromycin-conjugated linker having a spacer consisting of a linear polymer and then fusing the linker to the 3' end of the mRNA. The attachment may also take place by first conjugating a spacer to the 3' end of the mRNA and then fusing the puromycin to the conjugate. In either method, the linear polymer spacer typically contains a phosphate group or nucleotide at an end, and the linkage between the 3' end of the mRNA and the 5' end of the linker is a covalent bond via the phosphate group. This covalent bond is formed by a reaction using an RNA ligase or DNA ligase or a standard organic chemistry reaction.

EP 2492344 A1 discloses a modified mRNA display method known as "RAPID." The linker in the RAPID display method of the present invention connects an mRNA and a peptide translated therefrom by binding to the 3' end of the mRNA at one end and to the C-terminus of the nascent peptide at the other end in the same manner as in known mRNA display methods.

However, the linker in the RAPID display method differs in the structure of both ends from those used in known mRNA display methods. The linker used in the RAPID display method is herein sometimes referred to as "RAPID linker".

The region at one end of the linker binding to the C-terminus of a peptide is herein sometimes referred to as "peptidyl acceptor" or simply "acceptor". Thus, the term "peptidyl acceptor" refers to a molecule or moiety having a structure capable of binding to a peptide growing by peptidyl transfer reaction on a ribosome (peptidyl-tRNA). The peptidyl acceptor may refer to a region located at an end of a linker or may refer to a whole structure including a linker. For example, the peptidyl acceptor in known mRNA display methods is puromycin located at one end of a linker or a puromycin-conjugated linker as a whole structure including a linker.

The RAPID linker is characterized by the structure and the preparation process of the peptidyl acceptor.

In the RAPID display method, a linker having a sequence consisting of a 4-residue ribonucleotide ACCA is synthesized at the 3' end, and then an amino acid is attached to adenosine at the 3' end, thereby conferring a structure as peptidyl acceptor on the linker. During peptide elongation reaction on a ribosome, the amino acid attached to the end of the linker accepts the C-terminus of the peptide of the peptidyl-tRNA and binds to the peptide. The structure in which an amino acid is attached to the RNA sequence ACCA via an ester bond is herein referred to as "peptidyl acceptor region".

The peptidyl acceptor in known mRNA display methods is puromycin, which has an aminonucleoside structure in which a ribose in the adenosine-like moiety and an amino acid are linked via an amide bond. In the RAPID display method, however, an amino acid is attached to the 3'-O of ribose via an ester bond. In other words, the peptidyl acceptor in the RAPID display has a nucleoside structure similar to that of natural aminoacyl-tRNA. The peptidyl acceptor shows an incorporation efficiency comparable to or higher than that of puromycin by adopting a structure closer to that of the natural acceptor.

The formation of a bond between the peptidyl acceptor and the C-terminus of the peptide seems to occur by the proximity of the amino group of the peptidyl acceptor incorporated into the A site to the ester bond at the C-terminus of the attached peptide of the peptidyl-tRNA in the P site in the same manner as normal peptidyl transfer reaction in ribosomes. Thus, the covalent bond formed with the C-terminus of the peptide chain is typically an amide bond in the same manner as in mRNA display. It should be noted that a linker having an unnatural (non-canonical/non-natural/non-proteinogenic) amino acid such as a D-amino acid or β (beta)-amino acid can also be used in the RAPID display of the present invention by using an artificial RNA catalyst (flexizyme) for the synthesis of the linker.

In the RAPID display method, the 5' end of the linker and the 3' end of an mRNA molecule forms a complex by hybridization based on base pairing. This region in the RAPID linker is herein referred to as "single-stranded structure region". Specific examples of single-stranded structures having a nucleic acid base in the side chain include single-stranded DNAs, single-stranded RNAs, single-stranded PNAs (peptide nucleic acids), etc. The resulting complexes must remain stable during peptide selection from the mRNA library. As the complementarity between the nucleotide sequence of the single-stranded structure region of the linker and the sequence of the 3' end of the mRNA molecule increases, the efficiency of double-strand formation increases and stability also increases. Stability also depends on the GC content, the salt concentration of the reaction solution, and reaction temperature. Especially, this region desirably has a high GC content, specifically a GC content of 80% or more, preferably 85% or more.

The rest of the linker excluding both ends is designed to have a flexible, hydrophilic and simple linear structure with less side chains as a whole similarly to the structure of linkers used in known mRNA display methods. Therefore, linear polymers including, for example, oligonucleotides such as single- or double-stranded DNA or RNA; polyalkylenes such as polyethylene; polyalkylene glycols such as polyethylene glycol; polystyrenes; polysaccharides; or combinations thereof can be appropriately selected and used. The linker preferably has a length of 100 angstroms or more, more preferably about 100-1000 angstroms.

The advantage of the RAPID system is that association between the peptidyl acceptor region and the library mRNA can occur in situ with the IVTT system, i.e. there is no need for a preliminary ligation step, e.g. between puromycin and the linker or between the linker and the mRNA.

Moreover, non-natural (non-canonical) amino acids can be incorporated in the same translation system. For example, the acylation reaction for charging a tRNA with a non-proteinogenic amino acid or hydroxy acid, which is a constituent unit of an unusual peptide, may be mediated by an artificial RNA catalyst (ribozyme), e.g. flexizyme.

Specific peptide ligands have been selected for binding to receptors by affinity selection using large libraries of peptides linked to the C terminus of the lac repressor LacI (Cull et al., 1992). When expressed in *E. coli* the repressor protein physically links the ligand to the encoding plasmid by binding to a lac operator sequence on the plasmid.

An entirely in vitro polysome display system has also been reported (Mattheakis et al., 1994; Hanes and Plucktin, 1997) in which nascent peptides are physically attached via the ribosome to the RNA which encodes them. An alternative, entirely in vitro system for linking genotype to phenotype by making RNA-peptide fusions (Roberts and Szostak, 1997; Nemoto et al., 1997) has also been described.

However, the scope of the above systems does not allow direct selection for activities other than binding, for example catalytic or regulatory activity. The majority of these approaches are only compatible with affinity-based assays. However, the majority of pharmaceutical assays are functional and, in any case, functional assays are superior; just because a compound binds a target protein does not mean it has any biological function.

One exception is the SICLOPPS method, which can be interfaced with both affinity-based and functional assays. However, up to now SICLOPPS has only been demonstrated in cell-based in vivo systems.

In SICLOPPS systems, a nucleic acid molecule may be constructed such that a nucleotide sequence encoding the peptide to be cyclized is flanked on one end with a nucleotide sequence encoding the carboxy-terminal portion of a split (or trans) intein (C-intein or $I_C$) and on its other end with a nucleotide sequence encoding the amino-terminal portion of a split intein (N-intein or $I_N$). Expression of the construct results in the production of a fusion protein. The two split intein components (i.e., $I_C$ and $I_N$) of the fusion protein then assemble to form an active enzyme that splices the amino and carboxy termini of the intervening sequence together to generate a backbone cyclic peptide. The chemical reaction is depicted in FIG. 14. This method can be adapted to facilitate the selection or screening of cyclic peptides with predetermined characteristics.

Accordingly the invention may feature a non-naturally occurring nucleic acid molecule encoding a polypeptide having a first portion of a split intein, a second portion of a split intein, and a target peptide interposed between the first portion of a split intein and the second portion of a split intein. Expression of the nucleic acid molecule produces a polypeptide that spontaneously splices to yield a cyclized form of the target peptide, or a splicing intermediate of a cyclized form of the target peptide such as an active intein intermediate, a thioester intermediate, or a lariat intermediate.

Both the first portion of a split intein and the second portion of a split intein can be derived from a naturally-occurring split intein such as Ssp DnaE. In other variations, one or both of split intein portions can be derived from non-naturally occurring split inteins such as those derived from RecA, DnaB, Psp Pol-1, and Pfu inteins.

In Tawfik and Griffiths (1998), and in International patent application PCT/GB98/01889, there is described a system for in vitro evolution that overcomes many of the limitations described above by using compartmentalisation in microcapsules to link genotype and phenotype at the molecular level.

In Tawfik and Griffiths (1998), and in several embodiments of International patent application PCT/GB98/01889, the desired activity of a polypeptide results in a modification of the polynucleotide which encoded it (and is present in the same microcapsule). The modified polynucleotide can then be selected in a subsequent step. However, these approaches do not contemplate cyclic polypeptides.

There is accordingly a need for a method for the generation and tagging of cyclic peptide libraries that would be compatible with any pharmaceutical assay. The present invention addresses this need by providing cyclic polypeptides co-compartmentalised with their encoding polynucleotide, in a format compatible with pharmaceutical assays and peptide library generation.

SUMMARY OF THE INVENTION

The present invention advantageously provides cyclic polypeptides in a format that can be interfaced with any pharmaceutical assay, particularly with functional assays, and which allows each polypeptide to be easily and uniquely identified.

In a first aspect, there is disclosed a method for producing a cyclic polypeptide co-compartmentalised with a polynucleotide encoding the cyclic polypeptide, comprising the steps of:
  a) forming a compartment containing a polynucleotide encoding the cyclic polypeptide;
  b) expressing a polypeptide from the polynucleotide; and
  c) cyclising the polypeptide.

In embodiments, cyclising the polypeptide is a passive process. In other words, the polypeptide may self-cyclise or auto-cyclise. The passive process may be an "auto-catalytic" process. For example, the polypeptide might be a SICLOPPS polypeptide. In such cases, the step of "(c) cyclising the polypeptide" involves merely allowing the polypeptide to cyclise, e.g. by allowing the reaction to proceed for a suitable length of time. In embodiments, a suitable length of time for cyclisation may be a matter of seconds. In other embodiments, a suitable length of time for cyclisation may be a matter of minutes, hours, or days. The time necessary for cyclisation may vary significantly for any given polypeptide. However, determination of the suitable length of time to allow a desired degree of cyclisation is within the purview of the person skilled in the art.

Alternatively, the polypeptide may be cyclised by other methods known in the art, such as chemical or enzymatic methods. In these "non-passive" methods of cyclisation, the components necessary for cyclisation are allowed to come into contact with the polypeptide and the reaction is subjected to the necessary conditions for a suitable length of time to bring about the desired degree of cyclisation. In embodiments, a suitable length of time for cyclisation may be a matter of seconds. In other embodiments, a suitable length of time for cyclisation may be a matter of minutes, hours, or days. The time necessary for cyclisation may vary significantly for any given polypeptide. However, determination of the suitable length of time to allow a desired degree of cyclisation is within the purview of the person skilled in the art.

Since expression of the cyclic polypeptide occurs within the compartment, the polynucleotide encoding the cyclic peptide is contained in the same compartment. This makes the cyclic polypeptide uniquely identifiable by isolating and sequencing its co-compartmentalised polynucleotide. The compartment also forms a micro-reactor, containing all of the components of the expression system, and/or any other reaction components.

The polynucleotide may be non-covalently associated with its encoded product, for example the polynucleotide and the encoded product may be contained within the same bead, compartment, cell, or viral particle. The polynucleotide and its encoded product may be linked directly or indirectly through a non-covalent attachment.

Alternatively or additionally, the polynucleotide may be covalently associated with its encoded product, for example through a puromycin moiety in an mRNA display system.

In a second aspect, there is disclosed a method for sorting cyclic polypeptides, comprising the steps of:
  a) forming a compartment containing a polynucleotide encoding the cyclic polypeptide;
  b) expressing a polypeptide from the polynucleotide;
  c) cyclising the polypeptide;
  d) screening the cyclic polypeptide for activity; and
  e) selecting the cyclic polypeptide exhibiting a desired activity.

For example, the cyclic polypeptide may be used to induce or inhibit fluorescence. Beads and/or compartments exhibiting or not exhibiting fluorescence may then be selected and/or sorted accordingly, such as by Fluorescence Activated Droplet Sorting (FADS). Cyclic peptides exhibiting the desired characteristics can later be identified by sequencing the associated polynucleotide.

In embodiments, the method further comprises the step of identifying selected cyclic polypeptides. For example, by sequencing a polynucleotide that is associated with the polypeptide by virtue of the present invention.

In some embodiments, the compartment may be a droplet of water-in-oil (w/o) or water-in-oil-in-water (w/o/w) emulsion obtained by microfluidic manipulation of a solution comprising the polynucleotide.

In other embodiments, the compartment may be a microcapsule obtained by bioelectrospray or jetting of a suitable solution of the polynucleotide in polyelectrolyte, such as an alginate compartment.

In still other embodiments, the compartment may be a vesicle, such as a lipid vesicle.

The methods may further comprise the step of amplifying the polynucleotide. The increased copy number of the polynucleotide ultimately can result in a higher expression of cyclic polypeptide. This facilitates detection of the cyclic polypeptide in any subsequent assay, thus improving its sensitivity.

The compartment may also comprise a gel-forming agent, wherein the gel-forming agent is solidified (or formed) into a gel bead after the polynucleotide has been amplified. The amplified polynucleotides are trapped (or fixed) in the gel matrix, thus holding the identical polynucleotide copies within a single bead. This prevents the loss of amplified copies of the polynucleotide from the bead if the compartment is later disrupted, thus maintaining the ability to uniquely identify the bead. Gel-forming agents can be made to form a gel by, for example, cooling to a temperature at which the gel forms.

During the amplification reaction, an external source of heat may be applied. This may be achieved by applying heat to the reaction vessel or container in which amplification is being carried out, e.g. in a glass syringe. This may stimulate the amplification reaction. Alternatively or in addition, in embodiments employing a gel-forming agent, application of heat maintains the gel in the liquid phase.

Preferably, heat is evenly and continuously applied to the container at a constant temperature. By "evenly" applied, it is meant that substantially all of the surface of the container is subjected to the same degree of heating, i.e. any given point on the surface of the container receives the same amount of heat energy as any other given point on the surface of the container. In embodiments, "substantially all" of the container includes just one surface of the container that laterally encloses or encircles the container, or a plurality of surfaces that together laterally enclose or encircle the container. For example, the container may be a syringe with a circular cross-section and therefore having a generally cylindrical form with a single, lateral, curved surface encircling the syringe (the side surface) which is capped by two circular surfaces (the top and bottom surfaces). In this example, heat is evenly applied to the surface of the container if any given point on the curved (side) surface receives the same amount of heat energy as any other given point on that curved (side) surface, regardless of the amount of heat energy received by either of the capping (top and bottom) surfaces.

The external heat source may comprise a flexible heating element or filament. The heat source may be electronically powered. In embodiments, the heat source is a commercially available electronic heating pad. In other embodiments, the heat source may be a fluid-filled jacket, into which a heated fluid, e.g. water, is continuously pumped from a heated fluid source. In embodiments, the external heat source may be formed integrally with the container.

After formation of the gel bead, the compartment may be disrupted. This allows the conditions to which the bead is exposed to be changed. For example, the buffer solution can be changed by a buffer exchange procedure. The new buffer solution can infiltrate the gel bead and interact with the polynucleotide copies, or any other components, held within the beads. This can lead to the activation of new processes, such as gene expression.

Each gel bead also represents a mechanically stable unit and can be considered as a reservoir of polynucleotides with identical sequence. Each bead can be individually manipulated. For example, a bead can be fed into a microfluidics device for emulsification.

In some embodiments, the gel bead can be exposed to conditions for expressing the cyclic polypeptide. For example, the gel bead can be exposed to an In vitro transcription and translation (IVTT) system.

A compartment may be formed around the gel bead after and/or during exposure to conditions for expressing the cyclic polypeptide. In other words, the bead is re-compartmentalised, meaning that the uncompartmentalised bead has a new compartment formed around it. This second compartmentalisation step may follow the same procedure as the first compartmentalisation described above. Alternatively, the second compartmentalisation step may follow a different procedure. For example, the first compartmentalisation could be by microfluidics to form a droplet of emulsion containing the gel bead and the second compartmentalisation could be by a jetting procedure with polyelectrolyte to form a compartment containing the gel bead. In an alternative example, both the first and the second compartmentalisation procedures are by microfluidics to form a droplet of emulsion containing the bead.

After translation, the beads may be subjected to an assay. For example, the cyclic peptides can be assessed for their potential to inhibit a target enzyme by an optical assay, such as a colorimetric or fluorometric assay. If the enzyme catalyses a reaction that produces a coloured or fluorescent product, then a bead containing inhibitory polypeptide will have a reduced colour or fluorescence intensity compared to other beads containing non-inhibitors. The beads can be sorted in a high-throughput manner, for example by fluorescence activated cell sorting (FACS) or fluorescence activated droplet sorting (FADS). In embodiments, the beads are in droplets of emulsion. To be compatible with FACS/FADS, the continuous phase of an emulsion should be aqueous.

The polynucleotide may comprise a sequence encoding an N-terminal intein fragment, followed by a sequence encoding the cyclic polypeptide, followed by a sequence encoding a C-terminal intein fragment. When expressed as a polypeptide, the N-terminal intein fragment associates with the C-terminal intein fragment. This causes the intervening polypeptide, comprising the desired cyclic polypeptide, to form a polypeptide loop. The intein-loop structure then spontaneously undergoes a splicing reaction, which yields the free intein and the desired cyclic polypeptide. The desired polynucleotide can be obtained by conventional molecular cloning techniques.

In any aspect or embodiment, the compartment may be a droplet of water-in-oil-in-water (w/o/w) emulsion, a vesicle, or a compartment.

In a third aspect, there is disclosed a compartment comprising:
  a) a polynucleotide encoding an N-terminal intein fragment, followed by a sequence encoding a cyclic peptide, followed by a sequence encoding a C-terminal intein fragment; and
  b) the cyclic polypeptide.

Expression of the polynucleotide produces a linear polypeptide comprising an N-terminal intein fragment, an intervening cyclic polypeptide sequence, and a C-terminal intein fragment. The linear peptide may undergo a spontaneous splicing reaction at the junctions between the intein fragments and the cyclic polypeptide sequence, thus producing the cyclic polypeptide and a free intein moiety. This is one way in which a compartment can be made to contain both a cyclic polypeptide and its encoding polynucleotide. Such compartmentalised cyclic polypeptides can be assayed. In particular, the compartmentalised cyclic polypeptides are compatible with pharmaceutical assays, including functional assays. This allows high-throughput screening and selection of promising cyclic polypeptide candidate compounds, for example in drug discovery. This is especially the case if using a library according to the invention.

Accordingly the invention may feature a non-naturally occurring nucleic acid molecule encoding a polypeptide having a first portion of a split intein, a second portion of a split intein, and a target peptide interposed between the first portion of a split intein and the second portion of a split intein. Expression of the nucleic acid molecule produces a polypeptide that spontaneously splices to yield a cyclized form of the target peptide, or a splicing intermediate of a cyclized form of the target peptide such as an active intein intermediate, a thioester intermediate, or a lariat intermediate.

The invention may be used to encode cyclic polypeptides containing one or more non-natural amino acids by using a re-assigned codon set, combined with custom IVTT mixtures containing specific tRNA loaded with a non-natural amino acid; tRNA charged with a non-natural amino acid may be readily generated using previously reported methods. For example, the acylation reaction for charging a tRNA with a non-proteinogenic amino acid or hydroxy acid, which is a constituent unit of an unusual peptide, may be mediated by an artificial RNA catalyst (ribozyme), e.g. flexizyme.

Both the first portion of a split intein and the second portion of a split intein can be derived from a naturally-occurring split intein such as Npu or Ssp DnaE. In other variations, one or both of split intein portions can be derived from natural, engineered, or non-naturally occurring split inteins such as those derived from RecA, DnaB, Psp Pol-1, and Pfu inteins.

In a fourth aspect, there is provided a library of cyclic polypeptides co-compartmentalised with their encoding polynucleotide. The library comprises a plurality of such compartments, wherein the polynucleotide in at least one compartment comprises a sequence that is different (i.e. not identical) to the sequence of a polynucleotide in at least one other compartment (i.e. a different compartment). The library may be screened, for example by subjecting it to a fluorescence or colourimetric assay, and those compartments exhibiting the desired signal selected, for example by FADS.

In another aspect, there is provided a kit comprising:
a) a microfluidics device;
b) a polynucleotide encoding an N-terminal intein fragment; and
c) a polynucleotide encoding a C-terminal intein fragment.

In embodiments, the kit comprises a capsule forming material. The capsule forming material may be an oil, a lipid, or a polyelectrolyte.

In some embodiments, the kit also comprises a gel-forming agent.

The polynucleotides encoding intein fragments can be used to produce a polynucleotide encoding the cyclic polypeptide sequence flanked by the N-terminal intein fragment at one end and the C-terminal intein fragment at the other end. This can be achieved by conventional molecular cloning techniques, for example by ligation of the intein-encoding sequences to a nucleotide encoding the cyclic polypeptide.

BRIEF DESCRIPTION OF FIGURES

FIGS. 2A-F. Analysis of single water-in-oil emulsion droplet dimensions. The ability to finely control the generated droplet diameter was determined through maintaining a constant aqueous flow rate of 10 µL/h whilst increasing the oil/surfactant flow rate from 10-60 µL/h (A-F, respectively). The brightfield photograph above each diameter distribution histogram represents the resulting droplet generation stream during collection under each condition. For each experiment, three independent images were analysed and the resulting droplet diameters plotted to obtain a diameter histogram; in each case the y-axis (droplet count) was normalized and the results presented as fractions. A Gaussian normal distribution was fitted in each case with a constrained amplitude of 1. The Coefficient of Variation (C.V.) for each photograph is presented alongside each set. Bin size=0.5 µm.

DETAILED DESCRIPTION OF PREFERRED EMBODIMENTS

Figure 1:
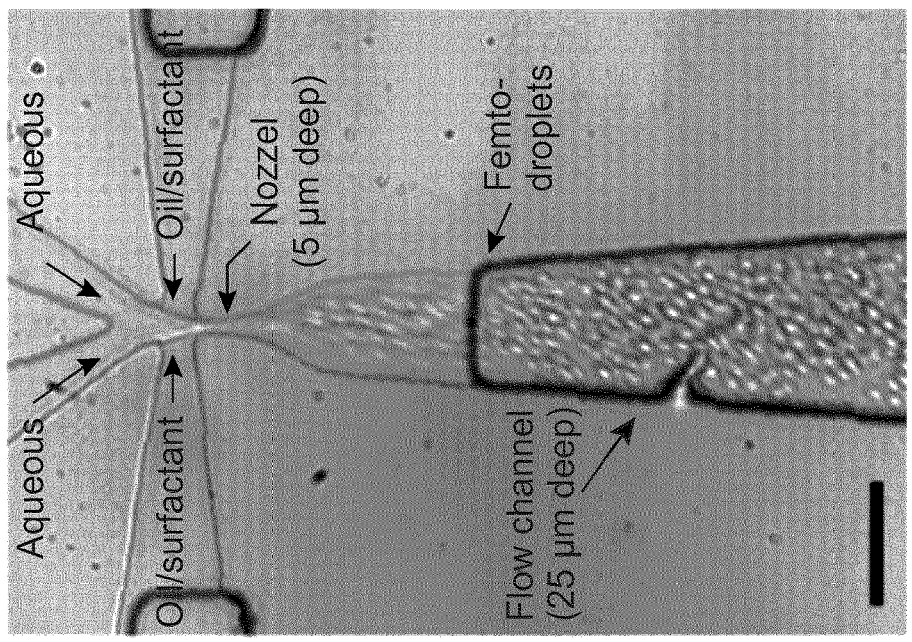
FIG. 1. Microfluidic device used for the generation and manipulation of femtolitre-sized droplets. (Left) PDMS device bound to a glass slide for the controlled generation of femtodroplets; (right) photograph of device operation—droplet formation occurs at the nozzle of the microfluidic chip (10 µm wide×5 µm deep) whilst newly generated droplets migrate through the flow channel (100 µm wide×25 µm deep). Four inlets are provided for the injection and thus introduction of fluids into the device: the two outer ports are used for oil whilst the middle two are used for aqueous solutions. Scale bar=50 µm.
Figure 1:
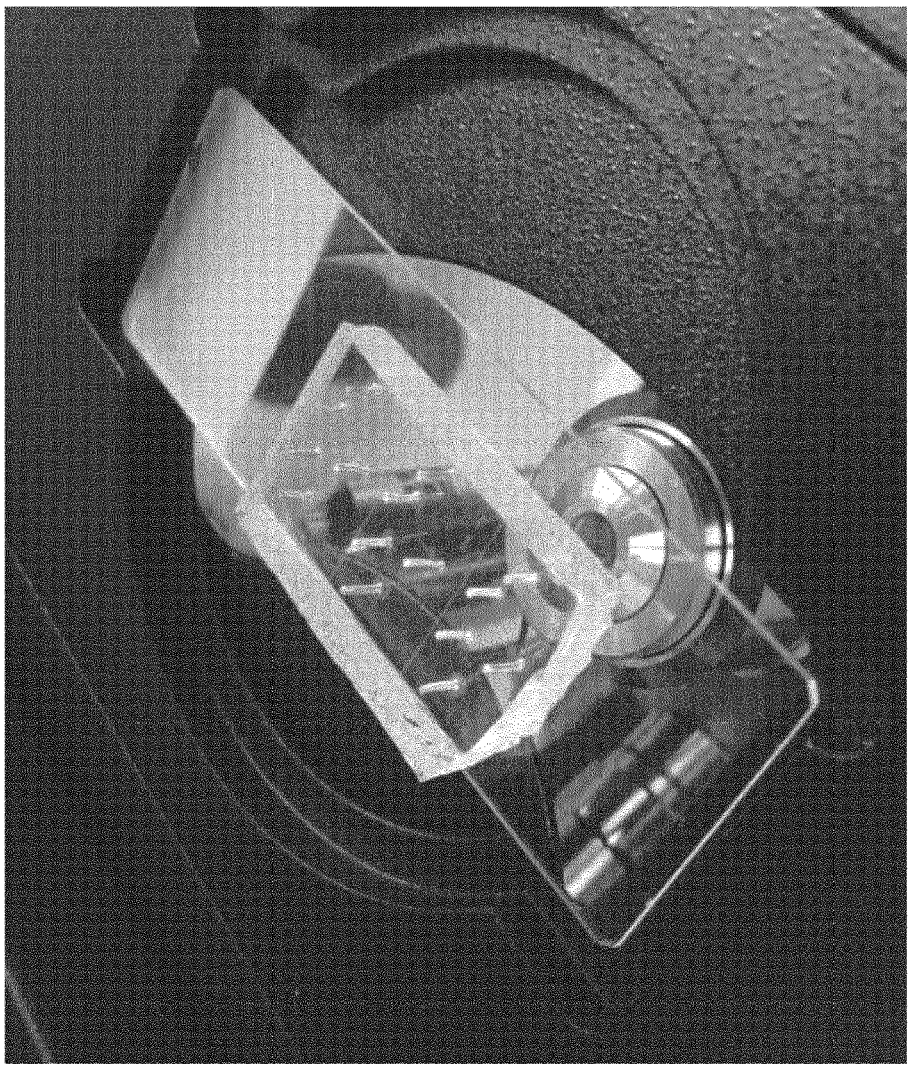

Unless defined otherwise, all technical and scientific terms used herein have the same meaning as commonly understood by those of ordinary skill in the art, such as in the arts of peptide chemistry, microfluidics, nucleic acid chemistry, molecular genetics and cloning, and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4th ed., John Wiley & Sons, Inc.), which are incorporated herein by reference.

A "linear polypeptide" is a peptide that is not in a circular form, and generally has both a carboxy-terminal amino acid with a free carboxy-terminus and an amino-terminal amino acid with a free amino terminus.

As used herein, the word "intein" means a naturally-occurring or artificially constructed polypeptide sequence embedded within a precursor protein that can catalyse a splicing reaction during post-translation processing of the protein. A list of some of the known inteins is published at http://www.inteins.com.

A "split intein" is an intein that has two or more separate components not fused to one another.

As used herein, the word "interposed" or "intervening" means placed in between. Thus, in a polypeptide having a first sequence interposed between a second and a third sequence (or a second and third sequence with an intervening first sequence), the chain of amino acids making up the first sequence is physically located in between the chain of amino acids making up the second sequence and the chain of amino acids making up the third sequence.

In comparison, a "cyclic polypeptide" is a polypeptide that has been "cyclised." The term "cyclic" means having constituent atoms forming a ring. When referring to a peptide, the term "cyclise" means to make the peptide into a cyclic or "cyclised" form. Thus, for example, a linear peptide is "cyclised" when its free amino-terminus is covalently bonded to its free carboxy-terminus (i.e., in a head to tail format) such that no free carboxy- or amino terminus remains in the peptide.

As used herein, the word "spontaneously" means the action described occurs without the addition of an exogenous substance. For example, a precursor polypeptide spontaneously splices to yield a cyclic peptide when nothing is added to the host system other than the precursor polypeptide or a nucleic acid molecule encoding the precursor polypeptide. In comparison, a precursor polypeptide within a host system does not spontaneously splice in the host system if an agent extraneous to the host system is required to generate the cyclic peptide.

As used herein, the phrase "expression vector" means a vehicle that facilitates transcription and/or translation of a nucleic acid molecule in a suitable in vitro or in vivo system. An expression vector is "inducible" when adding an exogenous substance to a host system containing the expression vector causes the vector to be expressed (e.g., causes a nucleic acid molecule within the vector to be transcribed into mRNA).

As used herein, the phrase "regulatory sequence" means a nucleotide sequence which modulates expression (e.g., transcription) of a nucleic acid molecule. For example, promoters and enhancers are regulatory sequences.

The invention brings novel features and attendant advantages, which can be explained, in more detail in connection with the generation of polypeptides—in particular, cyclic polypeptides—identifiably tagged (or labelled) by co-compartmentalisation with their encoding polypeptide. In particular, the invention provides novel means for performing functional assays on genetic libraries, which cannot be achieved by known genetic libraries. Prior art libraries, such as phage display libraries, are compatible with affinity-based assays, but do not effectively interface with functional assays. The majority of pharmaceutical assays are functional, in part because a functional assay provides a more accurate indication of biological (or physiological) activity than an affinity assay. Therefore, there is an unmet need for a technology that combines the diversity and high-throughput of a genetic library with the flexibility to be interfaced with a functional assay.

4.1 Compartments

In the first aspect, the invention relates to a method for expressing a cyclic polypeptide within a compartment, comprising the step of forming a compartment containing a polynucleotide, the polynucleotide comprising a sequence which encodes the cyclic polypeptide.

A compartment is comprised of a physical boundary which delineates an interior volume separate from an external environment. In embodiments, the compartment is substantially spherical. The compartment may be a particle in solution, for example a particle suspended in solution, such as a colloid, or a droplet in emulsion.

The interior volume of the compartment must be sufficient to contain at least one polynucleotide molecule and one cyclic polypeptide.

To ensure that the polynucleotide and polypeptides may not diffuse between compartments, the contents of each compartment are preferably isolated from the contents of the surrounding compartments, so that there is no or little exchange of the polynucleotide and polypeptide between the compartments over the timescale of the experiment.

The physical boundary of the compartment may be formed from any material that can prevent egress of the enclosed polynucleotide, and any associated polypeptide, out of the compartment. The compartment may be semipermeable, thus forming a barrier to the movement of one component, such as a polynucleotide, whilst permitting the movement of other components, such as buffer constituents or nucleotide phosphates (e.g. nucleotide triphosphates). Therefore, the interior of a semi-permeable compartment may be a thermodynamically open system, allowing both matter and energy to cross its boundary, albeit in a selective manner. Alternatively, the compartment may be impermeable, forming a barrier to the movement of all components, species, and moieties, including media, such as aqueous solutions, water, and oils, though still remaining capable of energy exchange with the external environment.

Compartmentalisation is a process by which a compartment is formed. When an entity is described as being compartmentalised, this means that the entity is contained within a compartment.

As used herein, the term "compartmentalisation" is synonymous with "encapsulation." Accordingly, the term "compartment" is synonymous with "capsule."

The compartments of the present invention require appropriate physical properties to allow the working of the invention. The formation and the composition of the compartments advantageously does not abolish the function of the machinery for the expression of the polynucleotides or the activity of the polypeptides. The appropriate system(s) may vary depending on the precise nature of the requirements in each application of the invention, as will be apparent to the skilled person.

Suitable compartments and compartment-forming materials include droplets of emulsion, lipid vesicles, and microcapsules.

4.1.1 Compartment Sizes

The preferred compartment size will vary depending upon the precise requirements of any individual selection process that is to be performed according to the present invention. In all cases, there will be an optimal balance between gene library size, the required enrichment and the required concentration of components in the individual compartments to achieve efficient expression and reactivity of the polypeptides.

The processes of expression occurs within each individual compartment provided by the present invention. Both in vitro transcription and coupled transcription-translation become less efficient at sub-nanomolar DNA concentrations. Because of the requirement for only a limited number of DNA molecules to be present in each compartment, this therefore sets a practical upper limit on the possible compartment size. Preferably, the mean volume of the compartments is less than $5.2 \times 10^{-16}$ m$^3$, (corresponding to a spherical compartment of diameter less than 10 μm, more preferably less than $6.5 \times 10^{-17}$ m$^3$ (5 μm diameter), more preferably about $4.2 \times 10^{-18}$ m$^3$ (2 μm diameter) and ideally about $9 \times 10^{-18}$ m$^3$ (2.6 μm diameter).

The effective DNA or RNA concentration in the compartments may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qb replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Gene amplification techniques requiring thermal cycling such as PCR and LCR may be used if the emulsions and the in vitro transcription or coupled transcription-translation systems are thermostable (for example, the coupled transcription-translation systems can be made from a thermostable organism such as *Thermus aquaticus*).

Increasing the effective local nucleic acid concentration enables larger compartments to be used effectively. This allows a preferred practical upper limit to the compartment volume of about $5.2 \times 10^{-16}$ m$^3$ (corresponding to a sphere of diameter 10 μm).

The compartment size is preferably sufficiently large to accommodate all of the required components of the biochemical reactions that are needed to occur within the compartment. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per compartment ($8.33 \times 10^{-22}$ moles). In order to constitute a 2 mM solution, this number of molecules is contained within a compartment of volume $4.17 \times 10^{-19}$ litres ($4.17 \times 10^{-22}$ m$^3$ which if spherical would have a diameter of 93 nm).

Furthermore, particularly in the case of reactions involving translation, it is to be noted that the ribosomes necessary for the translation to occur are themselves approximately 20 nm in diameter. Hence, the preferred lower limit for compartments is a diameter of approximately 0.1 μm (100 nm).

Therefore, the compartment volume is preferably of the order of between $5.2 \times 10^{-22}$ m$^3$ and $5.2 \times 10^{-16}$ m$^3$ corresponding to a sphere of diameter between 0.1 μm and 10 μm, more preferably of between about $5.2 \times 10^{-19}$ m$^3$ and $6.5 \times 10^{-17}$ m$^3$ (1 μm and 5 μm). Sphere diameters of about 2.6 μm are most advantageous.

It is no coincidence that the preferred dimensions of the compartments (droplets of 2.6 μm mean diameter) closely resemble those of bacteria, for example, *Escherichia* are 1.1-1.5×2.0-6.0 μm rods and *Azotobacter* are 1.5-2.0 μm diameter ovoid cells. In its simplest form, Darwinian evolution is based on a 'one genotype one phenotype' mechanism. The concentration of a single compartmentalised gene, or genome, drops from 0.4 nM in a compartment of 2 μm diameter, to 25 pM in a compartment of 5 μm diameter. The prokaryotic transcription/translation machinery has evolved to operate in compartments of ~1-2 μm diameter, where single genes are at approximately nanomolar concentrations. A single gene, in a compartment of 2.6 μm diameter is at a concentration of 0.2 nM. This gene concentration is high enough for efficient translation. Compartmentalisation in such a volume also ensures that even if only a single molecule of the polypeptide is formed it is present at about 0.2 nM. The volume of the compartment is thus selected bearing in mind the requirements for transcription and translation of the polynucleotide.

The size of emulsion compartments may be varied simply by tailoring the emulsion conditions used to form the emulsion according to requirements of the selection system. The larger the compartment size, the larger is the volume that will be required to compartmentalise a given polynucleotide library, since the ultimately limiting factor will be the size of the compartment and thus the number of compartments possible per unit volume.

The size of the compartments is selected not only having regard to the requirements of the transcription/translation system, but also those of the selection system employed for the polynucleotide. Thus, the components of the selection system, such as a chemical modification system, may require reaction volumes and/or reagent concentrations which are not optimal for transcription/translation. Such requirements may be accommodated by a secondary re-encapsulation step. Empirical determination of optimal compartment volume and reagent concentration is preferred.

The compartment is preferably obtainable on a microfluidic scale. For example, the largest diameter of the compartment (e.g. the "Outer Diameter ($O_d$)" of FIG. 6, top-left, inset) may not be more than 100 μm. In embodiments, the largest diameter of the compartment may be from 0.1 μm to 100 μm, preferably from 0.5 μm to 10 μm, such as from 0.5 μm to 5 μm, or from 1.0 μm to 4 μm in diameter. In embodiments, the largest diameter of the compartment may be 0.8 μm. Where a plurality of compartments is concerned, these measurement values apply to the average of the largest diameter of the compartments. This can be determined by obtaining a photomicrograph of a sample containing compartments, measuring the largest diameters of each compartment in the photomicrograph multiplying by the appropriate scaling factor, and determining the average of the measurements taken.

A wide variety of compartmentalisation procedures are available (see Benita, 1996) and may be used to create the compartments used in accordance with the present invention. Indeed, more than 200 compartmentalisation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase is removed or the biological systems in it inhibited or destroyed (for example, by digestion of nucleic acids with DNase or RNase) in order that the reactions are limited to the compartments (Luisi et al., 1987).

Enzyme-catalysed biochemical reactions have also been demonstrated in compartments generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Compartments can also be generated by interfacial polymerisation and interfacial complexation (Whateley, 1996). Compartments of this sort can have rigid, nonpermeable membranes, or semipermeable membranes. Semipermeable compartments bordered by cellulose nitrate membranes, polyamide membranes and lipid-polyamide membranes can all support biochemical reactions, including multienzyme systems (Chang, 1987; Chang, 1992; Lim, 1984). Alginate/polylysine compartments (Lim & Sun, 1980), which can be formed under very mild conditions, have also proven to be very biocompatible, providing, for example, an effective method of encapsulating living cells and tissues (Chang, 1992; Sun et al., 1992).

4.1.2 Emulsions

Non-membranous compartmentalisation systems based on phase partitioning of an aqueous environment in a colloidal system, such as an emulsion, may also be used.

Preferably, the compartments of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an oil) as the matrix in which these droplets are suspended (the nondisperse, continuous or external phase). Such emulsions are termed "water-in-oil" (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (SpanTM80; ICI) and polyoxyethylenesorbitan monooleate (TweenTM80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the polynucleotides and/or the activity of the polypeptides. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994). In a preferred embodiment, emulsions are created by microfluidic processes. Most preferably, microfluidic emulsions are obtained on a droplet-by-droplet basis, one droplet being produced at a time.

Aqueous compartments formed in water-in-oil emulsions are generally stable with little if any exchange of polynucleotides or polypeptides between compartments. Additionally, biochemical reactions proceed in emulsion compartments. Moreover, complicated biochemical processes, notably gene transcription and translation are also active in emulsion compartments. The technology exists to create emulsions with volumes all the way up to industrial scales of thousands of litres (Becher, 1957; Sherman, 1968; Lissant, 1974; Lissant, 1984).

In embodiments, the compartment is a droplet of emulsion, such as a droplet of a primary emulsion (e.g. water-in-oil (w/o)). In embodiments involving emulsions, the interface between the outermost layer of dispersed (or discontinuous) phase and the continuous phase constitutes the surface of the boundary of the compartment. In embodiments, the droplet is a microfluidic droplet. Microfluidic droplets can be obtained using a microfluidic device, such as a microfluidic device on a chip. A microfluidic droplet of water in oil emulsion can be obtained on a microfluidic device, preferably a hydrophobic microfluidic device. This can be achieved by using an aqueous phase as the first phase (also referred to as the "dispersed" or "internal" phase) and a non-aqueous phase (e.g. lipophilic) as the second phase (also referred to as the "continuous" or "external" phase).

A droplet of a "double" emulsion can also be obtained on a microfluidic device. For example, a droplet of water-in-oil-in-water (w/o/w) emulsion can be obtained on a microfluidic device, preferably a hydrophilic microfluidic device. This can be achieved by using a water-in-oil emulsion as the discontinuous phase and an aqueous phase fluid as the continuous phase.

Thus, a double emulsion can be produced in two stages. First, a single emulsion is obtained (such as water-in-oil) and, secondly, the single emulsion is its self emulsified to obtain the double emulsion. The first and second stages can be carried out in tandem, for example by connecting an output from a first microfluidic device to an input of a second microfluidic device. This example is particularly advantageous because the microfluidic devices can be obtained commercially and therefore the process does not require any specialist equipment. Alternatively, the single emulsion can be collected and, optionally, stored after the first step and the second step carried out later. An arbitrary number of emulsion layers may be obtained using three, four, or more microfluidic devices operating in tandem in the manner described.

4.2 Polynucleotide

In the invention, it is desired that the compartment is formed around a polynucleotide, or that a polynucleotide is inserted into the compartment after it has been formed. The method of the present invention requires that there are only a limited number of polynucleotides per compartment. This ensures that the polypeptide of an individual polynucleotide will be isolated from other polypeptides. Thus, coupling between polynucleotide and polypeptide will be highly specific. The enrichment factor is greatest with on average one or fewer polynucleotides per compartment, the linkage between nucleic acid and the activity of the encoded polypeptide being as tight as is possible, since the polypeptide of an individual polynucleotide will be isolated from the products of all other polynucleotides. However, even if the theoretically optimal situation of, on average, a single polynucleotide or less per compartment is not used, a ratio of 5, 10, 50, 100 or 1000 or more polynucleotides per compartment may prove beneficial in sorting a large library. Subsequent rounds of sorting, including renewed encapsulation with differing polynucleotide distribution, will permit more stringent sorting of the polynucleotides. Preferably, there is a single polynucleotide, or fewer, per compartment.

The compartment may contain a single polynucleotide (i.e. a single molecule of polynucleotide). Alternatively, the compartment may contain a plurality of polynucleotides (i.e. more than one molecule of polynucleotide, e.g. two molecules of polynucleotide). Preferably, where the compartment contains a plurality of polynucleotides, all of those polynucleotides have identical, or substantially identical, polynucleotide sequence. Where a plurality of polynucleotides within a compartment have substantially identical sequence, this means that the sequence of one polynucleotide in a compartment does not differ from the sequence of another polynucleotide in the same compartment by more than is dictated by the accumulated error rate of the method used to synthesise the polynucleotides.

The number of polynucleotides in a compartment can be controlled statistically by a suitable dilution of the bulk medium containing the polynucleotide prior to the compartmentalisation step.

When the compartment is a droplet of emulsion, the polynucleotide is included in the discontinuous phase fluid prior to emulsification. The number of polynucleotides in a compartment is controlled statistically by a suitable dilution of the discontinuous phase fluid. For example, the discontinuous phase fluid may be diluted so that the average number of polynucleotides in a single droplet is not more than one. After emulsification, a discontinuous phase so diluted will form the internal volume of the emulsion droplet and each droplet thus produced will contain either 0 or 1 polynucleotides.

The polynucleotides of the invention encode a cyclic polypeptide. When expressed, a linear polypeptide may be produced from the polynucleotide. The linear polypeptide may then undergo a process of cyclisation to obtain the desired cyclic polypeptide. Cyclisation of the polypeptide may occur spontaneously, i.e. the polypeptide is self-cyclising. The sequence of amino acids in the final cyclic polypeptide may not be the same as the amino acid sequence of the linear peptide from which it is obtained. For example, the process of cyclisation may truncate one or more N-terminal residues from the linear peptide. Alternatively, the process of cyclisation may truncate one or more C-terminal residues from the linear polypeptide. In some embodiments, the process of cyclisation may truncate one or more residues from both of the N- and C-termini of the linear polypeptide.

The linear polypeptide may also be referred to as the "pre-cyclic" polypeptide. The sequence of the cyclic polypeptide may refer to the sequence of amino acids which make up the cyclic polypeptide or the sequence of amino acids comprised within the linear polypeptide that will be included in the cyclic polypeptide after cyclisation. The sequence of the cyclic polypeptide starts with the amino acid residue which was the N-terminal residue of the cyclic polypeptide sequence comprised within the linear polypeptide. In some embodiments, the sequence of the cyclic polypeptide is the same as the sequence of the linear polypeptide.

The sequence encoding the cyclic polypeptide refers to the sequence of nucleotides in the polynucleotide that encode the portion of the linear polypeptide that will be included in the cyclic polypeptide after cyclisation.

A polynucleotide is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, and magnetic or paramagnetic substances such as magnetic or paramagnetic beads. A polynucleotide may also be referred to herein as a "nucleic acid" or a "nucleic acid molecule".

The nucleic acid portion of the polynucleotide may comprise suitable regulatory sequences, such as those required for efficient expression of the polypeptide, for example promoters, enhancers, translational initiation sequences, polyadenylation sequences, splice sites and the like.

Nucleic acids molecules within the invention include those that encode a polypeptide having a first portion of a split intein, a second portion of a split intein, and a target peptide positioned in between the first portion of a split intein and the second portion of a split intein. In one embodiment of the invention, expression of the nucleic acid molecule results in a polypeptide that spontaneously splices to yield a cyclized form of the target peptide.

In another embodiment of the invention, expression of the nucleic acid molecule results in a polypeptide that is a splicing intermediate of a cyclized form of the target peptide.

The nucleic acids of the invention can be prepared according to the methods for preparing and manipulating nucleic acid molecules generally known in the art (See, e.g., Ausubel et al., Current Protocols in Molecular Biology, New York: John Wiley & Sons, 1997; Sambrook et al., Molecular Cloning: A laboratory Manual (2nd Edition), Cold Spring Harbor Press, 1989). For example, a nucleic acid molecule within the invention can be made by separately preparing a polynucleotide encoding the first portion of a split intein, a polynucleotide encoding the second portion of a split intein, and a polynucleotide encoding the target peptide. The three polynucleotides can be ligated together to form a nucleic acid molecule that encodes a polypeptide having the target peptide interposed between the first portion of a split intein and the second portion of a split intein Inteins that are not split in their natural state (i.e., those that exist as one continuous chain of amino acids) can be artificially split using known techniques. For example, two or more nucleic acid molecules encoding different portions of such inteins can be made so that their expression yields two or more artificially split intein components. See, e.g., Evans et al, J. Biol. Chem. 274:18359, 1999; Mills et al, Proc. Natl. Acad. Sci. USA 95:3543, 1998. The nucleic acids that encode such non-naturally occurring intein components (portions) can be used in the invention. Those nucleic acid molecules that encode non-naturally occurring split intein portions which efficiently interact on the same precursor polypeptide to yield cyclic peptides or splicing intermediates are preferred.

Examples of non-naturally occurring split inteins from which such nucleic acid molecules can be derived include Psp Pol-1 (Southworth, M. W., et al, The EMBO J. 17:918, 1998), *Mycobacterium tuberculosis* RecA intein, (Lew, B. M., et al, J. Biol. Chem. 273:15887, 1998; Shingledecker, K., et al, Gene 207:187, 1998; Mills, K. V., et al, Proc. Natl. Acad. Sci. USA 95:3543, 1998), Ssp DnaB/Mxe GyrA (Evans, T. C. et al, J. Biol. Chem. 274:18359, 1999), and Pfu (Otomo et al, Biochemistry 38:16040, 1999; Yamazaki et al, J. Am. Chem. Soc. 120:5591, 1998).

In embodiments, the polynucleotide may be associated with a polypeptide encoded by the polynucleotide by a bond, such as a covalent or a non-covalent bond. Examples of non-covalent bonds include ionic bonds, hydrogen bonds, and induced dipole interactions (also known as Van-der-Waals forces). In a preferred embodiment, the bond is covalent. This may be achieved by the method of mRNA display, described above. In this embodiment, the polynucleotide comprises a 3' peptidyl acceptor region, such as a puromycin moiety or an amino acid moiety. When such a polynucleotide is translated, the terminal aminoacyl transferase reaction results in a covalent bond between the nascent polypeptide and the 3' peptidyl acceptor region. In a preferred embodiment, a linker is provided comprising a 5' end that specifically hybridises to the 3' end of the polynucleotide and a 3' end that comprises a peptidyl acceptor region (or moiety).

The polynucleotide of the invention may also be modified or engineered to place specific codons in desired locations, either on the polynucleotide its self or in an mRNA encoded by the polynucleotide. This can be useful in embodiments wherein some tRNAs (those possessing the corresponding anticodon) have been loaded with non-natural, e.g. non-proteinogenic, residues, as described in more detail below (a "re-assigned codon set"). However, manipulation of the codons in the polynucleotide of the invention is not essential to the functioning of embodiments employing such non-canonical acyl-tRNAs.

4.3 Expression Vectors

The expression vectors of the present invention can be prepared by inserting polynucleotides encoding a target peptide into any suitable expression vector that can facilitate expression of the polynucleotide. Such suitable vectors include plasmids, bacteriophages, and viral vectors. A large number of these are known in the art, and many are commercially available or obtainable from the scientific community. Those of skill in the art can select suitable vectors for use in a particular application based upon, e.g., the type of system selected (e.g., in vitro systems, prokaryotic cells such as bacteria, and eukaryotic cells such as yeast or mammalian cells) and the expression conditions selected.

Expression vectors within the invention can include a stretch of nucleotides that encodes a target polypeptide and a stretch of nucleotides that operate as a regulatory domain that modulates or controls expression (e.g., transcription) of nucleotide sequences within the vector. For example, the regulatory domain can be a promoter or an enhancer.

Expression vectors within the invention can include nucleotide sequences that encode a peptide that facilitates screening of the cyclized form of the target peptide or splicing intermediate for a particular characteristic (e.g., a DNA-binding domain, an affinity tag such as a chitin-binding domain or a biotin tag; a coloured or light-emitting label; a radioactive tag; etc.), or purifying the cyclized form of the target peptide or splicing intermediate (e.g., an affinity tag such as a chitin-binding domain, a biotin tag, a coloured or light-emitting label; a radioactive tag; etc.).

In preferred embodiments, the expression vectors within the invention are produced with restriction sites both between and within the nucleic acid sequences that encode the split intein portions to enable the cloning of a wide variety of cyclization targets or splicing intermediates. In some embodiments, an expression vector of the invention can be an inducible expression vector, such as an arabinose inducible vector. The inducer may be capable of permeating the compartment material of the invention.

4.4 Polypeptide

Several methods of polypeptide cyclisation are known in the art. Polypeptide cyclisation can be carried out between two side chains, between a side chain and a terminal group (i.e. N- or C-terminal), or between two terminal groups (i.e. "head to tail" or "backbone" cyclisation). One such method of side chain to side chain cyclisation can be carried out enzymatically. There are many enzymes that would cyclize a peptide sequence. For example, transglutaminase can catalyse an aminotransferase reaction between a glutamine side chain and a lysine side chain resulting in a covalent isopeptide bond between the two side chains. If the glutamine and lysine are on the same polypeptide, that polypeptide is cyclised by this reaction. Backbone cyclisation can similarly be brought about enzymatically, for example by treatment with subtilisin. Other non-limiting examples are ProcM and PatG. Typically, these methods rely on the presence of a "leader" sequence of amino acids in the polypeptide. A leader sequence recruits and directs the action of its cognate enzyme by specifically interacting with the enzyme. Each enzyme may be specific for a particular leader sequence. A leader sequence for a particular enzyme may be added to a polypeptide of the invention through manipulation of its encoding polynucleotide, for example by conventional molecular cloning techniques, which are within the purview of the person skilled in the art.

Methods of macrocyclisation are discussed at length by Bashiruddin and Suga, Curr. Op. in Chem. Bio., vol. 24, pp. 131-138, in particular, in the context of mRNA display, though one skilled in the art will be familiar with the use of these methods outside of mRNA display technology. To synthesize macrocyclic peptides using the translation machinery, the most basic approach is through disulphide bonds between cysteine residues. However, their susceptibility to reduction in intracellular environments makes them undesirable for some applications. Therefore, methods of forming a non-reducible covalent bond for cyclization through simple chemical post-translational modifications have been devised. Methods of bridging two primary amines between the N-terminus and a lysine sidechain using disuccinimidyl glutarate or the sulfhydryl group of two cysteine residues using dibromoxylene have been used to successfully generate macrocyclic peptides. A similar method of producing bicyclic peptides via thioether-crosslinking of three cysteine residues has been also reported (Heinis & Winter, Nat Chem Biol, 5 (2009), pp. 502-507). An advantage of these methods is their applicability to the standard proteinogenic amino acids. However, when more than two reactive residues appear in the random regions of these libraries, the crosslinking patterns can become scrambled potentially causing difficulty in deconvoluting the outcome of selections based on such cyclization methods.

A technically more demanding method than the above, but far more reliable for the construction of macrocyclic peptides, is based on the concept of manipulating the genetic code, known as genetic code reprogramming, where designated codons are made vacant and then reassigned to nonproteinogenic amino acids. Two major methodologies have been reported to date, both of which utilize custom-made reconstituted translation systems.

One method takes advantage of the mischarging properties of aminoacyl-tRNA synthetases in the presence of excess amounts of nonproteinogenic amino acids, yielding the corresponding aminoacyl-tRNAs. Szostak et al. reported a method of generating peptides containing 4-selenalysine in the peptide chain followed by the selective oxidation and concomitant elimination of the seleno group to yield a dehydroalanine residue. Dehydroalanine then reacts with the sulfhydryl group of cysteine via Michael addition to form a thioether bond, giving rise to lanthionine-like macrocyclic peptides.

The other method involves 'flexible' tRNA acylation ribozymes, known as flexizymes, developed by Suga et al., which facilitate the preparation of a wide array of nonproteinogenic aminoacyl tRNAs with nearly unlimited choice. The combination of a custom-made in vitro translation system with flexizymes, referred to as the FIT (Flexible In vitro Translation) system, allows the ribosomal synthesis of macrocyclic peptides using nonproteinogenic amino acids capable of crosslinking with other proteinogenic or nonproteinogenic residues. The FIT system allows for a wide variety of cyclization methods, for instance, methyllanthionine-like macrocyclic peptides can be synthesized through the incorporation of vinylglycine which is thermally isomerized to dehydrobutyrine which can then form a thioether bond with cysteine residues (Y. Goto, K. Iwasaki, K. Torikai, H. Murakami, H. Suga; Chem Commun (Camb), 23 (2009), pp. 3419-3421). Translation of peptides containing a benzylamine group designated by the N-terminal initiating amino acid and a downstream 5-hydroxytryptophan is a unique method of mild oxidative macrocyclisation forming a fluorogenic indole linkage (Y. Yamagishi, H. Ashigai, Y. Goto, H. Murakami, H. Suga; ChemBioChem, 10 (2009), pp. 1469-1472). Moreover, ribosomal synthesis of head-to-tail linked peptides can also be produced through the C-terminal Cys-Pro-HOG (glycolic acid) sequence or programmed peptidyl-tRNA drop-off containing the C-terminal Cys-Pro sequence (T. Kawakami, Nat Chem Biol, 5 (2009), pp. 888-890; Y. Ohshiro, ChemBioChem, 12 (2011), pp. 1183-1187; T. J. Kang, Angew Chem Int Ed Engl, 50 (2011), pp. 2159-2161). In both cases, the C-terminal ester bond accelerates the self-rearrangement of N→S migration to form a C-terminal diketopiperadine-thioester, eventually yielding backbone-cyclized monocyclic or disulphide-bridged bicyclic peptides.

The most convenient and reliable method of cyclization has been through the translation of peptides with an N-chloroacetyl-amino acid initiator that can react with a downstream cysteine (Y. Goto, A. Ohta, Y. Sako, Y. Yamagishi, H. Murakami, H. Suga; ACS Chem Biol, 3 (2008), pp. 120-129). The advantage of this method is the spontaneous and selective thioether bond formation between the N-terminal chloroacetyl group and the sulfhydryl group of the closest cysteine residue. A single exception is that a cysteine residue adjacent to the N-chloroacetyl-amino acid cannot react with the chloroacetyl group due to ring constraint, thus leaving a free sulfhydryl group at this position. However, this selectivity turns out be a convenient way to translate fused-bicyclic peptides, having a thioether (sulphide) bond between the N-terminus and the second cysteine and a disulphide bond between the first and third cysteine residues. Importantly, it has been demonstrated that the FIT system facilitates the translation of peptides containing D-amino acids, N-methyl-amino acids, N-alkylglycines, and those with noncanonical sidechains.

In other methods, polypeptide cyclisation can be achieved spontaneously by intramolecular interactions within the polypeptide. Such can be achieved, for example, by the fusion of sequences derived from "inteins" to the desired cyclic polypeptide.

Numerous methods of making nucleic acids encoding peptides of a known or random sequence are known in art. For example, polynucleotides having a predetermined or a random sequence can be prepared chemically by solid phase synthesis using commercially available equipment and reagents. Polymerase chain reaction can also be used to prepare polynucleotides of known or random sequences. See, e.g., Ausubel et al, supra. As another example, restriction endonucleases can be used to enzymatically digest a larger nucleic acid molecule or even whole chromosomal DNA into a plurality of smaller polynucleotide fragments that can be used to prepare nucleic acid molecules of the invention.

Polynucleotides that encode peptide sequences to be cyclized are preferably prepared so that one terminus of the polynucleotide encodes an asparagine, serine, cysteine, or threonine residue to facilitate the cyclization reaction. For the same reason polynucleotides that encode peptide sequences for production of splicing intermediates are preferably prepared so that the terminus encodes an amino acid other than an asparagine, serine, cysteine, or threonine residue so that the cyclization reaction is prevented.

Once generated, conventional methods can be used to ligate nucleic acid molecules encoding intein portions to a nucleic acid molecule encoding a target peptide (or peptide within a splicing intermediate) to form a larger nucleic acid molecule encoding a polypeptide having the first intein portion-target peptide-second intein portion order. See, e.g., Ausubel et al, supra.

4.4.1 SICLOPPS

The trans-splicing ability of split inteins has been exploited to develop a general method of producing cyclic peptides and splicing intermediates displaying peptides in a looped conformation (PCT/US1999/030162). In this method, a target peptide is interposed between two portions of a split intein in a precursor polypeptide. The two portions of the split intein physically come together to form an active intein in a conformation that also forces the target peptide into a loop configuration. In this configuration, the ester isomer of the amino acid at the junction between one of the intein portions (e.g., $I_N$) and the target peptide is stabilized such that heteroatom from the other portion of the intein (e.g., $I_C$) can then react with the ester to form a cyclic ester intermediate. The active intein then catalyses the formation of an aminosuccinimide that liberates a cyclized form of the target peptide (i.e., a lactone form), which then spontaneously rearranges to form the thermodynamically favoured backbone cyclic peptide product (i.e., the lactam form).

By arresting the reaction at given points before liberation of the cyclic peptide, splicing intermediates bearing the target peptide in a loop configuration can be produced. To produce such peptides, nucleic acid molecules encoding a polypeptide having the target peptide sequence interposed between the two intein portions can be constructed. Introduction of these constructs into an expression vector provides a method for producing the polypeptide in an appropriate expression system, where the polypeptide can be spliced into a cyclic peptide or a splicing intermediate. Using this method, several different cyclic peptides or splicing intermediates can be prepared to generate a library of cyclized or partially-cyclized peptides that can be screened for particular characteristics.

An intein is a segment of a protein that is able to excise itself and join the remaining portions (the exteins) with a peptide bond in a process termed "protein splicing". Intein-mediated protein splicing occurs after the intein-containing mRNA has been translated into a protein. This precursor protein contains three segments: an N-extein followed by the intein followed by a C-extein. After splicing has taken place, the resulting protein contains the N-extein linked to the C-extein. Sometimes, the intein of the precursor protein comes from two genes. In this case, the intein is said to be a split intein. The intein portion (or fragment) encoded by one gene interacts with the intein fragment encoded by the other gene to yield a catalytically active intein, which proceeds to excise its self and to splice together the exteins from the two genes.

If the two split intein fragments are instead positioned on opposite ends of an intervening polypeptide sequence, the process of splicing and excision produces a cyclic polypeptide with the sequence of the original intervening polypeptide. This can be achieved by conventional molecular genetics techniques, for example by cloning the sequences encoding two complementary split intein fragments into a vector with a sequence encoding the desired cyclic polypeptide. The three polynucleotide sequences are arranged in the vector so that upon expression a polypeptide is obtained having an N-terminal intein fragment, followed by the cyclic polypeptide sequence, followed by a C-terminal intein fragment, the N- and C-terminal intein fragments being capable of associating to form a functional intein that subsequently catalyses the splicing reaction that produces the cyclic polypeptide. In other words, the polynucleotide comprises a sequence encoding the N-terminal intein fragment, followed by a sequence encoding the cyclic polypeptide sequence, followed by a sequence encoding the C-terminal intein fragment. This process is known as Split-Intein Circular Ligation Of Peptides and Proteins (SICLOPPS).

Expression from a polynucleotide can be the expression of a polypeptide from a polynucleotide. Expression from a polynucleotide may also be the expression of a second polynucleotide from a first polynucleotide. For example, an RNA polynucleotide can be expressed from a DNA polynucleotide by the process of transcription by a suitable RNA polymerase. A polypeptide may be expressed from an RNA polynucleotide by the process of translation by a suitable ribosome. In some usages, expression from a polynucleotide refers to the ultimate expression of a polypeptide from its encoding genetic material, i.e. both the transcription to RNA and translation to polypeptide. The intended usage will be clear from the context.

One suitable split intein is the Npu split intein from dnaE. An example of a polypeptide according to the present invention comprising the Npu split intein may have the following sequence:

(SEQ ID NO: 1)
HHHHHHGENLYFKLQAMGMIKIATRKYLGKQNVYDIGVERYHNFALKNGF

IASNX~~~~~CLSYDTEILTVEYGILPIGKIVEKRIECTVYSVDNNGNIY

TQPVAQWHDRGEQEVFEYCLEDGCLIRATKDHKFMTVDGQMMPIDEIFER

ELDLMRVDNLPNGTAANDENYALAA

Wherein X~~~~~ is the cyclic peptide produced; X is C, S, T or any other amino acid, and "~" denotes an amino acid of the cyclic peptide sequence. It will be apparent to one skilled in the art that any sequence may be inserted after "X" in the sequence above. The sequence may be one or more amino acids in length, in embodiments at least three or more amino acids in length, preferably at least six amino acids in length.

The above sequence comprises the following constituents:

(SEQ ID NO: 2)
HHHHHH

An optional hexahistidine tag to assist in purification, for example on a Nickle-NTA column. Other purification systems are envisaged, such as "FLAG-TAG", in which case hexahistidine is replaced with the appropriate tag sequence.

(SEQ ID NO: 3)
GENLYFKLQAMGMIKIATRKYLGKQNVYDIGVERYHNFALKNGFIASN

Containing the C-terminal intein fragment.

X~~~~

The cyclic polypeptide sequence.

(SEQ ID NO: 4)
CLSYDTEILTVEYGILPIGKIVEKRIECTVYSVDNNGNIYTQPVAQWHDR

GEQEVFEYCLEDGCLIRATKDHKFMTVDGQMMPIDEIFERELDLMRVDNL

PNGTAANDENYALAA containing the N-terminal intein fragment.

4.5 Modifying Compartment Contents 4.5.1 In Vitro Transcription and Translation

In order to co-compartmentalise the cyclic polypeptide with its encoding polynucleotide, means for expressing the polypeptide from the polynucleotide may also be enclosed within the compartment. Such means may include an in vitro transcription and translation (IVTT) system. An IVTT system may include, for example, an RNA polymerase, a ribosome, nucleotide phosphates, amino acid-loaded tRNAs, and translation factors, such as initiation and elongation factors. Suitable in vitro transcription/translation reagents are well known in the art (e.g. Isalan, M. et al (2005) PLoS Biol. 3 e64). Expression of the polynucleotide within the compartment therefore co-locates the polypeptide and polynucleotide. When the compartment is a droplet of emulsion, this can be achieved by including the IVTT components in the discontinuous (or dispersed, or internal) phase fluid prior to emulsification.

Further, acylated tRNAs preliminarily charged with a desired non-proteinogenic amino acid (or hydroxy acid) (i.e., having an activated amino acid attached thereto) can be added to a reconstituted cell-free translation (IVTT) system containing only limited natural amino acids. By correlating the codons for excluded natural amino acids with the anticodon of the tRNA acylated with a non-proteinogenic amino acid (or hydroxy acid), a peptide containing the non-proteinogenic amino acid (or hydroxy acid) can be synthesized by translation on a ribosome on the basis of genetic information of the mRNA encoded by or constituting the polynucleotide of the invention. Alternatively, a peptide containing no natural amino acid can also be synthesized by translation by adding only acylated tRNAs charged with non-proteinogenic amino acids (or hydroxy acid) to a reconstituted cell-free translation system containing no natural amino acid.

Acylated tRNAs charged with a non-proteinogenic amino acid (or hydroxy acid) can be prepared by using the artificial RNA catalysts "flexizymes" capable of catalysing aminoacyl-tRNA synthesis. As indicated above, these artificial RNA catalysts are capable of charging an amino acid having any side chain and also have the function of recognizing only a consensus sequence 5'-RCC-3' (R=A or G) at the 3' end of tRNAs to acylate the 3' end of the tRNAs, and therefore, they can act on any tRNAs having different anticodons. Moreover, flexizymes can charge tRNAs with not only L-amino acids but also hydroxy acids (having a hydroxyl group at the α-position), N-methylamino acids (having an N-methylamino acid at the α-position), N-acylamino acids (having an N-acylamino group at the α-position), D-amino acids and the like. Detailed description can be found in Y. Goto, H. Suga (2009) "Translation initiation with initiator tRNA charged with exotic peptides" Journal of the American Chemical Society, Vol. 131, No. 14, 5040-5041, WO2008/059823 entitled by "TRANSLATION AND SYNTHESIS OF POLYPEPTIDE HAVING NONNATIVE STRUCTURE AT N-TERMINUS AND APPLICATION THEREOF", Goto et al., ACS Chem. Biol., 2008, 3, 120-129, WO2008/117833 entitled by "PROCESS FOR SYNTHESIZING CYCLIC PEPTIDE COMPOUND", etc., the entire contents of which are incorporated herein by reference.

Other non-natural amino acids that can be ligated to a tRNA by flexizyme include amino acids having various side chains, β (beta)-amino acids, γ (gamma)-amino acids and δ (delta)-amino acids, D-amino acids, and derivatives having a structure in which an amino group or a carboxyl group on the amino acid backbone is substituted. Further, unusual peptides obtained by incorporating non-natural amino acids may have a backbone structure other than normal amide bonds. For example, unusual peptides also include depsipeptides consisting of amino and hydroxy acids, polyesters produced by continuous condensation of hydroxy acids, peptides methylated at the nitrogen atom of the amide bond by introducing an N-methylamino acid, and peptides having various acyl groups (acetyl, pyroglutamic acid, fatty acids, etc.) at the N-terminus. Furthermore, cyclic peptides obtained by circularizing non-cyclic peptides consisting of an amino acid sequence bearing a pair of functional groups capable of forming a bond between them at opposite ends can also be synthesized (or cyclic N-methylpeptides can be obtained if N-methylpeptides are used). Circularization may occur under the conditions of cell-free translation (IVTT) systems with a pair of some functional groups, as exemplified by a cyclic peptide circularized via a thioether bond obtained by translation/synthesis of a peptide sequence bearing a chloroacetyl group and a cysteine group at opposite ends.

4.5.2 Polynucleotide Amplification

It can be difficult to produce enough polypeptide from a single polynucleotide to obtain a detectable signal in a subsequent assay. In embodiments, multiple copies of the polynucleotide are produced within the compartment. This can be achieved by a process of amplification, such as through the Polymerase Chain Reaction (PCR), or through the use of a Phi29 polymerase. If the components of the amplification process are contained within the compartment along with the polynucleotide, amplification can be carried out by subjecting the compartment to the necessary amplification conditions, such as thermal cycling or incubation under heating. The compartment therefore becomes a self-contained micro-reactor, in an analogous manner to that described above with respect to transcription and translation of the polynucleotide. Because the compartment forms a barrier to the movement of polynucleotides, all of the copies of the amplified polynucleotide are contained and isolated within this compartment. The compartment thus becomes a monoclonal unit, i.e. a co-localised unit of identical, or substantially identical, copies of the polynucleotide.

When the compartment is a droplet of emulsion, this is achieved by including the components of the amplification reaction in the discontinuous phase fluid prior to emulsification. The emulsion may then be subjected to the conditions necessary for amplification to the desired number of copies.

The primers for PCR can be selected or designed to amplify the whole of the desired sequence of the polynucleotide (the "amplicon"). For example, one primer can be designed to anneal to the beginning of the desired sequence on the template strand and a second primer can be designed to anneal to the beginning of the desired sequence on the coding strand.

When the polynucleotide encodes a SICLOPPS self-splicing polypeptide, for example, the first primer may anneal to the sequence encoding the N-terminal intein fragment on the template (or antisense) strand and the second primer may anneal to the sequence encoding the C-terminal intein fragment on the coding (or sense) strand.

Alternatively, the vector may be selected or designed to contain specific sequences for annealing primers. For example, a sequence complementary to the first primer may be inserted after the desired sequence on the template strand of the vector (i.e. after the 3' end of the desired sequence on the template strand) and a sequence complementary to the second primer may be inserted after the desired sequence on the coding strand of the vector (i.e. after the 3' end of the desired sequence on the coding strand). This option is particularly suitable when the desired sequence to be amplified is unknown, such as when inserting randomised polynucleotides into vectors for the construction of a genetic library. In this case, the primers can be selected or designed to produce polypeptide sequences, upon translation of the amplified polynucleotide, which have particular properties. For example, one primer could be designed to encode the N-terminal glutamine donor sequence Ala-Leu-Gln and the second primer could be designed to encode a C-terminal region lysine as a substrate for transglutaminase.

Preferably, the amplification reagents are isothermal amplification reagents. Techniques for isothermal amplification in agarose gels are well known in the art and include multiply-primed RCA with the Phi29 DNA polymerase, which produces a high molecular weight (>40 kb) and hyperbranched products containing amplified copies of the polynucleotide. (Michikawa, Y. et al. (2008). Anal. Biochem., 383, 151-158). Amplified DNA, especially hyperbranched amplified DNA, is unable diffuse out of the bead matrix.

When the polynucleotide and the encoded product remain co-localised without compartmentalisation, the beads may be contacted with the aqueous expression solution without emulsification. The ability of the polynucleotide and the encoded product to remain co-localised depends on the concentrations and biophysical properties (e.g. size) of the encoded product.

In embodiments, the polynucleotide is amplified by the Phi29 DNA polymerase. In these embodiments, the primers may be random primers, such as polynucleotide hexamers with a random sequence of 6 nucleotides. Alternatively, the primers may be designed or selected in a similar manner as described for PCR above. An advantage of amplification by a Phi29 system is that thermal cycling is not necessary; amplification can be carried out by Phi29 by simple incubation of the reaction mixture.

In embodiments, Phi29 amplification is carried out by incubating the compartment for 1 hour or more. Preferably, amplification is carried out for 8 hours or more. Most preferably, amplification is carried out for 16 hours or more. Incubation of the Phi29 amplification reaction may also be carried out for 1, 2, or 3 days, or more.

In embodiments, incubation of Phi29 amplification may be carried out under ambient conditions. Alternatively, Phi29 amplification may be incubated under heating of from 20 C to 50 C, most preferably from 30 C to 40 C, for example at 37 C.

However, the conditions necessary to carry out the amplification reaction can be incompatible with IVTT. Therefore, in order to carry out IVTT on amplified polynucleotides within a compartment, it is sometimes necessary to manipulate the compartment to change the internal environment after amplification has been completed. Methods in the art, such as that of Brouzes et al. (PNAS, 2009, 106:34, pp. 14195-14200), change the conditions within a microfluidic droplet by the process of droplet merging. However, droplet merging is a technically challenging process, requiring specialist equipment and expertise to carry out with any degree of reliability.

4.5.3 Gel Transfer

In embodiments, the invention circumvents the drawbacks associated with droplet merging by employing a gel-forming material within the compartments, in the manner of WO 2012/156744 A2. The gel-forming material can be made to undergo a reversible transition from a liquid phase to a solid or gel phase to immobilise the amplified polynucleotide. When the gel solidifies in the compartment it may form a bead containing the immobilised polynucleotide. The compartment may then be disrupted without affecting the monoclonal integrity of the amplified polynucleotides trapped in the gel.

The process of disrupting the compartment will differ depending on the compartment material used. In some embodiments, a deemulsification agent, for example a weak surfactant, may be added to the emulsion to separate the phases and the aqueous phase containing the beads removed. The deemulsification agent competes with the surfactant at the oil/water interface and causes it to collapse; this is also known as "breaking the emulsion". Suitable weak surfactants include perfluorooctanol (PFO) and other fluorous compounds with a small hydrophilic group, if fluorinated oil is used, or a buffer containing SDS and Triton and other compounds with a carbon chain on one side and a small hydrophilic group on the other, if mineral oil is used. The deemulsification agent may be added to the emulsion and the mixture agitated, for example with a pipette.

In other embodiments, the emulsion may be centrifuged to separate the phases and the aqueous phase containing the beads removed. Suitable techniques for the re-emulsification of gel beads are known in the art (Abate, A. R. et al (2009) Lab Chip, 9, 2628-2631).

Following de-emulsification, the beads may be isolated and/or washed to remove buffers and other reagents. Beads may be isolated and/or washed by centrifugation or filtering using standard techniques.

Following washing, the beads may be immediately subjected to further steps in the methods described herein or may be stored, for example at room temperature or by refrigeration or freezing (preferably in the presence of glycerol). In embodiments, in which the beads contain viable cells, the beads may be treated with a preservative such as glycerol before freezing in accordance with known techniques.

The decompartmentalised gel bead is porous and the internal conditions of the gel can be changed by suspending it in different media. The bead may therefore be removed from conditions for carrying out PCR and transferred to conditions suitable for carrying out IVTT without loss of monoclonality. The environment within the bead will then be suitable for IVTT of the polynucleotide.

The gel forming agent is an agent, for example a polymer such as polysaccharide or polypeptide, which can be solidified from a liquid into a gel, for example by alteration of conditions, such as heating, cooling, or altering pH.

Suitable gel forming agents include alginate, gelatine, and agarose and other gels having a sol phase sufficiently fluid to move through the channels of a microfluidic device. Preferably agarose, which is a linear polymer made up of the repeating units of a disaccharide (D-galactose and 3,6-anhydro-L-galactopyranose), is employed. The gel-forming agent may be solidified into a bead by any convenient method, for example by changing the conditions. Preferably, the hydrogel-forming agent is solidified by altering the temperature, for example by cooling. Hyaluronic-acid is another gel-forming agent that may be used with the invention.

In a preferred embodiment, the gel may be induced to undergo a phase change from its liquid form to its solid form by cooling it to below its phase-change (or transition) temperature. For example, when the agent is agarose, it may be solidified by reducing the temperature, for example below 25° C., below 20° C. or below 15° C. The precise gelling temperature is dependent on the type of agarose and its concentration and may be easily determined by the skilled person. For example, 0.5% to 2% of ultra-low melting point agarose Type IX-A (Sigma) has a gelling point of about 17° C.

Solidification of the agent within the compartment moulds the solidified gel into a bead. The population of solidified beads may be monodisperse. The encoded product may be retained in the beads by any convenient method. For example, the product may be retained in the beads through entrapment within the gel matrix or through covalent or non-covalent binding to a retention agent or the gel matrix itself.

Molecules, such as polypeptides and polynucleotides, may be retained in the beads by virtue of their size. For example, molecules greater than a threshold size may be unable to diffuse out of the bead through pores in the gel and may therefore be trapped within the gel matrix of the bead. For example, polynucleotides, such as plasmids and amplified copies of a polynucleotide, may be retained in the bead. In some embodiments, the gel may retain particles having a diameter of 50 nm or more, although the precise threshold depends on multiple factors, including the type of gel and its concentration.

In some embodiments, an aqueous solution in which a gel bead is solidified following emulsification, for example a solution comprising a hydrogel-forming agent, such as the aqueous expression and/or amplification solution described above, may further comprise one or more retention agents to reduce or prevent the diffusion of polynucleotide or encoded products from the bead, for example by binding to polynucleotides or encoded products.

In other embodiments, compartment components such as substrates and encoded product may be retained by direct binding the hydrogel scaffold. For example, the scaffold may be engineered to contain one or more binding sites which bind to the droplet components and retain them in the bead.

In other embodiments, polynucleotides and/or encoded products may be sufficiently retained in the bead without the need for binding to retention agents or the gel scaffold.

The gel-forming agent may be incorporated into the compartment at any stage prior to disrupting the compartment.

4.6 Libraries

A library of genetically tagged cyclic peptides in compartments may be produced. Randomised polynucleotides of a desired length may be cloned into vectors for amplification and expression, before compartmentalisation of the vectors in single copy, for example by the methods described above. For example, the vector depicted in FIG. 15 has a section labelled "library", this is the location of the randomised polynucleotide in this embodiment.

The length of the randomised polynucleotide inserted into the vector will be dependent on various factors that may be determined by the skilled person. Of primary consideration is the size of the ultimate polypeptide expressed. In a preferred embodiment, the polypeptide is 6 amino acids in length. A suitable randomised polynucleotide would therefore be 18 nucleic acids in length. For cyclic peptide formation, consideration must be given to whether the length of the polypeptide is sufficient to allow the cyclisation reaction to proceed, i.e. whether the length allows a closed peptide cycle to form. In embodiments, the peptide is cyclised by a linker of any length. Therefore, cyclic polypeptides may be achieved by encoding just two amino acids, in which case the randomised polynucleotide will be at least 6 nucleic acids in length. Another consideration is the maximum insert size tolerated by the vector and corresponding replication system. In embodiments, the randomised sequence may be longer, for example, at least 9, 30, 60, 90, 180, 300, 600, 900, 1,800, 3,000, or more nucleic acids in length. In preferred embodiments, the randomised nucleotide sequence is 6, 9, 12, 15, 18, 21, 24, 27, or 30 nucleotides in length. Although the randomised sequence is intended to encode a polypeptide, its length may not necessarily be a multiple of 3. For example, it may be 7, 8, 10, 11, 13, 14, 16, 17, 19, 20, 22, 23, 25, 26, 28, or 29 nucleotides in length. The randomised polynucleotide sequence may also be referred to herein as the variable sequence. In embodiments, one or more positions of the "random" or "variable" sequence may actually be fixed. For example, in embodiments achieving cyclisation by the SICLOPPS method, the first position may be occupied by an invariant cysteine, serine, or threonine residue, followed by a variable or random amino acid sequence.

It will also be appreciated that a library of the present invention may contain members with randomised sequences of different lengths. For example, a proportion of library members may comprise a randomised sequence of 9 nucleotides in length, and another proportion of members of the same library may comprise a randomised sequence of 19 nucleotides in length. Any number of different lengths may be present in the same library.

Each individual compartment may then serve as a microreactor for amplification, e.g. by including the components for Phi29 amplification in the vector medium prior to compartmentalisation. In embodiments utilising a gel, the compartments are subjected to conditions which cause the gel to solidify, at which point the compartments may be disrupted and the media conditions changed for IVTT. The gel beads are optionally re-compartmentalised and each bead now serves as a micro-reactor for IVTT of their immobilised polynucleotide. The library is therefore obtained. At the same time as or following IVTT, some or all of the components required to carry out the selection protocol may be introduced to the bead and/or capsule.

The integrity of the association between polypeptide and encoding polynucleotide may be further strengthened by employing the mRNA display technology described above in the compartments and gel transfer protocols of the present invention. In this embodiment, the polynucleotide is structured so that it is linked to the resulting polypeptide by the process of translation. For example, the 3' end of the polynucleotide may comprise a peptidyl acceptor region, such as a puromycin moiety or an amino acid moiety.

It will be appreciated that the display technologies described herein (e.g. mRNA display, phage display, compartmentalised randomised polynucleotides) are not necessarily mutually exclusive and may be implemented together within the same embodiment. For example, a polynucleotide of the invention may encode a SICLOPPS polypeptide whilst also comprising a peptidyl acceptor region which forms a covalent bond to the nascent peptide at the termination of translation of the polynucleotide.

Furthermore, compartmentalisation of an mRNA library by any of the methods described herein allows functional assays to be performed on mRNA libraries, thus overcoming one of the major drawbacks of the mRNA display technology.

4.7 Selection

A library according to the present invention may be screened by subjecting it to the conditions of an assay, each bead or compartment thus taking on the properties of a positive or a negative result of the assay, as the case may be. Beads or compartments may then be selected based on this property. For example, a fluorescent signal can be selected for by FACS/FADS.

All reporters, labels, and tags disclosed herein may be used in any embodiment disclosed herein.

4.7.1 Affinity Selection

In the case of selection for a polypeptide with affinity for a specific ligand the polynucleotide may be linked to the polypeptide in the microcapsule via the ligand. For example, the ligand may be covalently linked to the polynucleotide, such as through a reaction between the ligand and the 3'-OH or 5'-phosphate of the polynucleotide. As used herein, "ligand" may refer to any entity which binds to another entity or may be bound by another entity. For example, the ligand may be another polypeptide comprising a receptor binding site. In this format, peptides of the invention are selected on the basis of the strength of their interaction with the ligand polypeptide, ideally via said receptor binding site. Alternatively, the ligand may be a small molecule, further polynucleotide (e.g. an aptamer), or a macro-scale physical structure such as a polystyrene bead or a magnetic bead. These examples are not intended to be limiting.

Only polypeptides with affinity for the ligand will bind to the polynucleotide and only those polynucleotides with polypeptide bound via the ligand will acquire the changed optical properties which enable them to be retained in the selection step. In this embodiment, the polynucleotide will thus comprise a nucleic acid encoding the polypeptide linked to a ligand for the polypeptide.

The change in optical properties of the polynucleotide after binding of the polypeptide to the ligand may be induced in a variety of ways, including:

(1) the polypeptide itself may have distinctive optical properties, for example, it is fluorescent (e.g. green fluorescent protein, (Lorenz et al., 1991)).

(2) the optical properties of the polypeptide may be modified on binding to the ligand, for example, the fluorescence of the polypeptide is quenched or enhanced on binding (Guixe et al., 1998; Qi and Grabowski, 1998)

(3) the optical properties of the ligand may be modified on binding of the polypeptide, for example, the fluorescence of the ligand is quenched or enhanced on binding (Voss, 1993; Masui and Kuramitsu, 1998).

(4) the optical properties of both ligand and polypeptide are modified on binding, for example, there can be a fluorescence resonance energy transfer (FRET) from ligand to polypeptide (or vice versa) resulting in emission at the "acceptor" emission wavelength when excitation is at the "donor" absorption wavelength (Heim & Tsien, 1996; Mahajan et al., 1998; Miyawaki et al., 1997).

In this embodiment, it is not necessary for binding of the polypeptide to the polynucleotide via the ligand to directly induce a change in optical properties. All the polypeptides to be selected can contain a putative binding domain, which is to be selected for, and a common feature—a tag. The polynucleotide in each microcapsule is physically linked to the ligand. If the polypeptide produced from the polynucleotide has affinity for the ligand, it will bind to it and become physically linked to the same polynucleotide that encoded it, resulting in the polynucleotide being 'tagged'.

At the end of the reaction, all of the microcapsules may be combined, and all polynucleotides and polypeptides pooled together in one environment. Polynucleotides encoding polypeptides exhibiting the desired binding can be selected by adding reagents which specifically bind to, or react specifically with, the "tag" and thereby induce a change in the optical properties of the polynucleotide allowing their sorting. For example, a fluorescently-labelled anti-"tag" antibody can be used, or an anti-"tag" antibody followed by a second fluorescently labelled antibody which binds the first.

In an alternative embodiment, polynucleotides may be sorted on the basis that the polypeptide, which binds to the ligand, merely hides the ligand from, for example, further binding partners which would otherwise modify the optical properties of the polynucleotide. In this case polynucleotides with unmodified optical properties would be selected.

In an alternative embodiment, the invention provides a method wherein the polypeptides bind to polynucleotides encoding them. The polypeptides together with the attached polynucleotides are then sorted as a result of binding of a ligand to polypeptides having the desired binding activity. For example, all polypeptides can contain an invariant region which binds covalently or non-covalently to the polynucleotide, and a second region which is diversified so as to generate the desired binding activity.

In an alternative embodiment, the ligand for the polypeptide is itself encoded by the polynucleotide and binds to the polynucleotide. Stated otherwise, the polynucleotide encodes two (or indeed more) polypeptides, at least one of which binds to the polynucleotide, and which can potentially bind each other. Only when the polypeptides interact in a compartment is the polynucleotide modified in a way that ultimately results in a change in its optical properties that enables it to be sorted. This embodiment, for example, is used to search gene libraries for pairs of genes encoding pairs of proteins which bind each other. Individual polypeptides may also be encoded by individual polynucleotides.

Fluorescence may be enhanced by the use of Tyramide Signal Amplification (TSA™) amplification to make the polynucleotides fluorescent. This involves peroxidase (linked to another protein) binding to the polynucleotides and catalysing the conversion of fluorescein-tyramine in to a free radical form which then reacts (locally) with the polynucleotides. Methods for performing TSA are known in the art, and kits are available commercially from NEN.

TSA may be configured such that it results in a direct increase in the fluorescence of the polynucleotide, or such that a ligand is attached to the polynucleotide which is bound by a second fluorescent molecule, or a sequence of molecules, one or more of which is fluorescent.

4.7.2 Catalysis Selection

When selection is for catalysis, the polynucleotide in each microcapsule may comprise the substrate of the reaction. If the polynucleotide encodes a polypeptide capable of acting as a catalyst, the polypeptide will catalyse the conversion of the substrate into the product. Therefore, at the end of the reaction the polynucleotide is physically linked to the product of the catalysed reaction.

It may also be desirable, in some cases, for the substrate not to be a component of the polynucleotide. In this case the substrate would contain an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" is then activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

The optical properties of polynucleotides with product attached and which encode polypeptides with the desired catalytic activity can be modified by either:

(1) the product-polynucleotide complex having characteristic optical properties not found in the substrate-polynucleotide complex, due to, for example;
  (a) the substrate and product having different optical properties (many fluorogenic enzyme substrates are available commercially (see for example Haugland, 1996) including substrates for glycosidases, phosphatases, peptidases and proteases (Craig et al., 1995; Huang et al., 1992; Brynes et al., 1982; Jones et al., 1997; Matayoshi et al., 1990; Wang et al., 1990)), or
  (b) the substrate and product having similar optical properties, but only the product, and not the substrate binds to, or reacts with, the polynucleotide;
(2) adding reagents which specifically bind to, or react with, the product and which thereby induce a change in the optical properties of the polynucleotides allowing their sorting (these reagents can be added before or after breaking the compartments and pooling the polynucleotides). The reagents:
  (a) bind specifically to, or react specifically with, the product, and not the substrate, if both substrate and product are attached to the polynucleotide, or
  (b) optionally bind both substrate and product if only the product, and not the substrate binds to, or reacts with, the polynucleotide.

The pooled polynucleotides encoding catalytic molecules can then be enriched by selecting for the polynucleotides with modified optical properties.

An alternative is to couple the nucleic acid to a product-specific antibody (or other product-specific molecule). In this mode, the substrate (or one of the substrates) is present in each compartment unlinked to the polynucleotide, but has a molecular "tag" (for example biotin, DIG or DNP or a fluorescent group). When the catalyst to be selected converts the substrate to product, the product retains the "tag" and is then captured in the microcapsule by the product-specific antibody. In this way the polynucleotide only becomes associated with the "tag" when it encodes or produces an enzyme capable of converting substrate to product. When all reactions are stopped, the polynucleotides encoding active enzymes will be "tagged" and may already have changed optical properties, for example, if the "tag" was a fluorescent group. Alternatively, a change in optical properties of "tagged" genes can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

Alternatively, selection may be performed indirectly by coupling a first reaction to subsequent reactions that takes place in the same compartment. There are two general ways in which this may be performed. In a first embodiment, the product of the first reaction is reacted with, or bound by, a molecule which does not react with the substrate of the first reaction. A second, coupled reaction will only proceed in the presence of the product of the first reaction. A polynucleotide encoding a polypeptide with a desired activity can then be purified by using the properties of the product of the second reaction to induce a change in the optical properties of the polynucleotide as above.

Alternatively, the product of the reaction being selected may be the substrate or cofactor for a second enzyme-catalysed reaction. The enzyme to catalyse the second reaction can either be translated in situ in the microcapsules or incorporated in the reaction mixture prior to compartmentalisation. Only when the first reaction proceeds will the coupled enzyme generate a product which can be used to induce a change in the optical properties of the polynucleotide as above.

This concept of coupling can be elaborated to incorporate multiple enzymes, each using as a substrate the product of the previous reaction. This allows for selection of enzymes that will not react with an immobilised substrate. It can also be designed to give increased sensitivity by signal amplification if a product of one reaction is a catalyst or a cofactor for a second reaction or series of reactions leading to a selectable product (for example, see Johannsson and Bates, 1988; Johannsson, 1991). Furthermore an enzyme cascade system can be based on the production of an activator for an enzyme or the destruction of an enzyme inhibitor (see Mize et al., 1989). Coupling also has the advantage that a common selection system can be used for a whole group of enzymes which generate the same product and allows for the selection of complicated chemical transformations that cannot be performed in a single step.

Such a method of coupling thus enables the evolution of novel "metabolic pathways" in vitro in a stepwise fashion, selecting and improving first one step and then the next. The selection strategy is based on the final product of the pathway, so that all earlier steps can be evolved independently or sequentially without setting up a new selection system for each step of the reaction.

Expressed in an alternative manner, there is provided a method of isolating one or more polynucleotides encoding a polypeptide having a desired catalytic activity, comprising the steps of:
  (1) expressing polynucleotides to give their respective polypeptides;
  (2) allowing the polypeptides to catalyse conversion of a substrate to a product, which may or may not be directly selectable, in accordance with the desired activity;
  (3) optionally coupling the first reaction to one or more subsequent reactions, each reaction being modulated by the product of the previous reactions, and leading to the creation of a final, selectable product;
  (4) linking the selectable product of catalysis to the polynucleotides by either:
     a) coupling a substrate to the polynucleotides in such a way that the product remains associated with the polynucleotides, or
     b) reacting or binding the selectable product to the polynucleotides by way of a suitable molecular "tag" attached to the substrate which remains on the product, or
     c) coupling the selectable product (but not the substrate) to the polynucleotides by means of a product-specific reaction or interaction with the product; and
  (5) selecting the product of catalysis, together with the polynucleotide to which it is bound, either by means of its characteristic optical properties, or by adding reagents which specifically bind to, or react specifically with, the product and which thereby induce a change in the optical properties of the polynucleotides wherein steps (1) to (4) each polynucleotide and respective polypeptide is contained within a microcapsule.

All of the catalytic modes described herein may also be performed with the roles of the polypeptide and the substrate/inhibitor/product/reagent reversed. For example, the library polypeptide of the invention may be screened for substrate or regulatory activity by providing an enzyme as a target. Selection by regulatory activity is also described below.

4.7.3 Substrate Specificity/Selectivity

Polynucleotides encoding enzymes with substrate specificity or selectivity can be specifically enriched by carrying out a positive selection for reaction with one substrate and a negative selection for reaction with another substrate. Such combined positive and negative selection pressure should be of great importance in isolating regio-selective and stereo-selective enzymes (for example, enzymes that can distinguish between two enantiomers of the same substrate). For example, two substrates (e.g. two different enantiomers) are each labelled with different tags (e.g. two different fluorophores) such that the tags become attached to the polynucleotide by the enzyme-catalysed reaction. If the two tags confer different optical properties on the polynucleotide the substrate specificity of the enzyme can be determined from the optical properties of the polynucleotide and those polynucleotides encoding polypeptides with the wrong (or no) specificity rejected. Tags conferring no change in optical activity can also be used if tag-specific ligands with different optical properties are added (e.g. tag-specific antibodies labelled with different fluorophores).

4.7.4 Regulation

A similar system can be used to select for regulatory properties of cyclic polypeptides.

In the case of selection for a regulator molecule which acts as an activator or inhibitor of a biochemical process, the components of the biochemical process can either be translated in situ in each compartment or can be incorporated in the reaction mixture prior to compartmentalisation, with the exception that components capable of permeating the compartment material may be contacted with the compartment after compartmentalisation. If the polynucleotide being selected is to encode an activator, selection can be performed for the product of the regulated reaction, as described above in connection with catalysis. If an inhibitor is desired, selection can be for a chemical property specific to the substrate of the regulated reaction, or for the absence of a chemical property specific to the product of the regulated reaction.

There is therefore provided a method of sorting one or more polynucleotides coding for a polypeptide exhibiting a desired regulatory activity, comprising the steps of:
  (1) expressing polynucleotides to give their respective polypeptides;
  (2) allowing the polypeptides to activate or inhibit a biochemical reaction, or sequence of coupled reactions, in accordance with the desired activity, in such a way as to allow the generation or survival of a selectable molecule;
  (3) linking the selectable molecule to the polynucleotides either by
     a) having the selectable molecule, or the substrate from which it derives, attached to the polynucleotides, or
     b) reacting or binding the selectable product to the polynucleotides, by way of a suitable molecular "tag" attached to the substrate which remains on the product, or
     c) coupling the product of catalysis (but not the substrate) to the polynucleotides, by means of a product-specific reaction or interaction with the product; or
     d) immobilising the components of the reaction and any products in a gel. In this mode, a gel forming agent or agents must be included with the encapsulated reaction components at the start of the process. The gel may form for example by cooling the reaction to the phase-change temperature of the gel; or
     e) maintaining the reaction components and any products within the microcapsule;
  (4) selecting the selectable product, together with the polynucleotide to which it is bound, either by means of its characteristic optical properties, or by adding reagents which specifically bind to, or react specifically with, the product and which thereby induce a change in the optical properties of the polynucleotides wherein steps (1) to (3) each polynucleotide and respective polypeptide is contained within a compartment.

In modes involving option (e) in step (3), and the addition of reagents in step (4), a semi-permeable compartment material should be chosen that allows the permeation of any such reagents. In embodiments, the compartment is not disrupted before sorting.

In general, when selecting for a regulator or modulator of a biochemical activity, for example an activator or an inhibitor of an enzyme, the candidate regulator—in this case, the cyclic polypeptide—is contacted with the target of regulation. The target and candidate are also contacted with all other reaction conditions and components normally necessary for the activity to take place (i.e. absent any regulators that might interfere with the assay). The mixture is incubated for a period of time, before activity of the target, or absence thereof, is assessed.

A reporter may be included in the reaction to facilitate the detection of any activity. A detectable reporter is a molecule, atom, ion or group which is detectable by standard detection methodologies. For example, the reporter may be capable of producing a detectable signal in response to a stimulus, such as a contact with a chromogenic substrate or light at an appropriate excitation wavelength.

The presence or amount of detectable reporter may be determined by detecting or measuring the signal produced by the reporter. Suitable detectable labels may include fluorescent reporters, chromogenic reporters, Raman-active reporters, such as mercaptopyridine, thiophenol (TP), mercaptobenzoic acid (MBA), and dithiobis succinimidyl nitrobenzoate (DNBA), mass-spectrometry reporters, and particles that can be identified by their shape by image analysis.

Suitable fluorescence reporters include fluorescein and fluorescein derivatives such as O-methyl-fluorescein or fluorescein isothiocyanate (FITC), phycoerythrin, Europium, TruRed, Allophycocyanin (APC), PerCP, Lissamine, Rhodamine, B X-Rhodamine, TRITC, BODIPY-FL, FluorX, Red 613, R-Phycoerythrin (PE), NBD, Lucifer yellow, Cascade Blue, Methoxycoumarin, Aminocoumarin, Texas Red, Hydroxycoumarin, Alexa Fluor~dyes (Molecular Probes) such as Alexa Fluor~350, Alexa Fluor~488, Alexa Fluor~546, Alexa Fluor~568, Alexa Fluor~633, Alexa Fluor~647, Alexa Fluor~660, and Alexa Fluor~700, sulfonate cyanine dyes (AP Biotech), such as Cy2, Cy3, Cy3.5, Cy5, Cy5.5 and Cy7, IRD41 IRD700 (Li-Cor, Inc.), NIR-1 (Dejindom, Japan), La Jolla Blue (Diatron), DyLight™ 405, 488, 549, 633, 649, 680 and 800 Reactive Dyes (Pierce/Thermo Fisher Scientific Inc) or LI-COR™ dyes, such as IRDye™ (LI-COR™ Biosciences).

The reporter may be a substrate, product, or intermediate of the biochemical process. It may be the direct substrate or product of the target of regulation. In other embodiments, the reporter may not be the direct substrate or product of the target of regulation. For example, the reporter may be acted upon or produced in an earlier step of the biochemical activity. Alternatively, the reporter may be acted upon or produced in a later step of the biochemical activity. In a simple enzyme cascade, Accumulation of the reporter (in comparison to a control lacking the cyclic polypeptide) indicates the activation of any steps preceding the production of the reporter ("up-stream" steps) and/or inhibition of any steps following production of the reporter ("down-stream" steps). Conversely, absence of the reporter indicates inhibition of any steps preceding production of the reporter and/or activation of any steps following production of the reporter. Alternatively, the reporter is the substrate or product of a separate biochemical process that has been coupled to the biochemical process involving the target of regulation.

Suitable reporter substrates which may be converted into detectable reporters by the action of a specific enzyme are well known in the art. For example, the reporter substrate fluorescein disulphate may be converted by an arylsulfatase into the detectable reporter fluorescein. Similarly, fluorescein phosphate, and fluorescein acetate may be used with phosphatases and acetylases respectively.

Numerous reporter substrates are commercially available (for example, Molecular Probes Inc) or may be synthesised by standard procedures.

Preferably the detectable reporter is retained in the beads.

In other embodiments, the reporter may be a ligand that binds to a component of the biochemical process. The candidate regulator may then modulate the binding activity of the reporter. In this case, suitable reporters will undergo a detectable physicochemical change when bound. The reporter may bind directly to the target of regulation. In other embodiments, the reporter may not bind directly to the target of regulation but to another component up-stream or down-stream from the target of regulation in the biochemical activity. However, in any case, the binding of the reporter must be dependent on the activity of the target of regulation, be it directly or indirectly. If the candidate regulator inhibits binding of the reporter, the signal associated with the unbound reporter will be prevalent (i.e. increased with respect to a positive control). Conversely, if the candidate regulator promotes binding, the signal associated with bound reporter will be prevalent (i.e. increased with respect to a negative control).

Other formats will be readily considered by the skilled person. For example, the target of regulation may be an enzyme that catalyses a reaction which produces an inhibitor preventing another component of the biochemical activity from binding to the reporter. In any case, the relationship between the presence of a regulatory component and its effect on the reporter will be readily ascertained by the skilled person.

In embodiments, the components of the reporter assay are incorporated into the compartment at the same time as the IVTT system. Some components of the reporter assay may be transcribed from additional polynucleotides by the IVTT system in the capsule, concomitant with expression of the cyclic polypeptide.

In some embodiments, the compartment decompartmentalised gel bead comprising co-immobilised polynucleotide and cyclic peptide may be contacted with media comprising the components of the reporter assay.

In some embodiments, some components of the reporter assay, and/or polynucleotides encoding components of the reporter assay, are incorporated into the compartment at the same time as the IVTT system. In this embodiment, the remaining components of the reporter assay are contacted with the compartment or decompartmentalised gel bead at a later stage.

In embodiments where reporter assay components are contacted with a compartment, the compartment material should be selected in order that reporter assay components initially present only in the environment external to the compartment are able to permeate across the compartment boundary into the internal volume of the compartment.

4.7.5 Protein-Protein Interaction

Protein-protein interactions (PPIs) may be monitored by an assay (for example, FRET assay or HTRF assay) which may be encapsulated with the library, or later merged using droplet merging, or incorporated by reconstituting decompartmentalised gel beads in the assay medium.

To perform the assay, a FRET donor moiety may be attached to one protein of an interacting pair and a FRET acceptor moiety may be attached to the other protein in an interacting pair. Positioning of the donor/acceptor moieties to ensure sufficient proximity for resonance energy transfer when the two proteins are interacting is within the purview of one skilled in the art. The FRET functionalised proteins are then contacted with the polypeptides in the library.

Presence of a polypeptide according to the invention which inhibits the interaction between the two proteins would not FRET, whereas those containing inactive molecules will still display a FRET signal. These two species can be easily separated with FACS.

The assay may also be performed in the opposite direction to identify polypeptides that create or enhance an interaction between two proteins, in which case the presence of or an increase in FRET indicates a polypeptide promoting the interaction.

4.7.6 Optical Properties of the Polypeptide

It is possible to select for inherent optical properties of polypeptides if, in the compartments, the polypeptide binds back to the polynucleotide, for example through a common element of the polypeptide which binds to a ligand which is part of the polynucleotide. The polynucleotides can then be sorted using the optical properties of the bound polypeptides. This embodiment can be used, for example, to select variants of green fluorescent protein (GFP) (Cormack et al., 1996; Delagrave et al., 1995; Ehrig et al., 1995), with improved fluorescence and/or novel absorption and emission spectra.

4.7.7 Flow Sorting of Polynucleotide/Polypeptide

In a preferred embodiment of the invention, the beads, capsules, polynucleotides, and/or polypeptides will be sorted by flow cytometry. A variety of optical properties can be used to trigger sorting, including light scattering (Kerker, 1983) and fluorescence polarisation (Rolland et al., 1985). In a highly preferred embodiment the difference in optical properties of the beads, capsules, polynucleotides, and/or polypeptides will be a difference in fluorescence and the beads, capsules, polynucleotides, and/or polypeptides will be sorted using a fluorescence activated cell sorter (Norman, 1980; Mackenzie and Pinder, 1986), or similar device. In an especially preferred embodiment the beads, capsules, polynucleotides, and/or polypeptides comprises a nonfluorescent nonmagnetic (e.g. polystyrene) or paramagnetic microbead (see Fornusek and Vetvicka, 1986), optimally 0.6 to 1.0 μm diameter, to which are attached both the gene and the groups involved in generating a fluorescent signal:

(1) commercially available fluorescence activated cell sorting equipment from established manufacturers (e.g. Becton-Dickinson, Coulter) allows the sorting of up to 108 beads, capsules, polynucleotides, and/or polypeptides (events) per hour;
(2) the fluorescence signal from each bead corresponds tightly to the number of fluorescent molecules attached to the bead. At present as little as few hundred fluorescent molecules per particle can be quantitatively detected;
(3) the wide dynamic range of the fluorescence detectors (typically 4 log units) allows easy setting of the stringency of the sorting procedure, thus allowing the recovery of the optimal number of beads, capsules, polynucleotides, and/or polypeptides from the starting pool (the gates can be set to separate beads with small differences in fluorescence or to only separate out beads with large differences in fluorescence, dependant on the selection being performed;
(4) commercially available fluorescence-activated cell sorting equipment can perform simultaneous excitation at up to two different wavelengths and detect fluorescence at up to four different wavelengths (Shapiro, 1983) allowing positive and negative selections to be performed simultaneously by monitoring the labelling of the beads, capsules, polynucleotides, and/or polypeptides with two (or more) different fluorescent markers, for example, if two alternative substrates for an enzyme (e.g. two different enantiomers) are labelled with different fluorescent tags the beads, capsules, polynucleotides, and/or polypeptides can labelled with different fluorophores dependent on the substrate used and only genes encoding enzymes with enantioselectivity selected.
(5) highly uniform derivatised and non-derivatised non-magnetic and paramagnetic microparticles (beads) are commercially available from many sources (e.g. Sigma, and Molecular Probes) (Fornusek and Vetvicka, 1986).

4.8 Isolation of Polynucleotide

Polynucleotide from the one or more beads may be isolated, amplified, cloned, sequenced or otherwise manipulated.

A method described herein may further comprise identifying and/or isolating the polynucleotide from one or more compartments or beads identified as containing a candidate cyclic polypeptide.

The polynucleotide from the one or more beads may be isolated, amplified, sequenced cloned and/or otherwise investigated. For example, the polynucleotide may be extracted using conventional techniques such as gel-extraction columns or agarose, and/or amplified isothermally (e.g. multiple-primed RCA) or by PCR or both consecutively.

The methods described herein can also be applied by analogy to systems wherein the compartment is, for example, a vesicle or an alginate microcapsule. These systems can also be manipulated to provide micro-reactors for PCR, agarose gelification, and IVTT, followed by assays and high-throughput sorting.

EXAMPLES 5.1 Preface to the Examples

In one embodiment, the present invention overcomes the limitations in the art by porting SICLOPPS into microfluidic droplets. Not only can we express individual SICLOPPS library members in each droplet, as this is achieved by in vitro transcription/translation, the DNA code for each cyclic peptide is also contained in the same droplet, making identification of hits very simple via PCR amplification and DNA sequencing. This library can be interfaced with any pharmaceutical assay with a fluorescent or colorimetric output (e.g. FRET, HTRF). This method further allows generation of libraries of hundreds of millions of cyclic peptides, and can include non-natural amino acids.

To overcome the limitations of droplet merging we utilize an agarose-in-oil droplet based methodology for highly parallel and efficient single molecule DNA amplification prior to in vitro protein expression. This method capitalizes on the thermo-responsive sol-gel switching properties of agarose for the capture of single DNA molecules prior to amplification by Phi29 DNA polymerase. Following DNA amplification, the agarose droplets are gelated (or solidified) to form agarose beads, thereby trapping all amplicons in each micro-reactor to preserve the monoclonality of each droplet.

The use of monodisperse agarose-in-oil microdroplets has previously been used to monitor biochemical reactions within gelified microbeads. As noted, the transition from an agarose droplet to a solidified agarose particle provides additional stability and facilitated manipulation. Once solidified, we demonstrate the isolation of isothermally amplified DNA to only within the agarose bead (i.e., the pre-amplified DNA does not diffuse out). The resulting particles can therefore be recovered by breaking the emulsion and washed to permit re-suspension in an IVTT compatible buffer to effectively bypass the constraints associated with droplet merging. After re-suspension in IVTT compatible buffer, the other components of the IVTT system may be added and, in embodiments, the IVTT-competent agarose bead may be re-emulsified to form IVTT micro-reactors.

The methodology developed enables the high-throughput generation of uniform droplets with efficient single molecule DNA amplification, thereby delivering a promising platform for many single copy genetics based studies.

Overall, we describe a novel ultra-high throughput screening platform that can be used for the rapid selection of protein-protein interaction inhibitors via the in vitro compartmentalization of SICLOPPS derived cyclic peptide libraries in femtolitre-sized aqueous compartments, using FACS to selectively recover droplets displaying the desired phenotypic trait.

We demonstrate successful single molecule DNA amplification in monodisperse agarose droplets through the solidification and subsequent breaking of emulsion (via the addition of PFO) to permit the isolation of DNA enriched agarose particles. Amplified DNA is detected by staining with a fluorescent dsDNA intercalating dye, which simultaneously permits detection via flow cytometry. A single distinct agarose particle population on side versus forward scatterplots is observed, with a prominent increase in green fluorescence intensity when compared to controls comprising no Phi29 DNA polymerase.

Prior to the introduction of agarose particles into an IVTT containing droplet, the agarose beads are washed to remove any unbound DNA alongside the removal of incompatible DNA amplification buffer; in the absence of washing, IVTT is inhibited and no GFP expression is observed.

For agarose-in-IVTT-in-oil (double emulsion) formation, agarose particles are re-introduced into a hydrophobic microfluidic device along with the components for IVTT. Following incubation at 37 C, protein expression is stopped through placing the emulsion on ice. For triple emulsion formation (agarose-in-IVTT-in-oil-in-water), double emulsion droplets are injected into a third and final hydrophilic microfluidic device for re-emulsification into a flow cytometry compatible configuration.

Finally, triple emulsions comprising in vitro expressed GFP from a GFP encoding plasmid are successfully sorted using FACS. Droplets are injected and sorted at rates exceeding 1,000 events per second, therefore equating to 60,000 events per minute or 3.2 million per hour.

Overall, we demonstrate the successful implementation of agarose particles in IVTT for the in vitro expression of polypeptide in microfluidically generated droplets.

Example 1: The Generation of Monodisperse Single Water-in-Oil Emulsion Droplets at the Femto-Litre Scale The generation of aqueous femtodroplets using a 10×5 μm (width×depth) flow-focusing microfluidic device on chip with the capacity to achieve droplets 5-50 fL in volume is demonstrated in FIG. 1, whereby two immiscible liquids enter the device via four parallel microchannels, with the continuous HFE-7500-based phase flowing in from the outside two channels and the dispersed aqueous phase flowing in from the inner two. Downstream, the aqueous microchannels meet prior to entering the orifice. The initial observation of a fixed, elongated aqueous stream at the nozzle orifice during droplet formation as reported in Shim et al., is representative of a "tipstreaming" mechanism of action for droplet production with a dripping regime of breakup i.e., the formation of a conical droplet shape with a highly sharpened tip from which smaller droplets (as small as 0.5 μm in diameter) are released. First reported in 1934, surfactant-mediated microscale tipstreaming represents a hydrodynamic phenomenon capable of generating submicron sized droplets via interfacial surfactant concentration gradients that develop as a result of the elongational flows generated within flow-focusing geometries.

To demonstrate the well-controlled production of monodisperse water-in-oil (w/o) femtodroplets for SICLOPPS library encapsulation, droplets comprising 100 μM fluorescein (FITC dye) in 1×TAE (pH ~7.5, since the emission of FITC fluorescence is strongly dependent upon the surrounding pH) were formed in hydrofluoroether HFE-7500 previously mixed with 5% Krytox 157 FSL Jeffamine ED-600 disalt surfactant (JUS, not commercially available) to decrease the interfacial tension at the oil-water interface. To investigate the frequency of femtodroplet formation and therefore determine the theoretical number of encapsulated SICLOPPS library variants achievable over time (assuming single molecule encapsulation), the influence of volumetric flow speeds on droplet diameter (as dictated by the oil/water flow rate ratio, $R_1/R_2$) was examined by increasing the oil phase flow rate in a step-wise manner (10-60 μl/h) whilst maintaining a constant aqueous flow of 10 μl/h. The frequency of droplet formation, which is expected to increase with a decrease in droplet size, was theoretically calculated as follows $f=Q_{aq}/V_d$, where f is the frequency of production (Hz), $Q_{aq}$ the aqueous phase flow rate (μl/s) and $V_d$ the final droplet volume (μl).

Figures 2A, 2B, 2C:
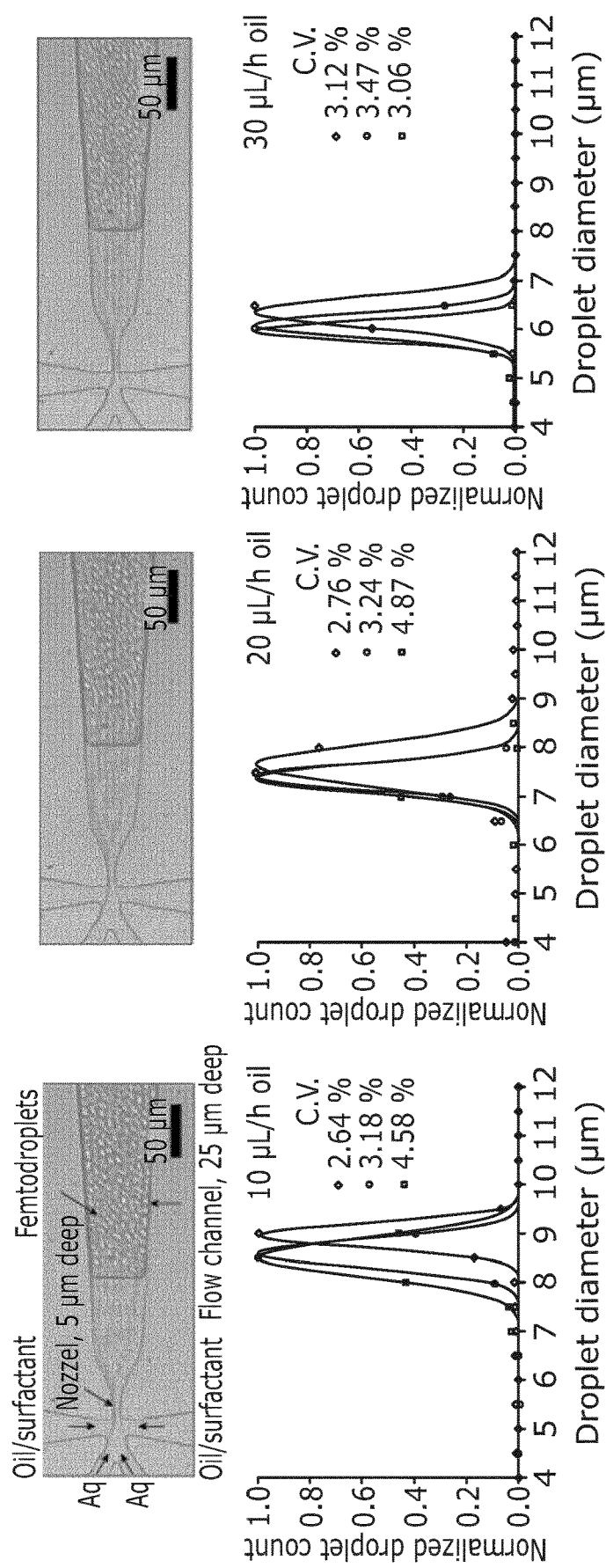

To determine the diameter of microfluidically generated emulsion droplets, samples were pipetted into disposable Fast-Read Counting Slides and imaged using an Olympus CKX41 inverted microscope or Zeiss Axio II; a QIClick CCD camera was fitted for image capture and controlled using open source microscopy software (Micro-Manager). For analysis, brightfield and fluorescent photographs were saved as 16-bit files and processed with ImageJ software to yield statistics on droplet diameter and volume via the "Analyse Particles" function. Accordingly, the circularity above a user-defined threshold for all objects larger than a specified minimum cut-off (0.8) was measured and tabulated for data processing. Resultantly, the droplet diameter distribution under each flow rate condition is presented in figure. 2.

Figure 3:
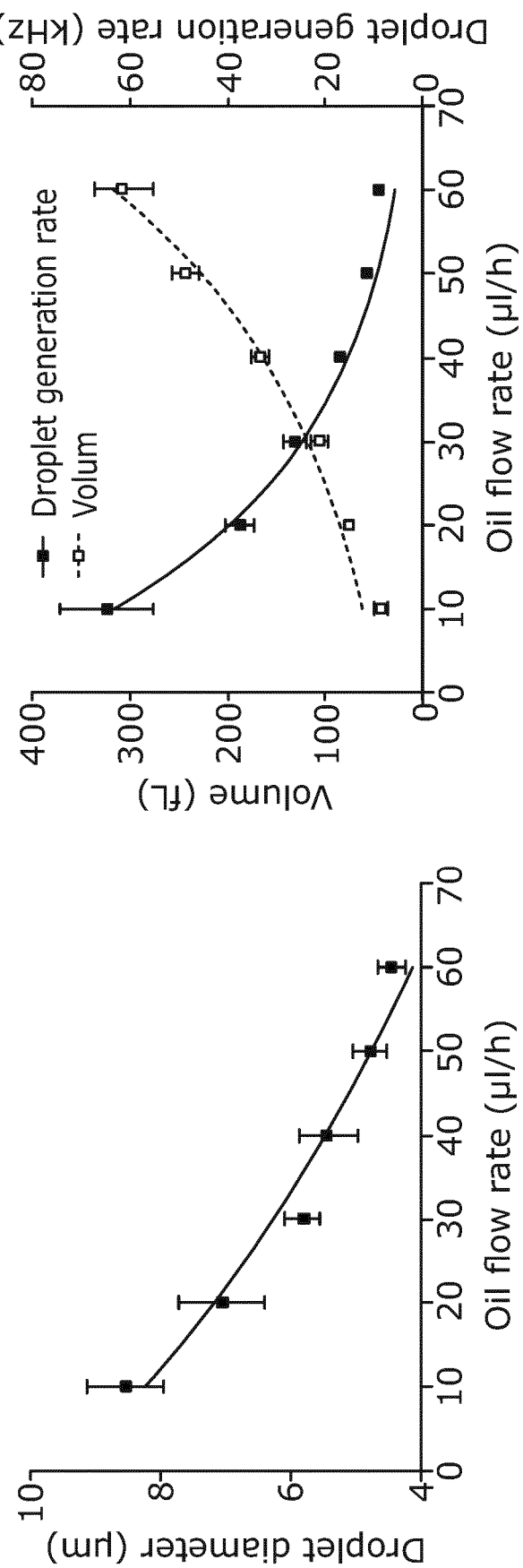
FIG. 3. Analysis of single emulsion droplet diameter, volume and production rate. (Left) Droplet diameter versus oil flow rate for single emulsion droplet generation. (Right) Droplet generation rate in kHz and average volumes plotted against oil flow rate of 10-60 µl/h; an increase in droplet volume corresponds to a decrease in its resulting rate of production. Values plotted as mean with SD from which three independent photographs of three separate samples were analysed.

An increase in the oil/surfactant flow rate is followed by a decrease in the overall droplet diameter. Likewise, a decrease in the droplet volume is matched by an increase in its production frequency, as demonstrated in FIG. 3.

Figure 4:
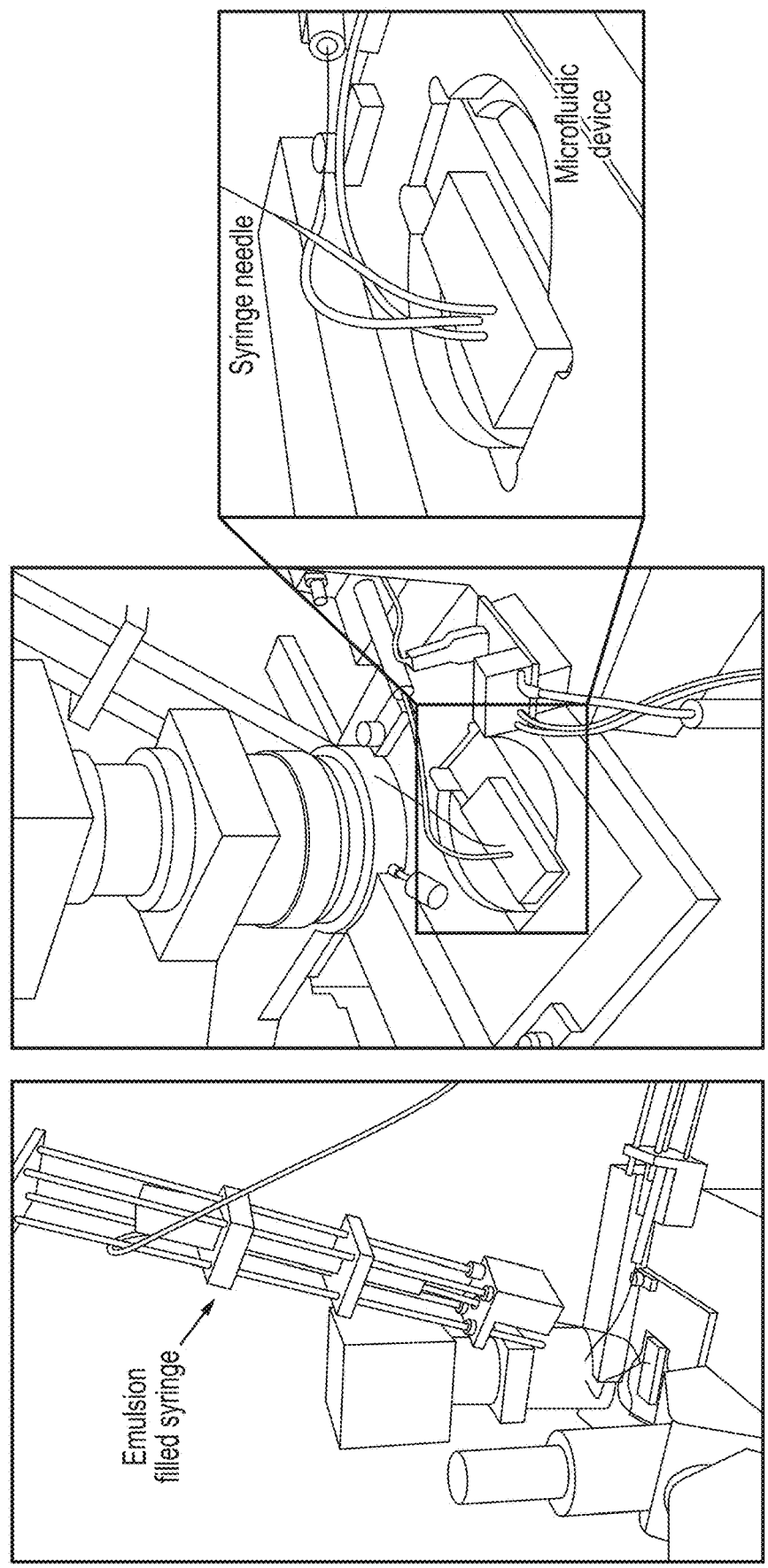
FIG. 4. Two-chip based microfluidic set-up for the generation of double emulsion droplets. Single emulsion droplets for re-emulsification are contained within a glass syringe in an upright position. Once settled, the emulsion is driven through a second microfluidic device (enlarged crop) with larger channel dimensions to permit double emulsion droplet formation.

Example 2: The Generation of Water-in-Oil-in-Water Double Emulsion Droplets for Flow Cytometry Analysis For flow cytometric analysis of SICLOPPS enclosed emulsion samples, a double emulsion water-in-oil-in-water configuration, generated via two-step re-emulsification, is required to ensure compatibility. Accordingly, primary FITC containing water-in-oil emulsions generated via a 10×5 μm microfluidic device were transformed into double emulsion droplets using a second, hydrophilic flow-focusing chip with microchannel dimensions measuring 15×16 μm. To permit re-emulsification, the primary emulsion was stored upright within a glass syringe, flaked by fluorinated and mineral oil solutions. During encapsulation, the addition of a second, FC-40 filled syringe was used to facilitate the controlled manipulation and encapsulation of a single primary droplet per double emulsion. Alongside, a 1% tris/tween80 surfactant containing continuous phase was used for interface stabilization. The process of on-chip two-step emulsification is illustrated in FIG. 4.

Figure 5A:
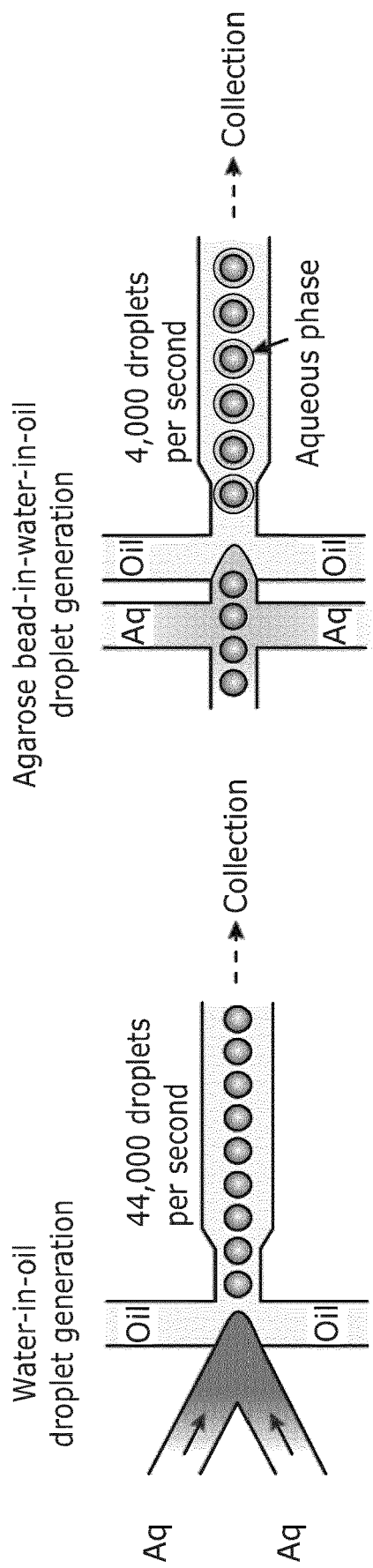
FIGS. 5A-B. Illustration of double emulsion production at the microfluidic device junction; droplets move from left to right. (A) Illustration of single and double emulsion formation on chip; (B) brightfield image of double emulsion droplet formation at the device orifice.
Figure 5B:
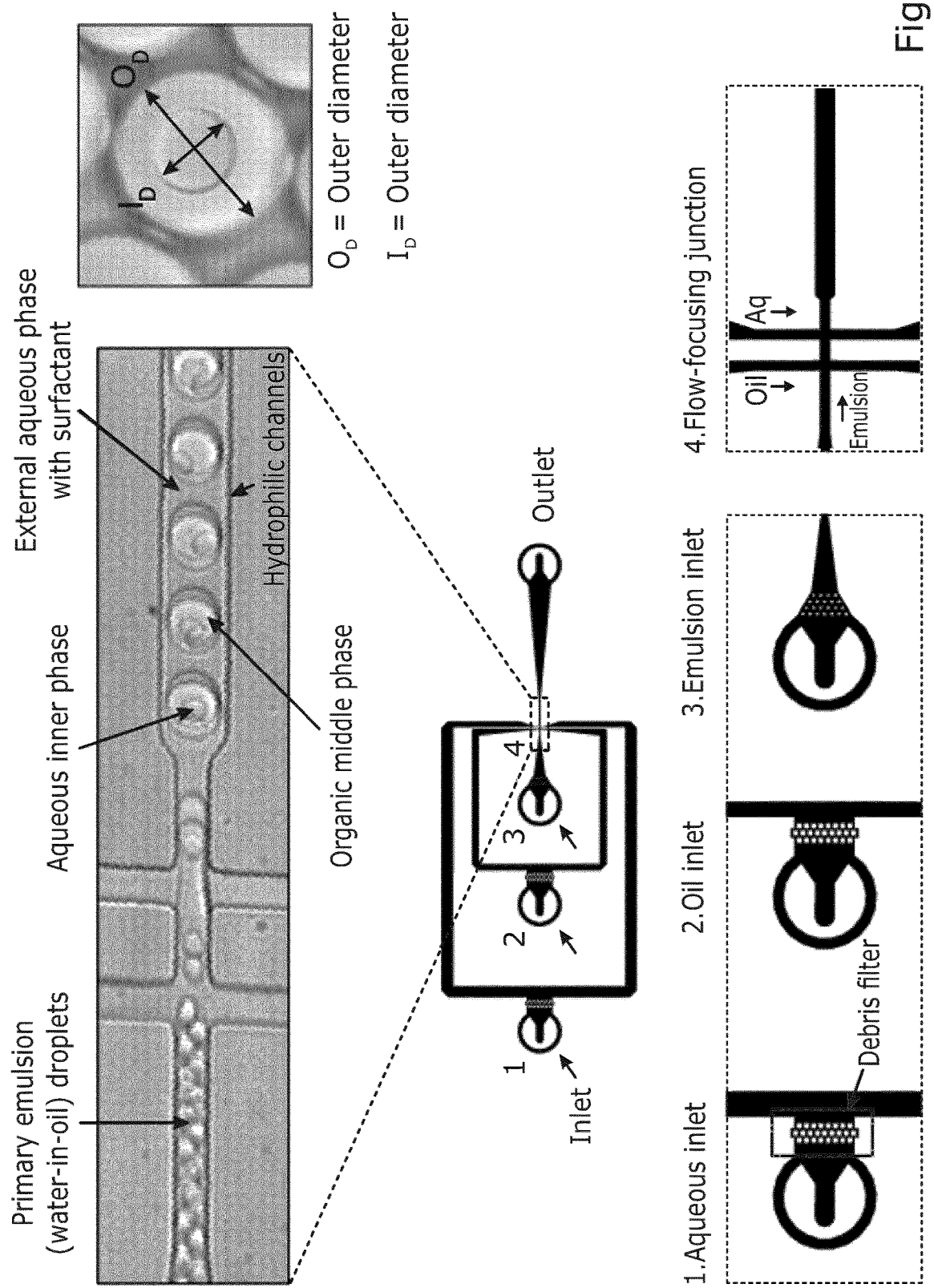

In addition, the workflow for single and double emulsion droplet generation using a flow-focusing microfluidic geometry is illustrated in FIG. 5.

The resulting inner droplet diameter was on average ~6.69 μm, whilst the outer double emulsion diameters was 14.98 μm; accordingly, these ~1.76 pL double emulsions yield ~5.68×10$^8$ droplets/mL. Although the majority (98.21% on average from 10 images) were observed to comprise a single aqueous core, whilst a small proportion (1.79%) was found doubly occupied (arrowhead, FIG. 6). Droplet stability and structural integrity were maintained following 1 month's storage at 4° C.

Figure 6:
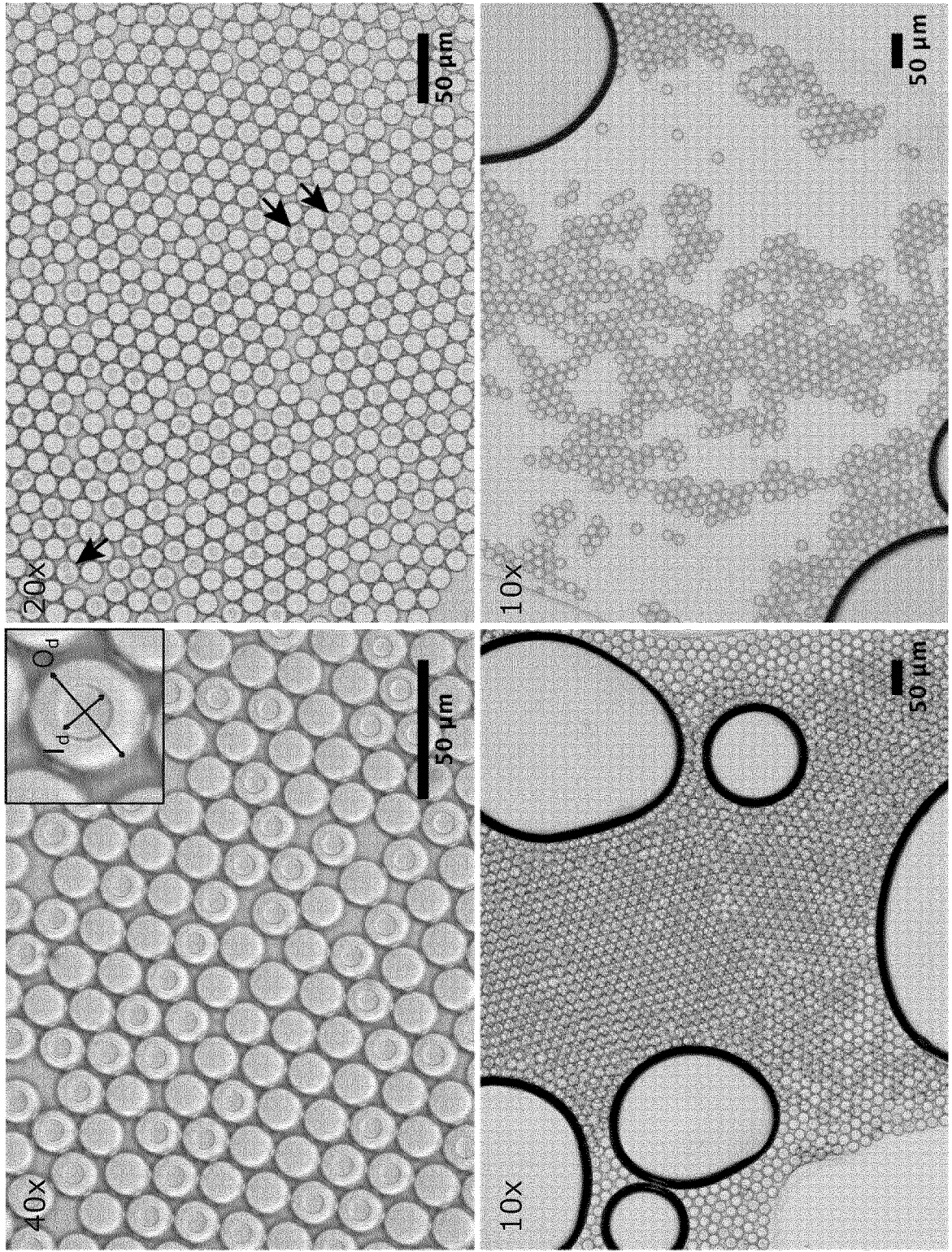
FIG. 6. Generation of highly monodispersed double emulsion (w/o/w) droplets in a controllable and flexible manner. Water-in-oil-in-water (w/o/w) double emulsions droplets containing a 100 µM fluorescein inner core in a FC-40 oil shell and 1% tris/tween80 external phase. Droplets generated using the following flow rates: emulsion—4 µl/h, FC-40 spacer oil—15 µl/h and 1% tris/tween—60 µl/h. Prominent globular structures in 10× magnification photographs represent mineral oil droplets. Arrows highlight doubly occupied double emulsion droplets. (Top left) Insert showing a magnified image of an individual double emulsion droplet; the diameter of the internal aqueous core and overall double emulsion diameter are shown ($I_D$ & $O_D$).
Figure 7B:
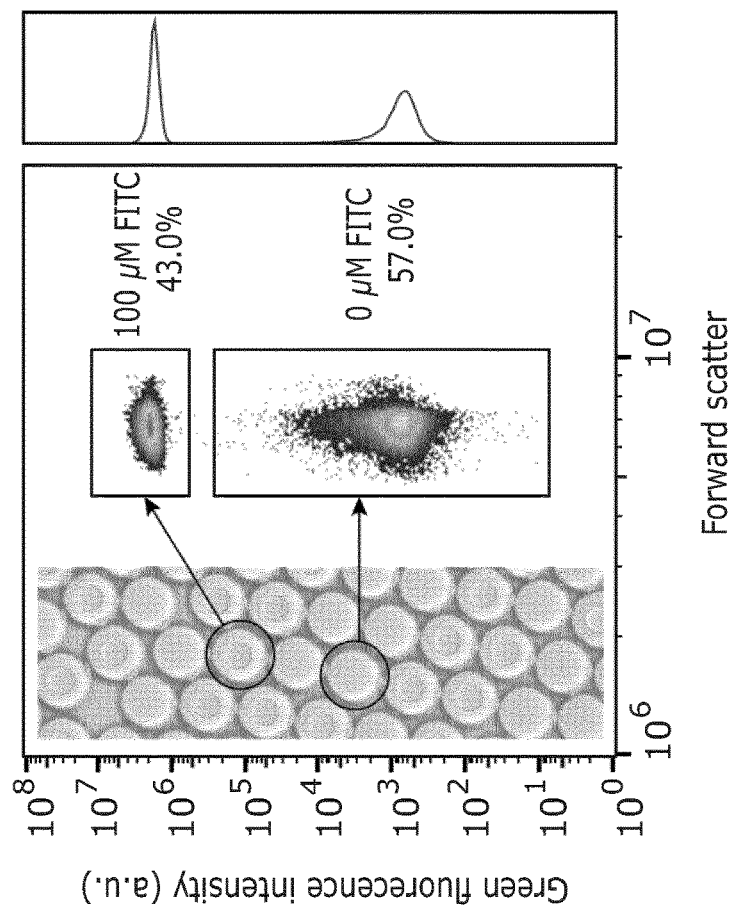
FIGS. 7A-B. Flow cytometric analysis of FITC containing double emulsion droplets. (A) Side scatter versus forward scatter log plots of double emulsion samples, (B) green fluorescence intensity versus forward scatter log plots; forward scatter (above) and green fluorescence intensity (right) histograms are also presented, (C) oil-in-water single emulsion samples prepared in the absence of primary emulsions and using identical flow rates and conditions as in the previous sample to determine levels of background fluorescence, (D) fluorescence versus forward scatter of oil-in-water single emulsion droplets. Single emulsion generation was performed using a JUS device, whilst double emulsion formation with a 15×16 µm (h×w) device. Flow rates and device designs used for oil-in-water generation were identical to those for FITC based w/o/w emulsions to permit comparison. Inserts in (A) and (C) show magnified gated regions of the desired droplet population.
Figure 7A:
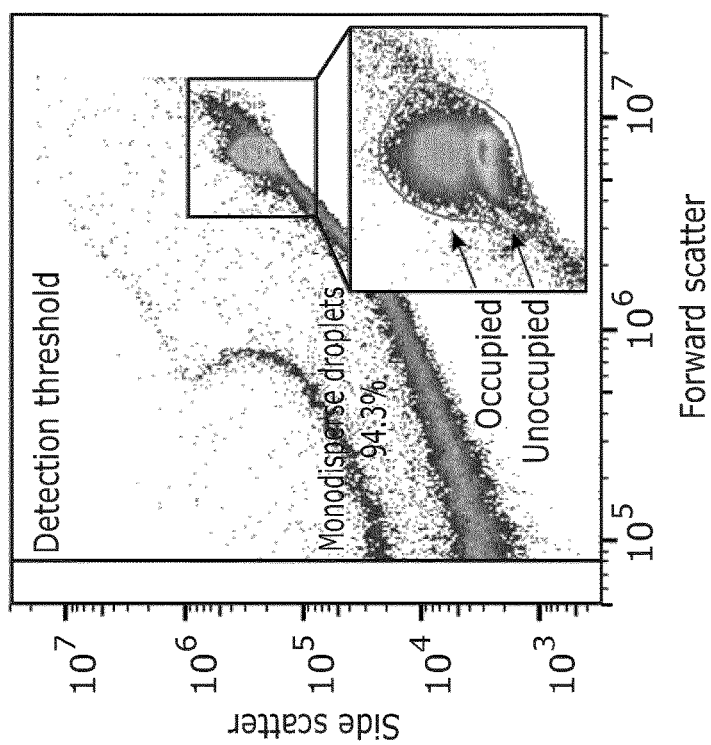
Figure 7D:
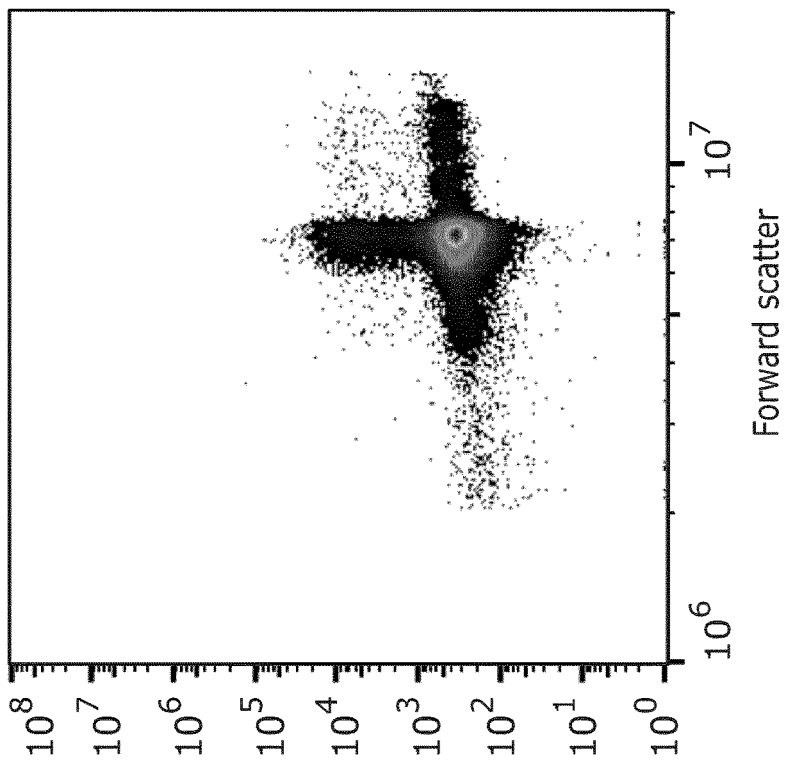
Figure 7C:
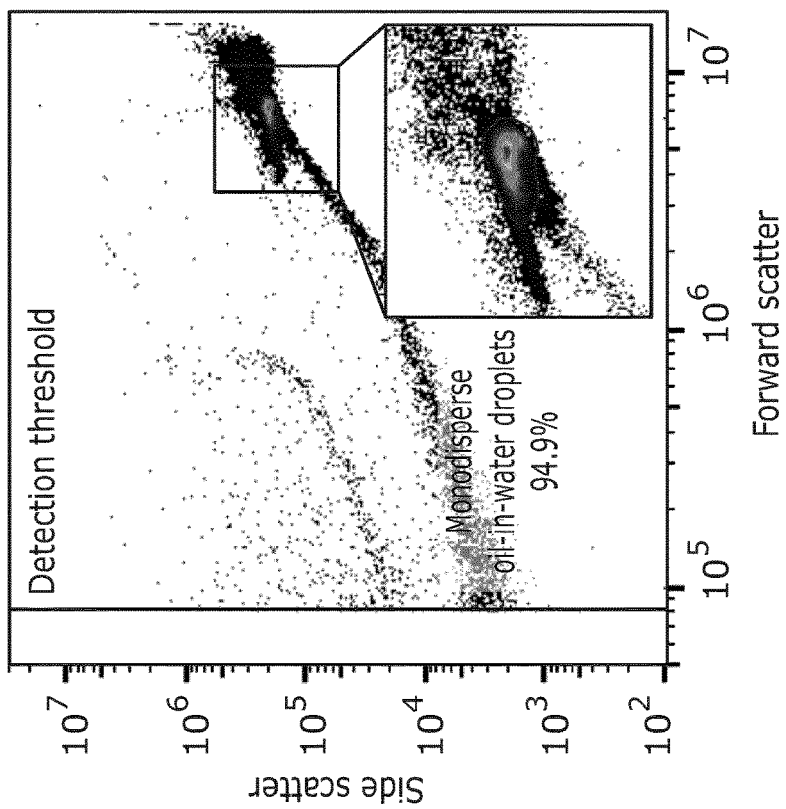

Subsequently, the double emulsion droplets from FIG. 6 were analysed using a BD Accuri C6 flow cytometer. The density plots for on-chip generated double emulsion droplets forms two distinct clusters on cytometric forward and side scatter (FSC and SSC, FIG. 7). Whilst FSC distinguishes droplets based upon their size (diameter), SSC is used to distinguish droplets based upon their internal complexity (or granularity). Resultantly, double emulsion droplets comprising an inner aqueous core will exhibit a greater side scatter than empty oil-in-water droplets, and will therefore exhibit a higher positioning on SSC versus FSC density/scatter plots. Monodisperse droplet populations will exhibit similar forward scatter. Singly occupied (droplets comprising an inner fluorescein core) and unoccupied droplets i.e., those that have failed to encapsulate a primary water-in-oil droplet during on-chip re-emulsification are shown in FIG. 7A. This differentiation is further supported by the corresponding green fluorescence intensity profiles as shown in FIG. 6B, whereby a highly fluorescence droplet population representing singly occupied FITC containing droplets with a fluorescent signal approximately 3 orders of magnitude greater than from that of a second, lower positioned population (unoccupied droplets), which represents a baseline level of fluorescence.

Background fluorescence levels were confirmed by preparing simple oil in water droplets with reagents and conditions entirely identical as to those previously used. A single fluorescence peak and droplet population are observed from the resulting fluorescence histogram and SSC vs FSC plots, respectively, which correspond directly with those from FIGS. 7A & B.

Example 3. Production of a Library of 3.2 Million Cyclic Peptides in Droplets In order to facilitate identification of droplets containing cyclic peptides, we designed an expression system that encodes both the SICLOIPPS inteins and a fluorescent protein (GFP). The droplets containing a SICLOPPS plasmid may be readily identified and sorted/separated based on their fluorescence using FACS. A pETDuet-based plasmid encoding Npu split inteins in SICLOPPS format ($I_C$-extein-$I_N$) was built for CX$_5$ SICLOPPS library construction from vector pARNpuHisSsrA-CX5 (Townend and Tavassoli, 2016, ACS Chemical Biology, 1624-1630). The region encoding the C- and N-inteins together with the hexamer encoding peptide were PCR amplified using forward and reverse primers encoding Eco RI and Hind III restriction enzymes, respectively, in which the reverse primer was designed to omit the SsrA degradation tag. This amplified product was next digested and subsequently cloned into the first multiple cloning site (MCS1) of vector pETDuet-1. GFP was PCR amplified from an encoding geneblock using forward and reverse primers encoding Nde I and Eco RV restriction enzyme sites, respectively; this construct was likewise cloned into MCS2 of vector pETDuet-1 to generate a vector encoding both SICLOPPS and GFP proteins. The resulting plasmid was hereafter utilized as templates in SICLOPPS cyclic peptide library construction.

A hexamer library comprising five variable amino acids and thus 3.2×10$^6$ library members (where X=any amino acid residue) was constructed as previously described (Tavassoli and Benkovic, 2007, Nature Protocols, 1126-1133). The library was designed to encode cyclic peptide hexamers within the first multiple cloning site (MCS) of pETDuet-1 with an initial cysteine residue followed by five randomized residues as a nucleophile at the first position is required for the transesterification step of intein processing (Other residues suitable for providing a nucleophile at the first position include Serine (S) and Threonine (T)). The second MCS was constructed to express GFP and therefore allow for the simultaneous expression of both cyclic peptide and fluorescent protein to allow for the rapid and systematic identification of cyclic peptide containing droplets.

Figure 15:
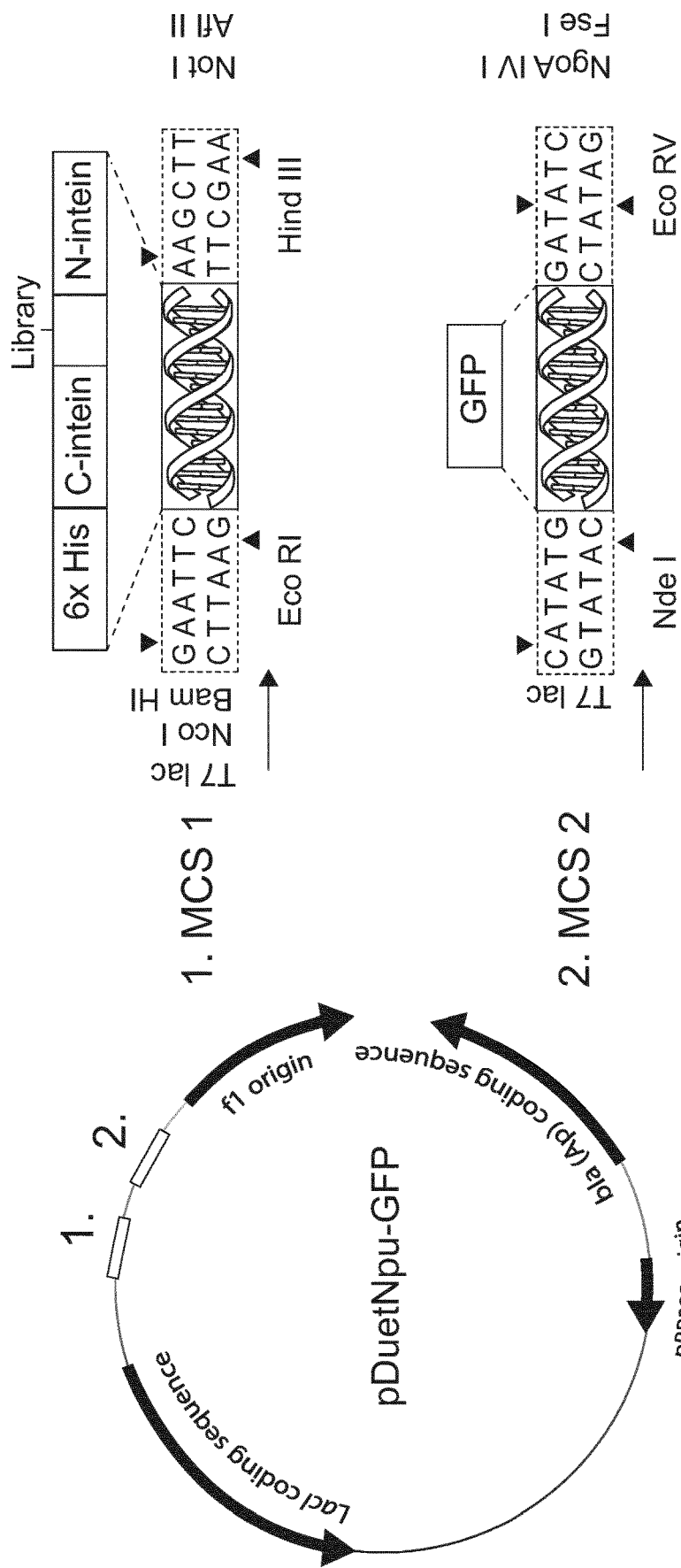
FIG. 15. Illustration of the construction of pETDuet-1 based SICLOPPS vectors for cyclic peptide library generation. Illustration of pDuetNpu-GFP expression vector; MCS1 encodes SICLOPPS with Npu inteins, whilst MCS2 encodes GFP. "Library" indicates the location of the variable polynucleotide sequence of the library. This sequence encodes the cyclic polypeptide in the invention, including a nucleophilic amino acid in the first position (e.g. cysteine, serine, or threonine). It is positioned between two intein fragments and therefore may also be termed the "extein" sequence, in that it encodes the extein that will be spliced out of the SICLOPPS polypeptide after translation.

The resulting plasmid is depicted in FIG. 15.

As previously detailed (Tavassoli and Benkovic, 2007, Nature Protocols, 1126-1133), a two-step PCR-based technique was used in which the random oligonucleotides of the library are incorporated into the forward primer between the region that binds the 3' end of $I_C$ and the 5' end of $I_N$. The variable segment was encoded in the form NNS, where N represents any of the four DNA bases (A, C, G or T) and S represents C or G. The NNS sequence generated 32 codons and encodes all 20 natural occurring amino acids whilst eliminating the ochre (UAA) and opal (UGA) stop codons from the library. It should be noted that there are no limits upon the number of amino acids within the target peptide, allowing cyclic peptides of various sizes to be generated.

The generation of the initial linear PCR product yields mismatches in the random nucleotide region, owing to the sequence complexity of the library. A second PCR using a "zipper" primer corresponding to the 3' end of C-intein was therefore used to ensure the annealing of all DNA sequences to their complimentary strand. The resulting DNA library was incorporated into the SICLOPPS plasmid using standard molecular biology techniques to generate the desired CX$_5$ library within vector pDuetNpuHis-GFP.

Following ligation, SICLOPPS CX$_5$ peptide libraries were transformed into electro-competent DH5α E. coli cells and plated onto LB agar medium and grown overnight at 37° C. Once grown, the resulting colonies were harvested via the scraping of colonies and miniprepped to yield a plasmid library ready for encapsulation and Phi29 mediated pre-amplification in agarose-in-oil droplets as detailed above.

Figure 8A:
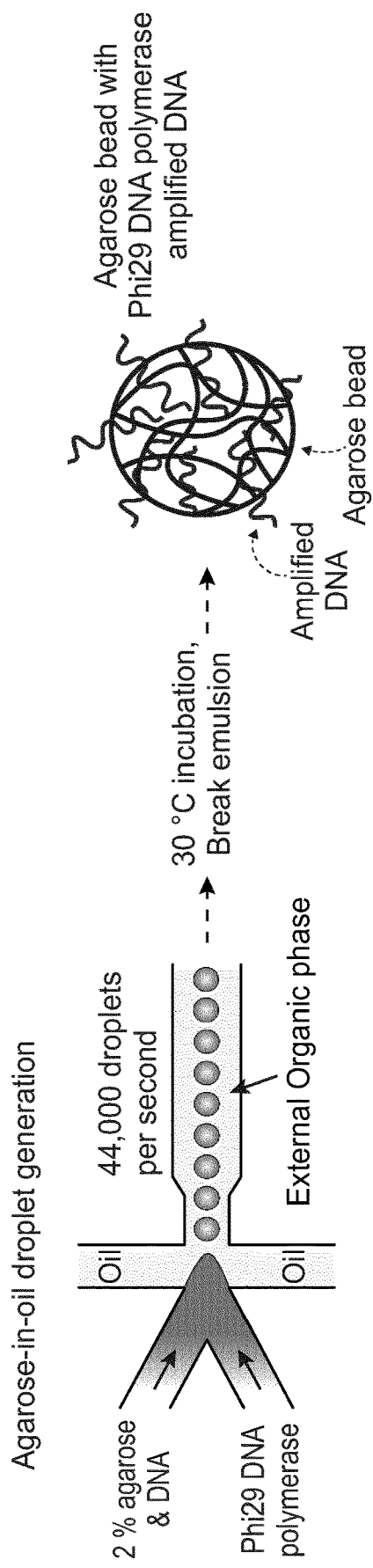
FIGS. 8A-C. Illustration of the formation of triple emulsion IVTT containing droplets using DNA filled agarose beads and a three-chip microfluidic system. (A) Fluorinated oil, agarose/DNA suspension, and Phi29 DNA polymerase are injected into a hydrophobic microfluidic flow-focusing device and collected upon the formation of a stable flow of monodisperse agarose droplets from the flow-focusing junction. (B) Solidified agarose beads are re-injected into a second hydrophobic microfluidic device along with IVTT mixture. (C) The IVTT/DNA containing droplet is re-emulsified a third and final time to yield an external aqueous phase that is now amenable to flow cytometry analysis.
Figures 8B, 8C:
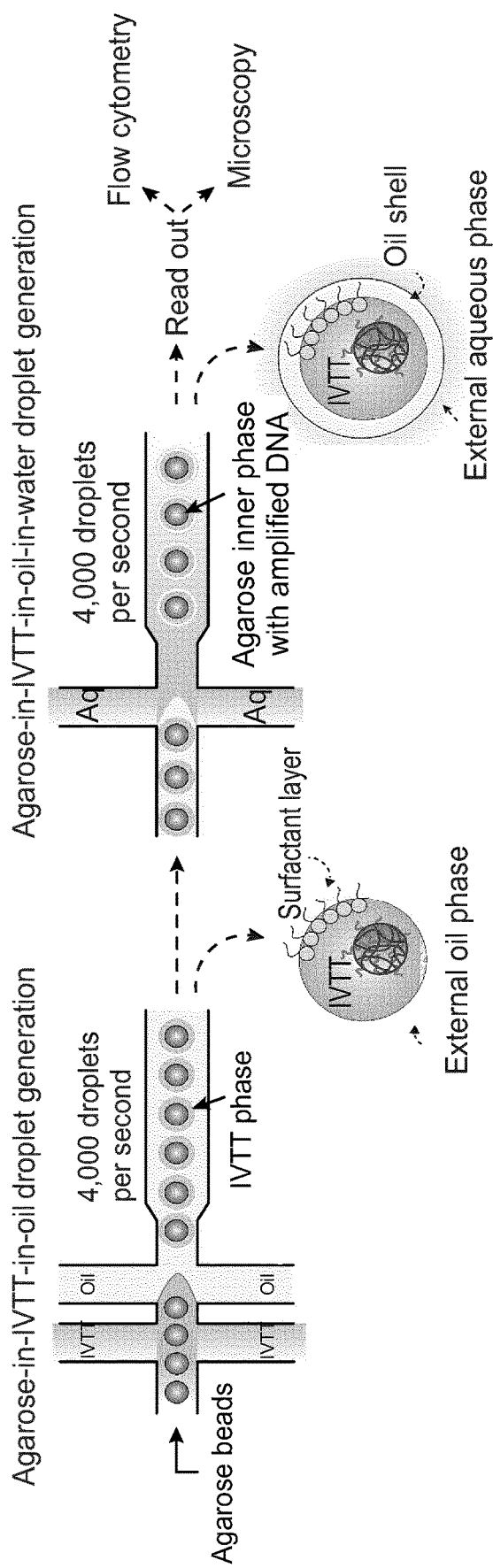

Example 4: The Miniaturization of Biochemical Operations Using Agarose-Based Droplet Microfluidics The above plasmid library (generated in example 3) was used in the following experiments. The application of agarose-in-oil emulsion droplets for amplicon trapping and DNA amplification in gelated agarose beads has materialized into a powerful approach for tackling the challenges of conventional PCR and primer functionalized microbead methods. Here, we capitalize upon the unique thermo-responsive sol-gel switching properties of agarose to describe a highly parallel Phi29 DNA polymerase mediated protocol for the amplification of single DNA plasmid molecules in femtolitre-sized agarose beads ranging 6-7 µm in diameter. We utilize a two-aqueous-inlet emulsion droplet generator with co-encapsulated isothermal amplification reagents along with agarose as a capturing matrix. The monoclonal nature of each product is resultantly preserved within the robust and inert biochemical environment of reach reservoir/bead. Solidified beads enclosing trapped amplicons are subsequently co-encapsulated in an in vitro transcription translation (IVTT) system in the absence of droplet merging to study protein expression in a defined reaction volume, illustrated in FIG. 8. Resultantly, we demonstrate confinement of gene transcription and translation to the membrane-free agarose particles, thereby demonstrating the potential of this upcoming technology in enabling quantitatively new studies of complex biological systems.

FIG. 9 illustrates the agarose droplet microfluidic set-up used for the encapsulation and amplification of single DNA plasmid molecules using Phi29 DNA polymerase, within a microfabricated hydrophobic device for the controlled generation of highly uniform and monodisperse femtolitre emulsion droplets comprising a 1% agarose solution. DNA template molecules are introduced into the droplet along with the agarose solution at a statistically diluted concentration such that the average number of molecules in a single droplet will be no more than approximately one. Ultra-low gelling temperature agarose that remains fluid at 37 C and with a transition gelling point between 8-17 C, is used for encapsulation to enable the facile generation of agarose droplets during device operation. Following off-chip incubation and DNA amplification, switching of the agarose matric to a solid gel phase is permitted through cooling the solution to below the critical gelling point. Once solidified, the beads remain in a solid state unless a rise in temperature occurs. As a result, amplified DNA remains trapped within the solidified agarose matrix therefore retaining droplet monoclonality even after the removal of the external oil phase.

Figure 9A:
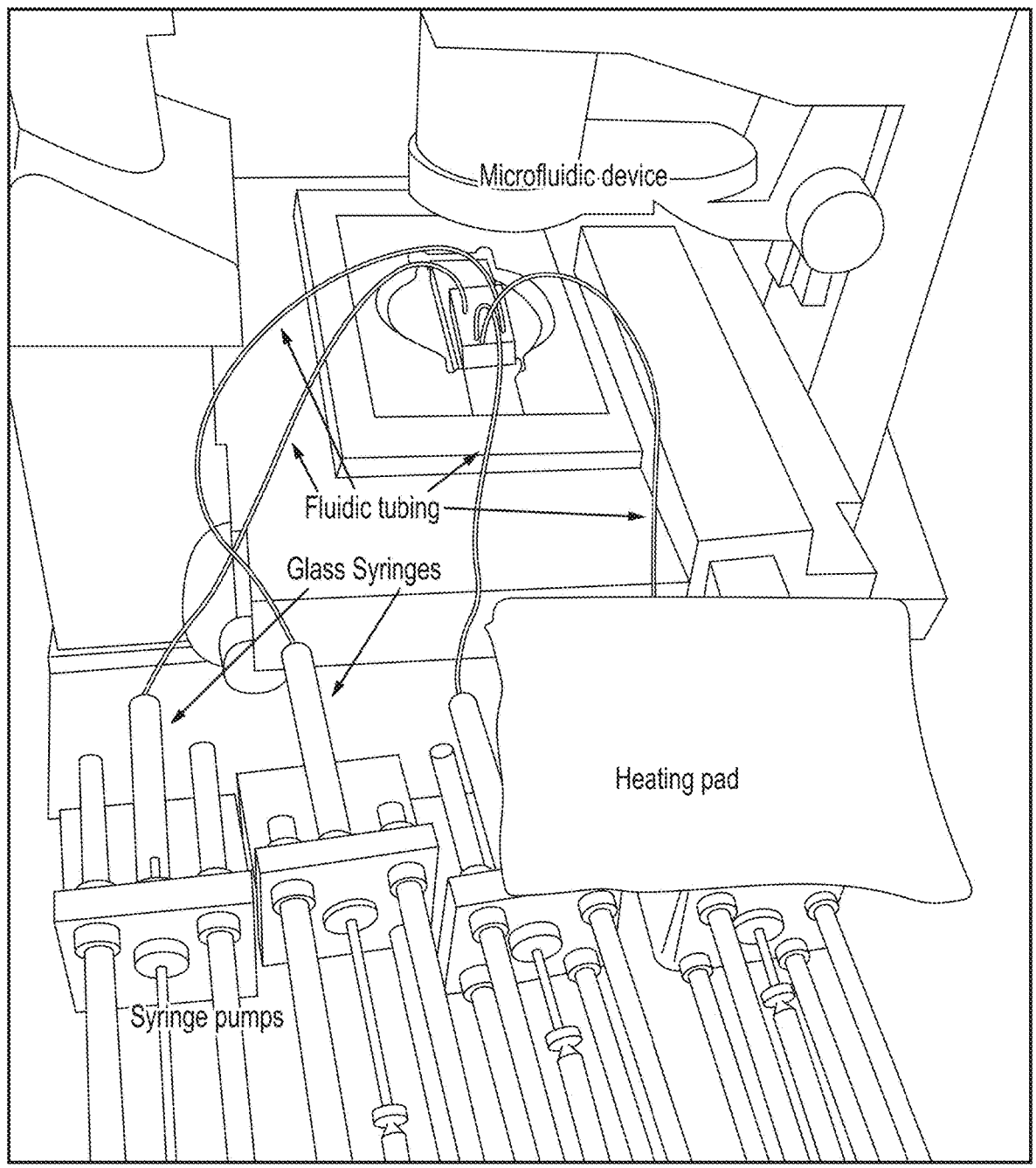
FIGS. 9A-D. Microfluidic set-up for monodisperse agarose bead production. A microfluidic device was mounted on to a light inverted microscope. Syringe pumps were elevated on-top of a laser cut PMMA stand to the level of that of the device. Tubing was used to provide connections between glass syringes and the microfabricated microfluidic system. A microwave heated commercially bought heat pad was placed on top of the agarose syringe to prevent agarose solidification during device operation. A USB connected electrical heating pad was later used to maintain a constant temperature of approximately 40° C.
Figure 9B:
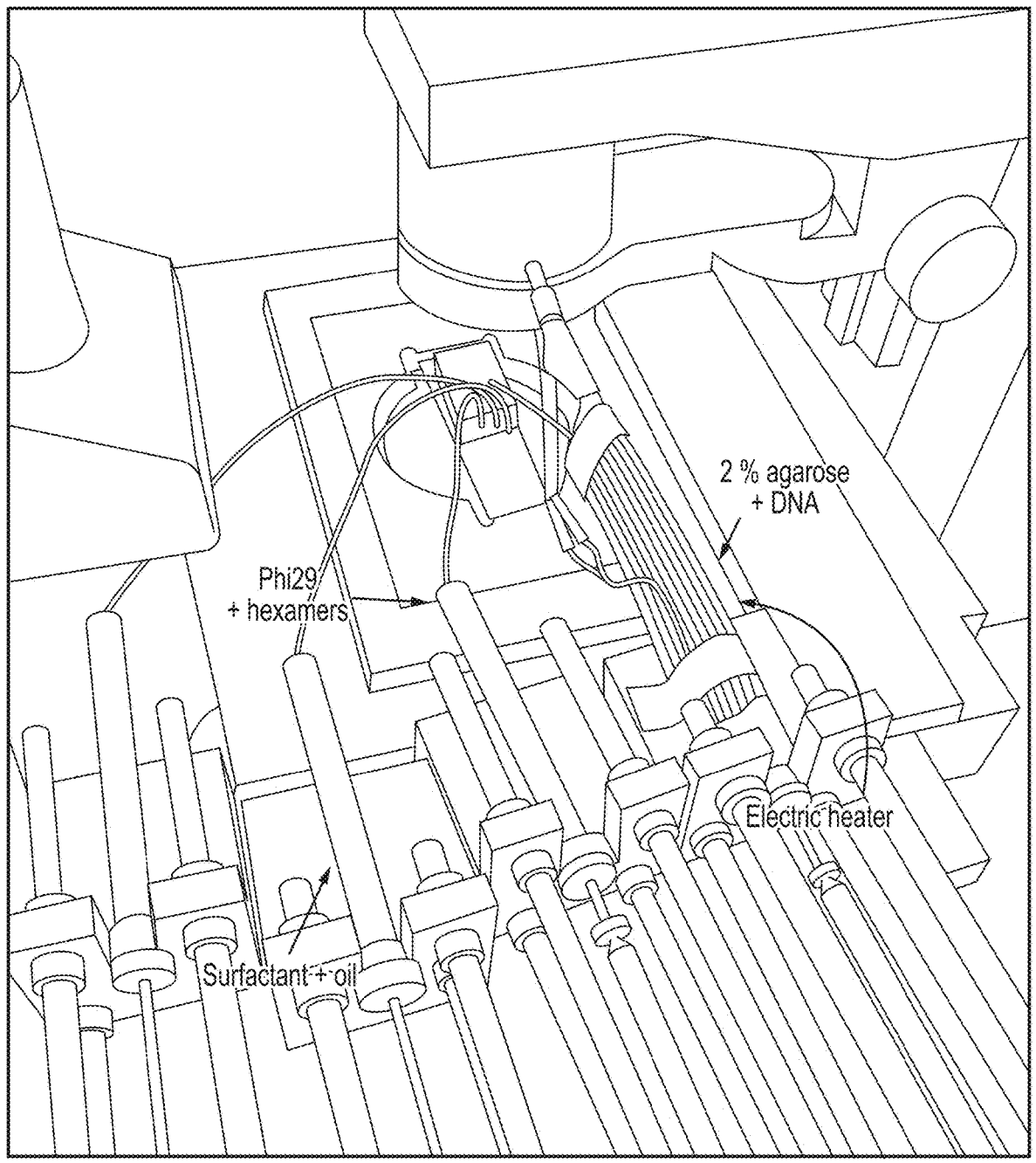
Figure 9C:
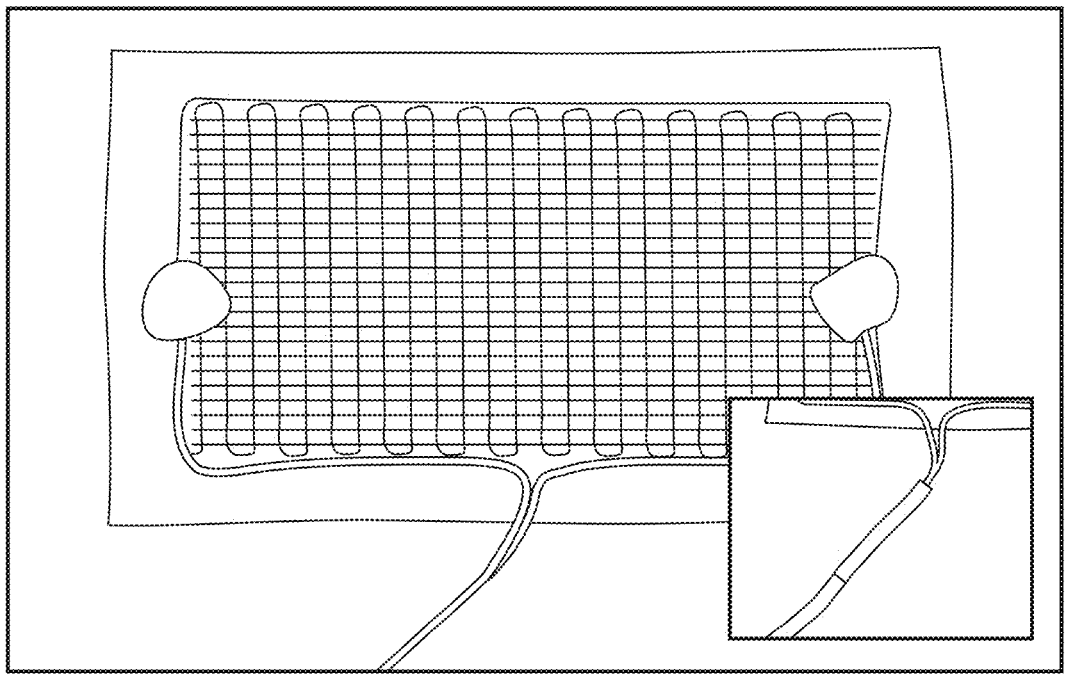
Figure 9D:
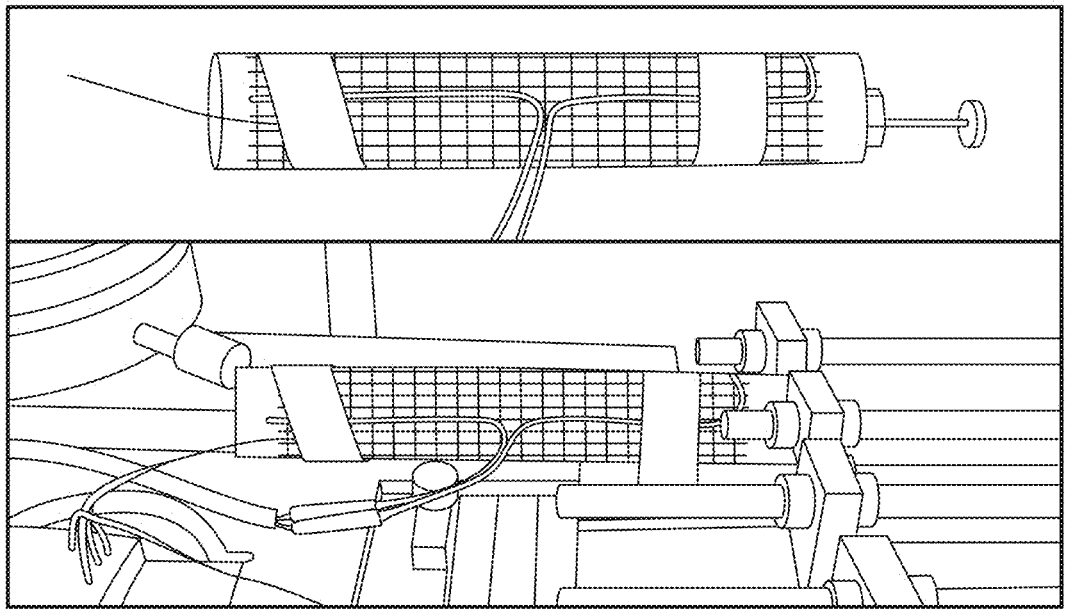

For droplet generation the resulting plasmid library was statistically diluted according to Poisson statistics to ensure the encapsulation of on average ($\lambda$) either (i) 0.1, representing single molecule encapsulation, or (ii) 100 library copies on average (as proof of principle), into 110 fL agarose-in-oil droplets. The resulting plasmid library was injected alongside Phi29 DNA polymerase mediated isothermal amplification reagents into a JUS device and encapsulated using an aqueous flow rate of 10 µl/h for each aqueous phase, and 30 µl/h for oil/surfactant mixture QX200 (droplet generation oil). To generate uniform agarose emulsions droplets, agarose was loaded alongside 1×TAE buffer into a microfluidic device with QX200 oil/surfactant as the continuous phase. To ensure the maintenance of agarose in a liquid state for droplet generation, the agarose containing syringe was preheated with a commercially purchased microwavable heating pack both prior to filling with agarose as well as during device operation (FIG. 9A). Alternatively, a commercially available 5 V DC powered 5×10 cm heating pad (FIG. 9B) was purchased and manually connected to a standard 5 V USB cable to generate a heating element for constant use with the ability to generate a temperature of approximately 40 C during the 10 minutes of operation.

Figure 10A:
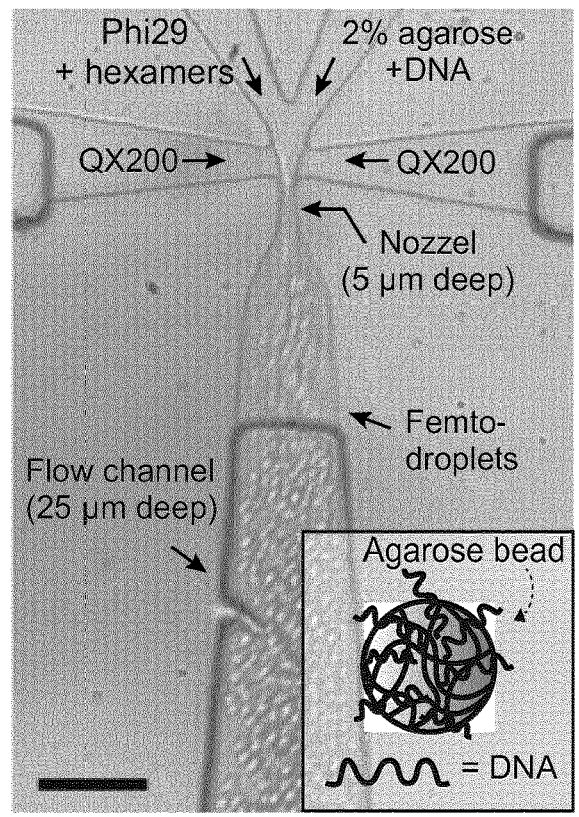
FIGS. 10A-C. Analysis of agarose beads comprising Phi29 DNA amplified plasmid DNA. (A) Process of agarose droplet formation on chip, insert represents an illustration of a solidified agarose bead comprising amplified DNA. (B) Diameter size distribution of four individual agarose bead photographs once broken from emulsion. (C) Brightfield imagery of unwashed agarose beads in 1×TAE buffer; fluorescence imagery of agarose beads incubated with a fluorescent double-stranded DNA-binding dye.
Figure 10B:
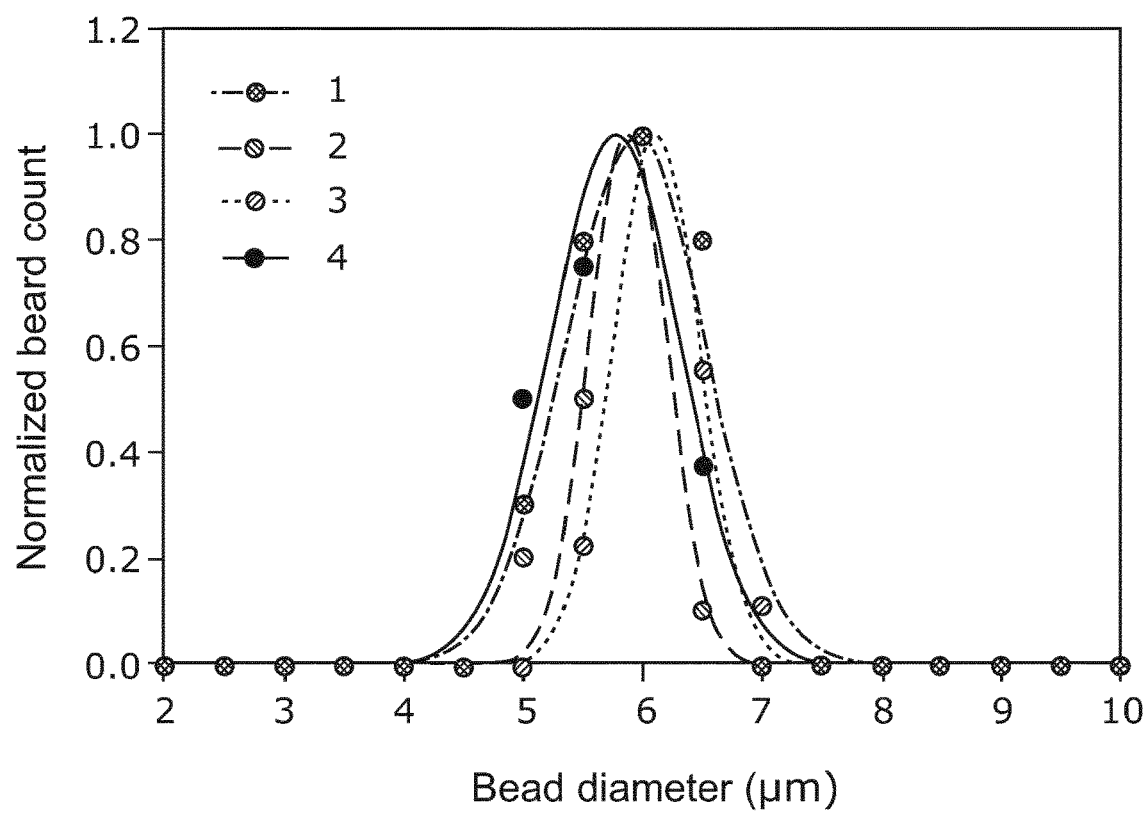
Figure 10C:
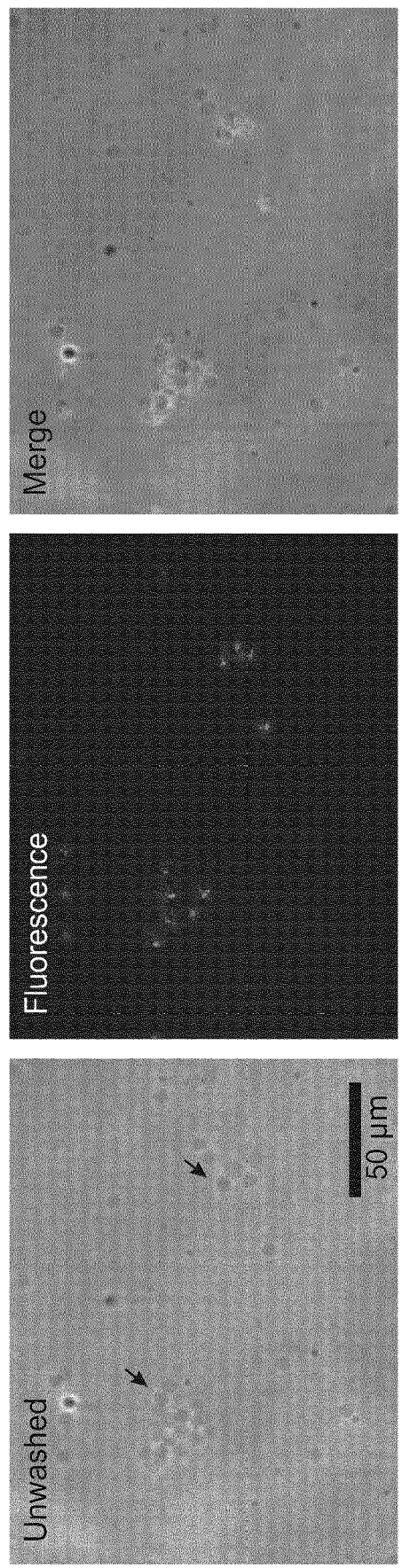
Figure 11A:
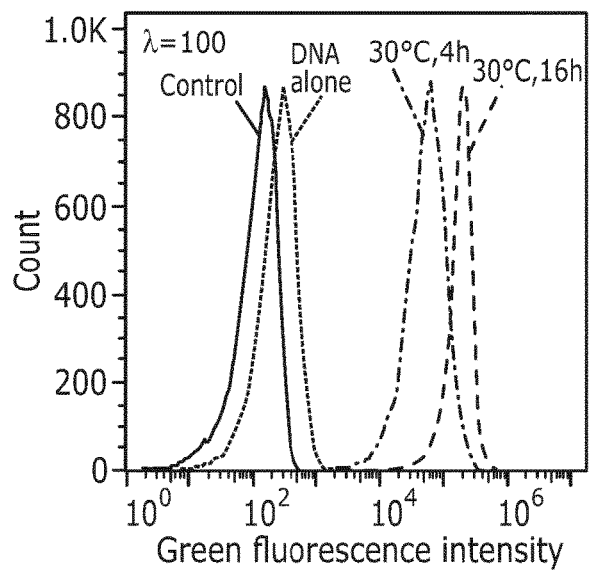
FIGS. 11A-D. Flow cytometric analysis of monodisperse 1% agarose beads comprising Phi29 DNA polymerase amplified plasmid DNA. To permit analysis and visualization, following incubation at 30 C isolated agarose beads are stained with a fluorescent ds-DNA binding. In each condition, the starting DNA solution has been statistically diluted to ensure on average (A) 100, (B) 10, (C) 1 or (D) 0.1 DNA copies (2 value) per droplet according to Poisson statistics.
Figure 11B:
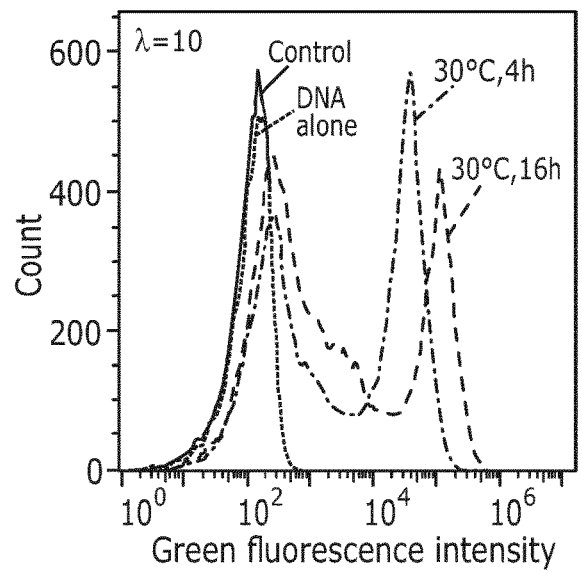
Figure 11C:
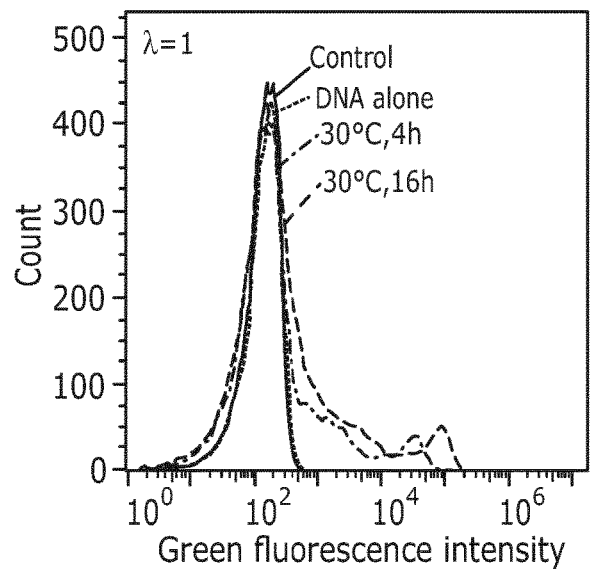
Figure 11D:
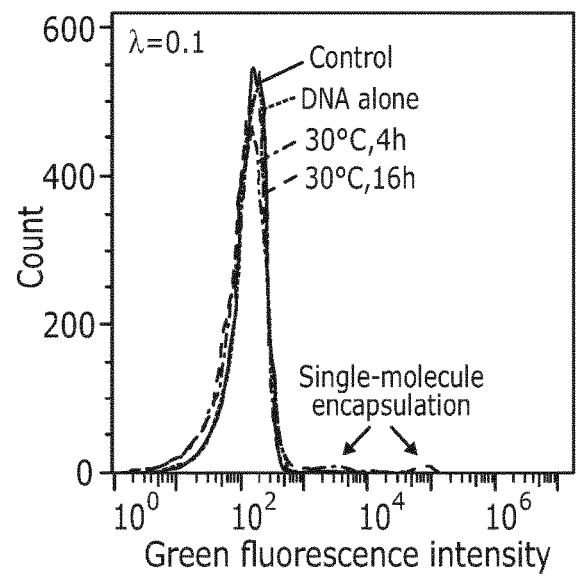

Following collection (FIG. 10A), agarose droplets now comprising DNA with Phi29 DNA polymerase amplification components were incubated at 30 C overnight. Solidification via incubation on ice and bead extraction using PFO were performed to isolate the desired agarose bead population. Resultantly, beads were stained using a fluorescent double-stranded DNA binding DNA to permit visualization of the internal DNA (FIG. 10 C).

Figure 13A:
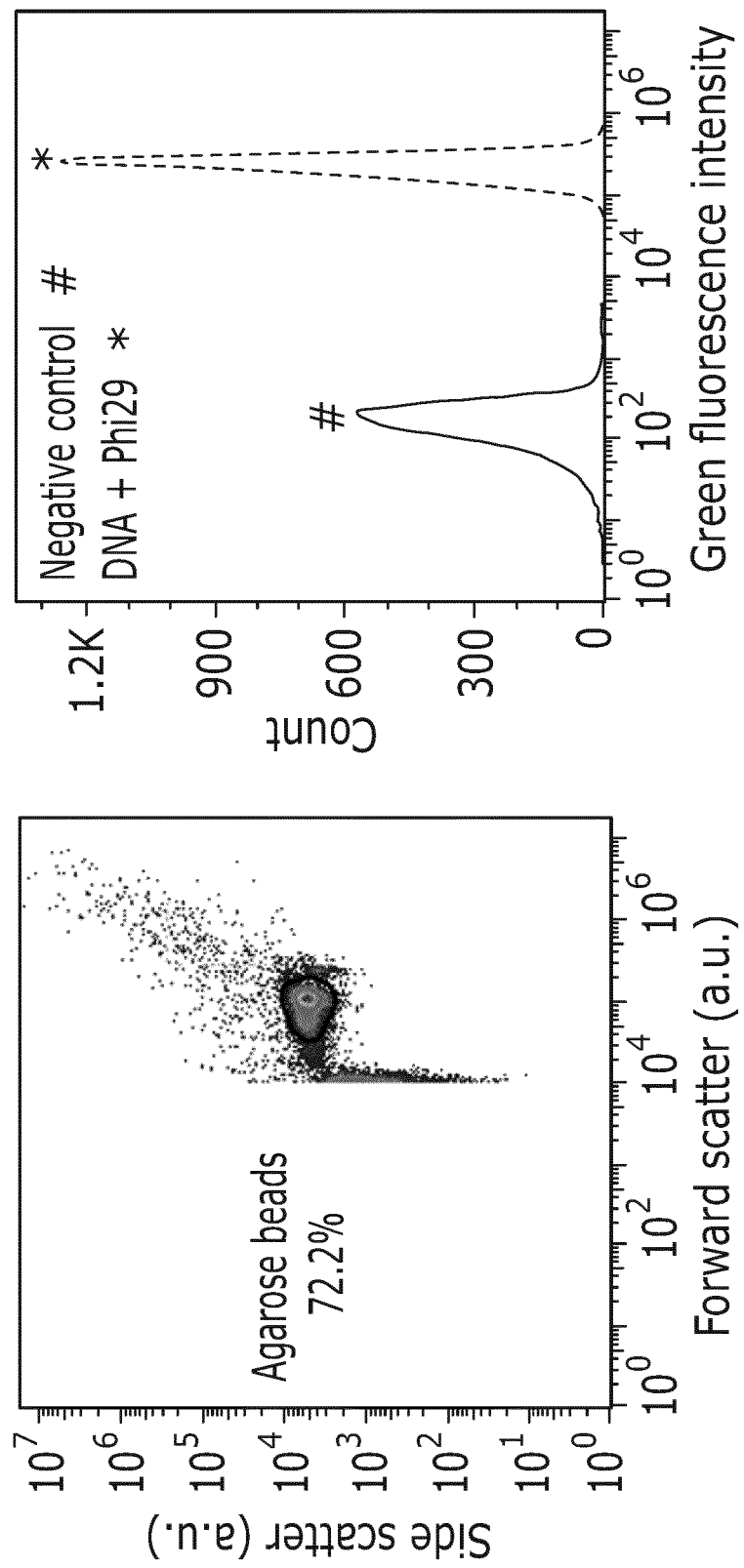
FIGS. 13A-B. IVTT of GFP from Phi29 DNA polymerase pre-amplified SICLOPPS library plasmid DNA in agarose beads. (A) Microfluidically generated agarose beads comprising SICLOPPS plasmid DNA with on average 100 starting DNA copies and Phi29 DNA amplification components were incubated at 30 C for 16 h and analysed using flow cytometry. Once stained with a DNA intercalating dye, a distinct increase in the green fluorescence intensity signal compared to the corresponding negative control is observed, demonstrating successful amplification. (B) Prior to IVTT, solidified DNA enclosed agarose beads were washed via centrifugation at 6,500 rpm to remove the amplification buffer, and injected into a 15×16 µm hydrophobic device along with PURExpress IVTT components. Following incubation at 37 C for 2 h, the IVTT droplets were re-emulsified into a triple emulsion format using a hydrophilic device flow cytometry analysis. Two distinct droplet populations are observed on forward versus side scatter graphs, the higher corresponding to agarose-in-IVTT-in-oil-in-aqueous droplets. Compared to controls in the absence of amplified DNA and IVTT, evident and distinct GFP mediated green fluorescence is observed approximately 10 fold greater than background fluorescence of the IVTT mixture.
Figure 13B:
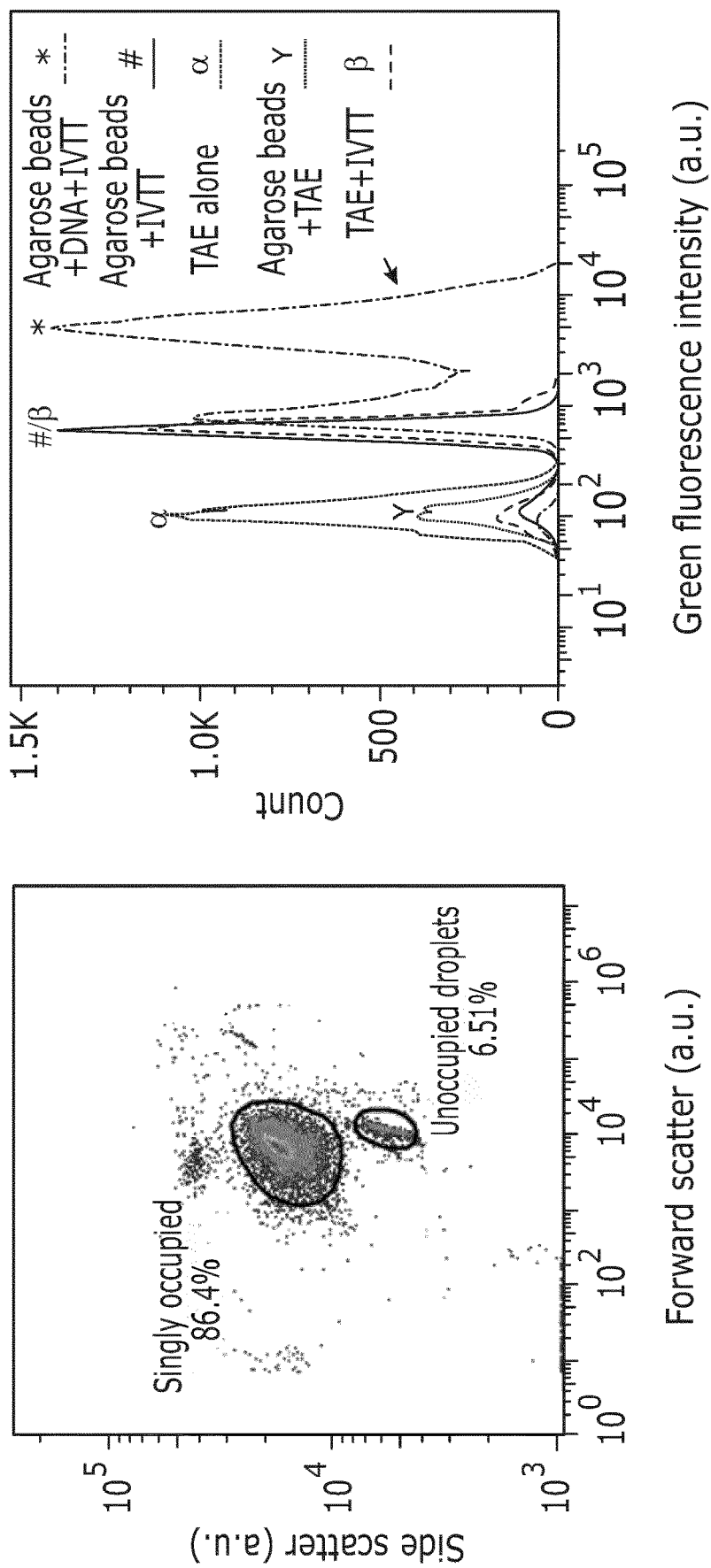
Figure 14:
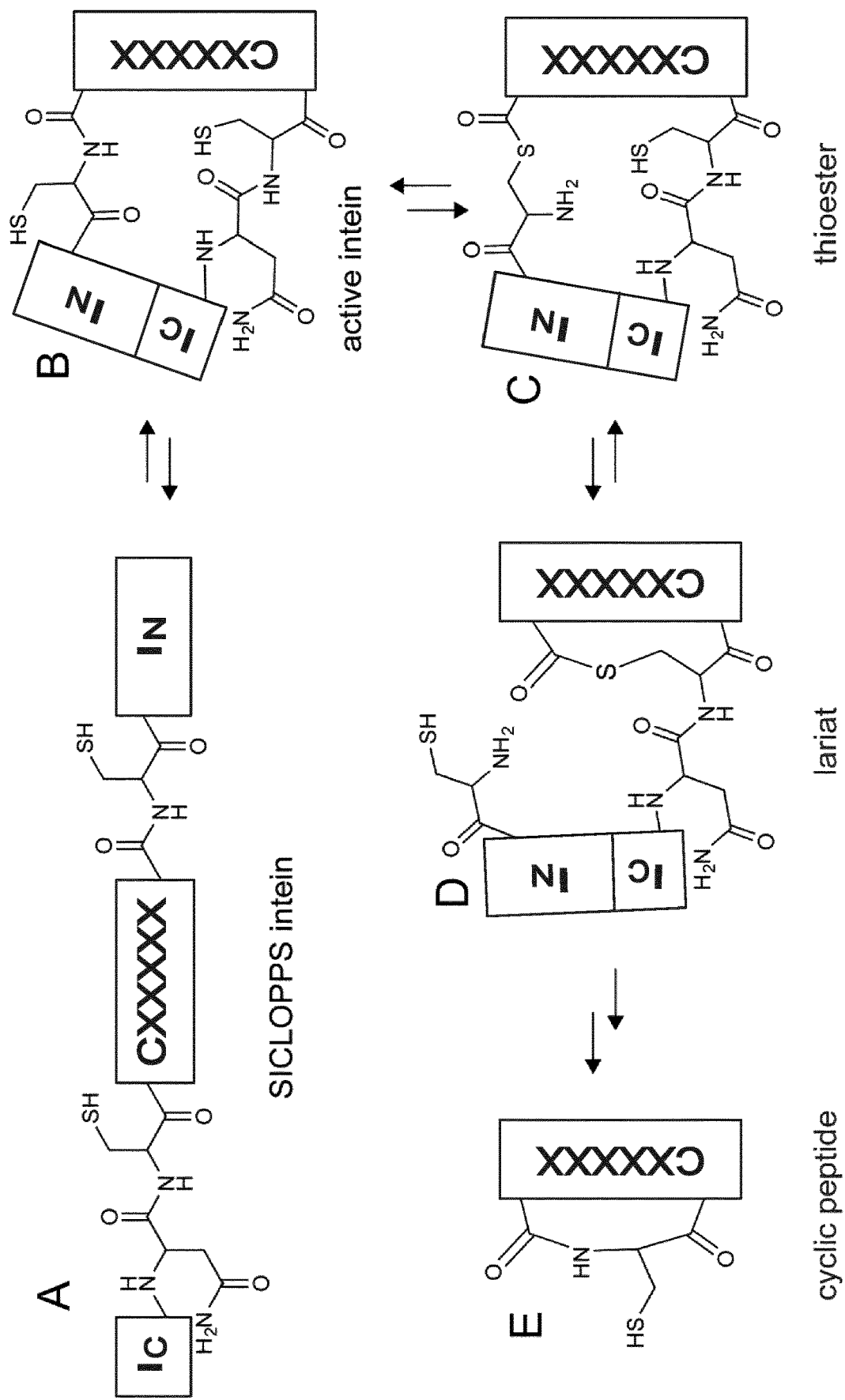
FIG. 14-E. Spontaneous polypeptide cyclisation catalysed by the split intein in a SICLOPPS polypeptide (A). Formation of the active intein from the amino and carboxy-terminal intein fragments (B) stabilizes the ester isomer of an amino acid at the junction between the N-intein and the peptide to be cyclized (C). The heteroatom from the C-intein is poised to attack the ester and generate a cyclic ester intermediate (D). Intein-catalysed aminosuccinimide formation liberates the cyclic peptide (in the lactone form, not shown), which spontaneously rearranges to form the thermodynamically favoured backbone (lactam form) cyclic peptide product (E). One or more of the cysteines depicted may be replaced with threonines, i.e. the thiol groups may be replaced with alcohol (OH) groups. Other heteroatoms may also replace the sulphur atom of the cysteine residues depicted provided this does not prevent formation of the ester intermediates, nucleophilic attack, or backbone rearrangement.

Flow cytometry analysis of stained agarose beads comprising on average 100, 10, 1 or 0.1 starting DNA copies ($\lambda$ value) prior to amplification (FIG. 11), where 0.1 represent single molecule encapsulation, is presented in FIG. 13. Incubation overnight for 16 h (corresponding to approximately 12,000 final DNA copies per droplet) is preferential for generating a greater quantity of DNA when compared to 4 hours incubation. In all cases, distinct Phi29 DNA polymerase mediated DNA amplification is observed in each experimental condition when compared against negative controls comprising DNA alone, or empty (no DNA) agarose beads.

Figure 12:
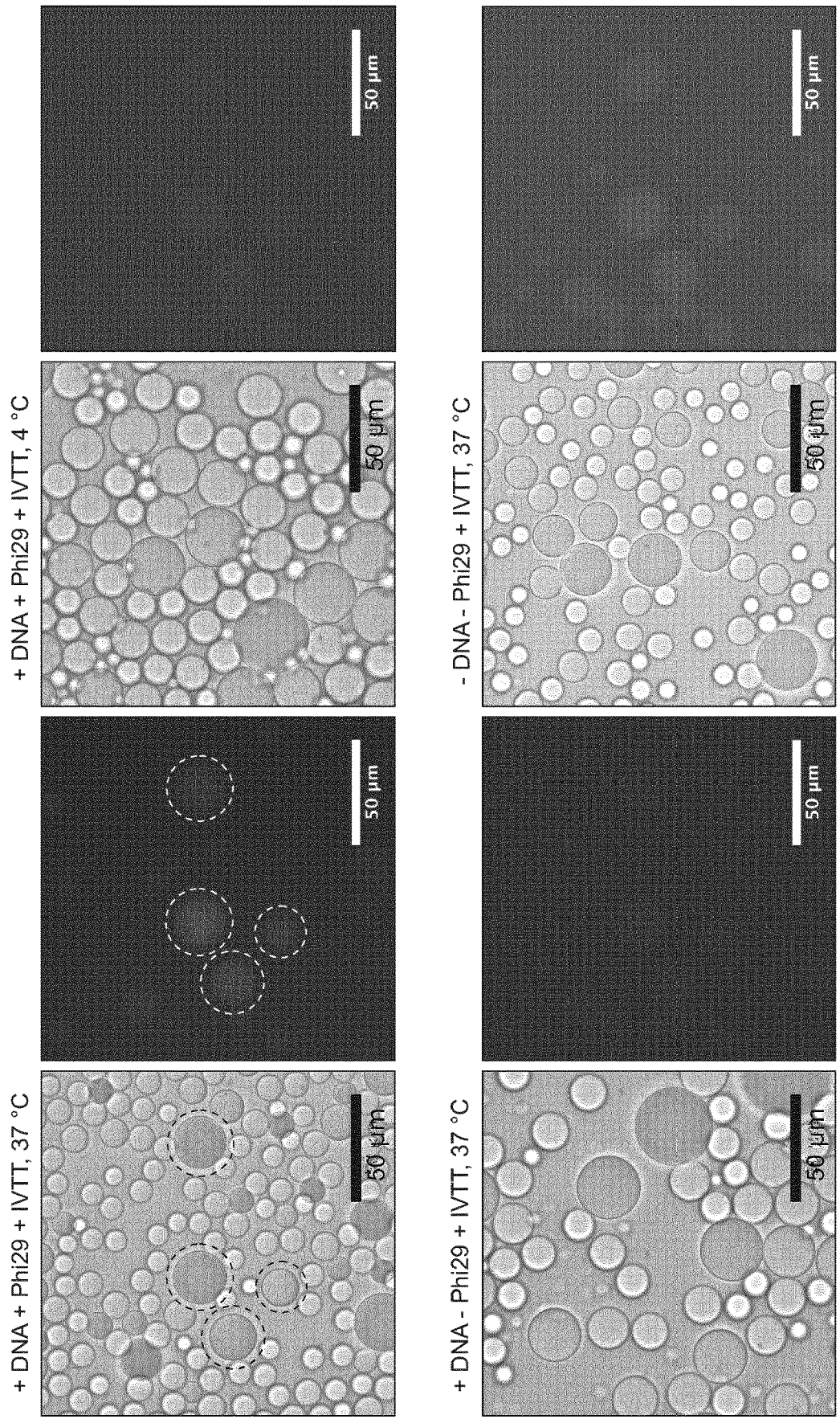
FIG. 12. In vitro protein expression from agarose beads comprising Phi29 pre-amplified SICLOPPS library plasmid DNA in polydisperse bulk emulsions. Following DNA amplification, agarose beads are isolated and washed via centrifugation 3× at 6,500 rpm. Once washed, the beads are re-suspended into a solution comprising the PURExpress IVTT components and QX200 oil/surfactant, and finally vortexed for 10-15 s to yield polydisperse bulk emulsions. The generation of polydisperse droplets, as opposed to monodisperse with a microfluidic device, enables one to quickly determine suitable conditions for the desired biochemical reaction. Accordingly, in the presence of pre-amplification GFP mediated fluorescence from a SICLOPPS plasmid (encoding SICLOPPS inteins and GFP) is clearly visible; in contrast, in the absence of the DNA amplification no GFP fluorescence is observed, therefore highlighting the importance of amplification from single copies for IVTT in drops. Emulsion samples were incubated at 37 C for 2 hours prior to imaging.

Since the buffer system used for DNA amplification is known to be incompatible with droplet based IVTT, agarose beads comprising monoclonal amplified plasmid DNA were solidified and subsequently washed via centrifugation to permit their re-suspension in a solution now compatible with IVTT. To further investigate the compatibility of IVTT using the PURExpress system with our plasmid-containing agarose beads, washed agarose beads were resuspended in an IVTT solution with QX200 oil/surfactant and vortexed to rapidly generate bulk polydisperse droplets, the brightfield and fluorescence photographs for which are presented in FIG. 12. Interestingly, GFP mediated fluorescence is observed from samples comprising Phi29 amplified DNA in agarose beads with in vitro protein expression components, whilst no fluorescence is observed in the absence of amplification. Accordingly, the addition of a pre-amplification step from single-copy DNA encapsulation is fundamental to the successful in vitro mediated protein expression of protein constructs. This demonstrates production of a SICLOPPS library and GFP in these droplets using our dual-expression vector.

To demonstrate the in vitro mediated protein expression of GFP in microfluidically generated monodisperse droplets using the PURExpress system, agarose droplets containing approximately 100 starting plasmid DNA copies was pre-amplification using Phi29 DNA amplification (FIG. 13A) and washed as previously detailed. Agarose beads were subsequently taken up within a glass syringe and injected, along with IVTT components and a 1% tris/tween80 continuous phase, into a hydrophobic 15×16 µm microfluidic device. Following collection, droplets were incubated at 37 C for 2 h before emulsifying via a 15×25 µm hydrophilic device into triple emulsion droplets with an external aqueous phase for flow cytometric analysis. Resultantly, in vitro GFP expression is presented in highly monodisperse microfluidically generated droplets in FIG. 13B. The IVTT PURExpress system itself is observed to display high levels of background fluorescence; nonetheless, distinct GFP mediated fluorescence approximately 10-fold greater than background levels is observed, enabling easy selection of droplets containing cyclic peptides using e.g., fluorescence activated cell sorting (FACS) for the recovery of the desired phenotypic trait. Accordingly, in vitro protein expression via a robust agarose and IVTT platform in the absence of complicated droplet merging procedures in microfluidic droplets is presented.

Example 5: Formation and Sorting of a Cyclic Peptide

We have demonstrated by mass spectrometry the formation of a cyclic peptide via intein splicing within an emulsion. The cyclic peptide continues to be present after FACS sorting of the emulsion droplets.

The vectors of example 3 were used to encode an intein-bounded hexapeptide, CLLFVY (SEQ ID NO: 5). This vector was used to produce cyclic CLLFVY (SEQ ID NO: 5) as follows.

Figure 16:
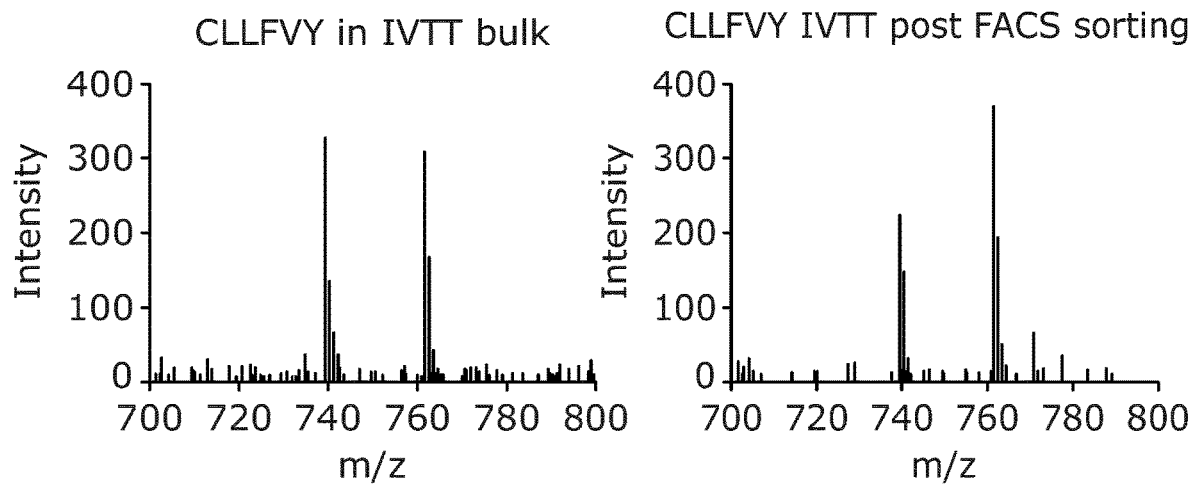
FIG. 16. pDuetNpu encoding the polypeptide CLLFVY (SEQ ID NO: 5) cyclised in vitro. Mass spectrometry of vector CSpDuetNpuHisCLLFVY (SEQ ID NO: 6) following IVTT in bulk format and following FACS sorting. (Left) Standard PURExpress IVTT reaction assembled in the presence of vector CSpDuetNpuHisCLLFVY (SEQ ID NO: 6). (Right) Pre-amplification of vector CSpDuetNpuHisCLLFVY (SEQ ID NO: 6) in agarose beads. Washed agarose beads comprising monoclonally amplified DNA were re-encapsulated together with IVTT to permit CLLFVY (SEQ ID NO: 5) expression, prior to a third emulsification step to yield double emulsion FACS compatible droplets. FACS sorted samples were broken from emulsion and submitted for mass spectrometric analysis. Peaks indicative of cyclo-CLLFVY (SEQ ID NO: 5) are evident in either case.

A standard PURExpress IVTT reaction was assembled in the presence of vector CSpDuetNpuHisCLLFVY (SEQ ID NO: 6). Reactions were incubated at 37° C., 2 h prior to mass spectrometric analysis. The results are shown in FIG. 16, left panel.

In a second experiment, vector CSpDuetNpuHisCLLFVY (SEQ ID NO: 6) was pre-amplified in highly monodisperse ~6 μm 1% agarose beads overnight via the TempliPhi amplification system at 30° C. Following enzyme heat inactivation, beads were broken from emulsion and washed via centrifugation at ~6,000 rpm 3× in diH2O to permit efficient amplification buffer removal (which would inadvertently interfere with subsequent IVTT manipulations). Washed agarose beads comprising monoclonally amplification DNA were then re-encapsulated together with IVTT to permit CLLFVY (SEQ ID NO: 5) expression and incubated at 37° C., 2 h, prior to a third emulsification step to yield double emulsion FACS compatible droplets.

Double emulsion populations exhibiting increased GFP fluorescence above background (MCS2 cloned GFP) were selected for sorting. Sorted samples were broken from emulsion and submitted for mass spectrometric analysis. See FIG. 16, right-hand panel.

Peaks indicative of cyclo-CLLFVY (SEQ ID NO: 5) are evident in either case.

Example 6. In Vitro Expression in Microfluidic Droplets of AB42-GFP Fusion with Cyclo-TAFDR The cyclic peptide TAFDR (SEQ ID NO: 7) is a cyclocpeptide that has been shown to inhibit aggregation of Alzheimer's protein Aβ42 fused to GFP. When GFP is produced as an aggregating fusion, its fluorescence is lost; however, when the aggregation is disrupted by TAFDR (SEQ ID NO: 7), the GFP can fluoresce. See Mathis et al., Nature Biomedical Engineering volume 1, pages 838-852 (2017).

Figure 17:
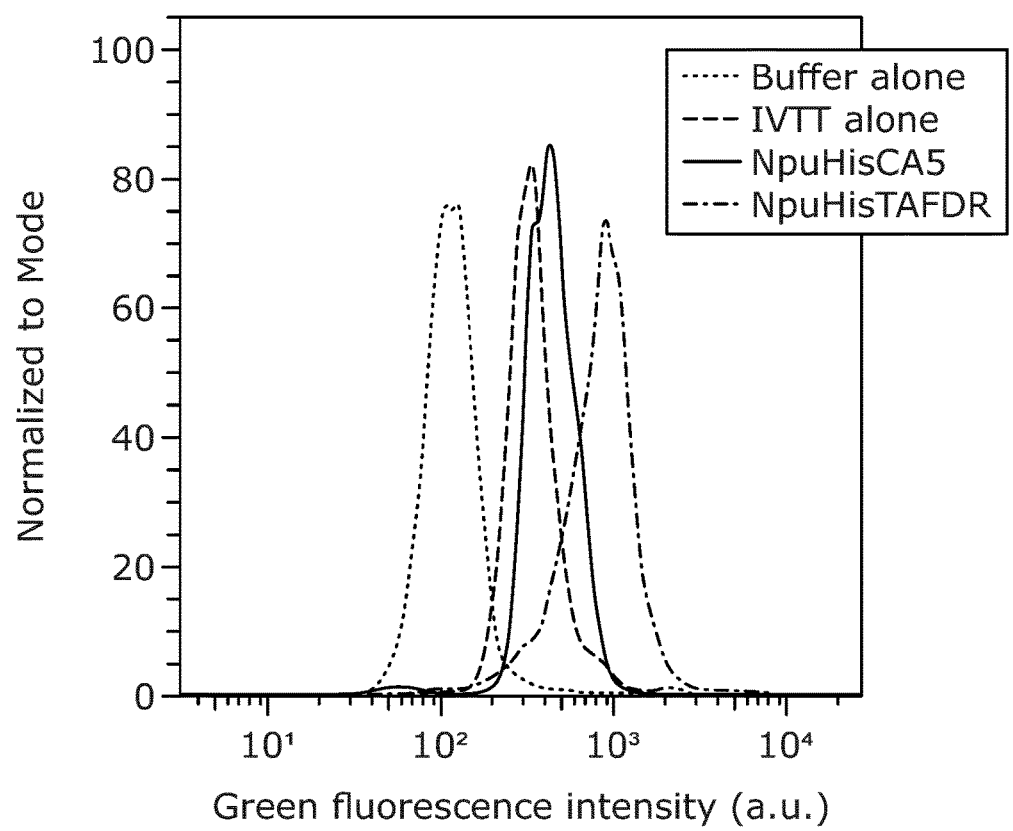
FIG. 17. In vitro expression in microfluidic droplets of AB42-GFP fusion with cyclo-TAFDR (SEQ ID NO: 7) (Matis et al.). Vector CSpDuetNpuHisAB42-GFP was utilised for the cloning of TAFDR (SEQ ID NO: 7) into MCS1. Thereafter, plasmid DNA was encapsulated into agarose droplets alongside isothermal DNA amplification reaction components and incubated overnight. Agarose beads were prepped as previously stated and re-encapsulated together with IVTT. A final emulsification step was performed to yield FACS compatible double emulsions. A negative control vector in the presence of CA5 was likewise constructed to verify cyclo-TAFDR (SEQ ID NO: 7) AB42-GFP aggregation inhibition. A positive shift in green fluorescence upon cyclo-TAFDR (SEQ ID NO: 7) expression was observed relative to buffer alone, IVTT alone, and cyclo-CA5 data.

We have used the Aβ42 aggregation assay to assess the performance of the system of the invention. This assay has previously been combined with a SICLOPPS screen (Mathis et al.), so cyclo-TAFDR (SEQ ID NO: 7) is a validated positive cyclic peptide control. FIG. 17 shows expression of this control peptide in droplets, along with the AB GFP fusion protein, causes a significant increase in fluorescence, associated with disruption of Aβ aggregation.

Vector CSpDuetNpuHisAB42-GFP was utilised for the cloning of TAFDR (SEQ ID NO: 7) into MCS1. Thereafter, plasmid DNA was encapsulated into highly monodisperse 1% agarose droplets alongside isothermal DNA amplification reaction components and incubated overnight at 30° C. Agarose beads were prepped as previously stated and re-encapsulated together with IVTT prior to 2 h incubation at 37° C. A final emulsification step was performed to yield FACS compatible double emulsions. A negative control vector in the presence of CA5 was likewise constructed to verify cyclo-TAFDR (SEQ ID NO: 7) AB42-GFP aggregation inhibition. A positive shift in green fluorescence upon cyclo-TAFDR (SEQ ID NO: 7) expression was observed relative to buffer alone, IVTT alone, and cyclo-CA5 data.

Figure 18B:
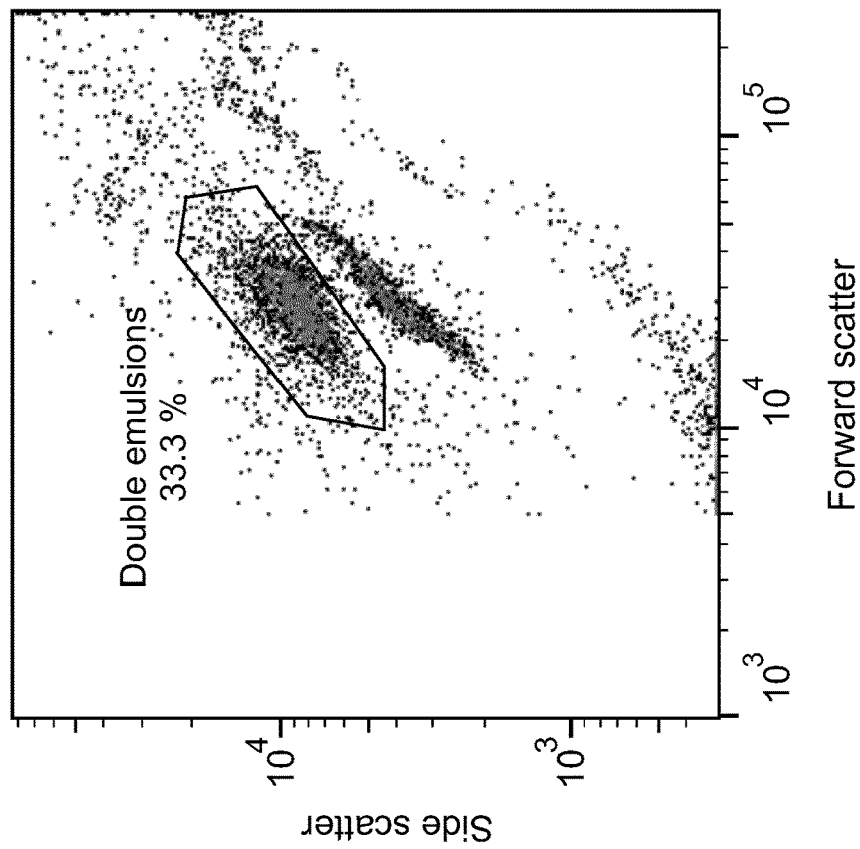
FIGS. 18A-B. In vitro compartmentalisation and FACS screening of a TX4 SICLOPPS library in double emulsion droplets. Plasmid construction of a pETDuet-1 vector comprising NpuHis TX4 in MCS1 and AB42-GFP fusion in MCS2. To permit monoclonal DNA amplification prior to IVTT, plasmid DNA was encapsulated into agarose femodroplets alongside TempliPhi isothermal DNA amplification components. Beads were broken from emulsion, the aqueous phase extracted and washed permit amplification buffer removal. Beads were next encapsulated alongside the PURExpress IVTT system in highly monodisperse droplets prior to incubation at 37° C. for 2 h. Following protein expression, samples were transformed into a double emulsion format (agarose bead-in-IVTT-in-oil-in-water) to permit FACS screening. Double emulsion populations were identified and gated to permit library sorts (B). Fluorescence readings above IVTT background alone were gated from double emulsion populations and sorted on FL1-H (GFP, A). Percentage +ve (potential positive candidate peptides) and –ve gated particles are indicated for the TX4 library sample only (dotted line).
Figure 18A:
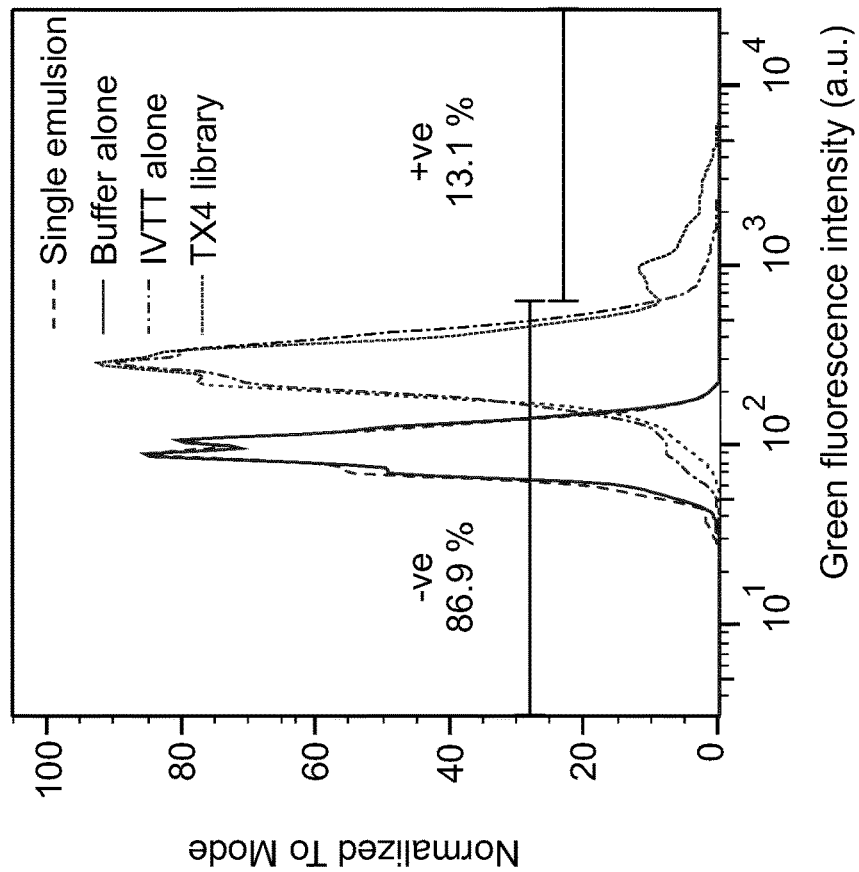

Example 7. In Vitro Compartmentalisation and FACS Screening of a TX4 SICLOPPS Library in Double Emulsion Droplets Using the method of example 6, a full screen has been carried out with a TX4 library. FIG. 18 shows a clear pool of potentially active compounds (region labelled +ve 13.1%).

Similarly to Example 6, plasmid construction of a pET-Duet-1 vector comprising NpuHis TX4 in MCS1 and AB42-GFP fusion in MCS2. To permit monoclonal DNA amplification prior to IVTT, plasmid DNA was encapsulated into highly monodisperse ~6 μm agarose femodroplets (1% agarose) alongside TempliPhi isothermal DNA amplification components. Samples were incubated overnight (16 h) to permit maximal amplification at 30° C. Phi29 DNA polymerase was heat inactivated at 65° C., 10 mins. Beads were incubated on ice to facilitate conversion to the gel phase and permit trapping of isothermally amplified DNA products. Beads were broken from emulsion, the aqueous phase extracted and washed 3× in diH2O (6,000 rpm) to permit amplification buffer removal. Beads were next encapsulated alongside the PURExpress IVTT system in highly monodisperse droplets prior to incubation at 37° C. for 2 h. Following protein expression, samples were transformed into a double emulsion format (agarose bead-in-IVTT-in-oil-in-water) to permit FACS screening. Double emulsion populations were identified and gated to permit library sorts (B). Fluorescence readings above IVTT background alone were gated from double emulsion populations and sorted on FL1-H (GFP, A). Percentage +ve (potential positive candidate peptides) and −ve gated particles are indicated for the TX4 library sample only (dotted line).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for co-compartmentalizing cyclic polypeptides in a hydrophilic microfluidic device, the method comprising in order:

(a) forming a plurality of multicompartment systems comprising a plurality of monodisperse water-in-oil-in-water (w/o/w) emulsion droplets on the hydrophilic microfluidic device, wherein each of the plurality of multicompartment systems comprises:

(i) a first compartment comprising an aqueous droplet, comprising an in vitro transcription and translation (IVTT) system, detectable fluorescent reporters, and a gel forming agent comprising an ultra-low gelling temperature agarose, wherein the an ultra-low gelling temperature agarose is fluid at 37° C. and has a transition gelling point between 8-17° C., wherein the gel forming agent comprises a polynucleotide sequence that encodes a cyclic polypeptide, and wherein the polynucleotide sequence comprises, from 5' to 3', a sequence encoding an N-terminal intein fragment,
a sequence encoding the polypeptide that is to be cyclized, and
a sequence encoding a C-terminal intein fragment,
wherein detectable fluorescent reporters are selected from the group consisting of fluorescein, fluorescent proteins and fluorophores wherein the IVTT system comprises a transfer RNA (tRNA) charged with natural or non-natural amino acids, an RNA polymerase, a ribosome, nucleotide phosphates, and translation factors;
(ii) a second compartment comprising a fluorinated oil surrounding the first compartment, such that the first compartment and the second compartment form a plurality of monodisperse water-in-oil (w/o) emulsion droplets, and;
(iii) a third compartment comprising a discontinuous external aqueous phase comprising a surfactant, wherein the discontinuous external aqueous phase surrounds each of the plurality of monodisperse water-in-oil emulsion droplets to form a plurality of monodisperse water-in-oil-in-water emulsion droplets, wherein prior to formation of the third compartment, the method comprises,
(b) amplifying the polynucleotide sequence that encodes a cyclic polypeptide within each first compartment to produce a plurality of amplicons, each first compartments comprising a plurality polynucleotide sequences encoding the polypeptides that are to be cyclized such that during amplification an external source of heat is constantly and evenly applied to a reaction vessel and/or applied to a reaction container in which amplification is being carried out, wherein the constant and even application of heat to the reaction vessel and/or to the reaction container maintains the gel forming agent in a liquid phase for amplification of the polynucleotide sequence prior to in vitro polypeptide expression, such that more than three (3) million monodisperse w/o emulsion droplets are generated;
(c) following amplification, solidifying the gel forming agent by lowering the temperature of the reaction vessel and/or the reaction container to form a gel matrix that traps the plurality of amplicons in the gel matrix of the monodisperse w/o emulsion droplet, and
(d) in vitro expressing a plurality of polypeptides from the plurality of amplicons within the gel matrix formed in (c) to produce a plurality of expressed polypeptides, such that the plurality of amplicons encoding the plurality of polypeptides and the expressed polypeptides are contained in the gel matrix of the first compartment; wherein the plurality of expressed polypeptides in each of the plurality of first compartments self-cyclize to form a plurality of cyclic polypeptides within each of the plurality of monodisperse w/o emulsion droplets.

2. The method according to claim 1, wherein the gel matrix is a gel bead.

3. The method according to claim 2, wherein the plurality of w/o/w emulsion droplets are disrupted to release the gel bead from each of the plurality of multicompartment systems.

4. The method according to claim 2, wherein each gel bead ranges in size from about 6-7 micrometers (μm) in diameter.

5. The method according to claim 1, wherein the ultra-low gelling temperature agarose comprises 1% agarose.

6. The method according to claim 1, wherein each aqueous droplet has a volume of about 5-50 femtoliters.

7. The method according to claim 1, wherein the constant and even application of heat applied to the reaction vessel and/or applied to the reaction container is maintained at a temperature of about 40° C.

8. The method according to claim 2, wherein the gel beads can be sorted in a high-throughput manner comprising a method selected from the group consisting of fluorescence activated cell sorting (FACS) and fluorescence activated droplet sorting (FADS).

9. The method of claim 2, further comprising screening the plurality of cyclic polypeptides produced in claim 1 for an ability to inhibit a target enzyme in an assay selected from the group consisting of a colorimetric assay or fluorometric assay.

10. The method of claim 2, further comprising screening the plurality of cyclic polypeptides produced in claim 1 in an assay selected from the group consisting of a functional assay, an affinity assay, an inhibition assay, phenotypic assay, and a reporter assay.

11. The method according to claim 1, wherein each of the plurality of monodisperse water-in-oil emulsion droplets is a femtoliter-sized droplet.

* * * * *

SEQUENCE LISTING

```
<160> NUMBER OF SEQ ID NOS: 7

<210> SEQ ID NO 1
<211> LENGTH: 170
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: misc_feature
<222> LOCATION: (55)..(55)
<223> OTHER INFORMATION: Xaa can be any naturally occurring amino acid

<400> SEQUENCE: 1

His His His His His His Gly Glu Asn Leu Tyr Phe Lys Leu Gln Ala
1               5                   10                  15

Met Gly Met Ile Lys Ile Ala Thr Arg Lys Tyr Leu Gly Lys Gln Asn
            20                  25                  30

Val Tyr Asp Ile Gly Val Glu Arg Tyr His Asn Phe Ala Leu Lys Asn
        35                  40                  45

Gly Phe Ile Ala Ser Asn Xaa Cys Leu Ser Tyr Asp Thr Glu Ile Leu
    50                  55                  60

Thr Val Glu Tyr Gly Ile Leu Pro Ile Gly Lys Ile Val Glu Lys Arg
65                  70                  75                  80

Ile Glu Cys Thr Val Tyr Ser Val Asp Asn Asn Gly Asn Ile Tyr Thr
                85                  90                  95

Gln Pro Val Ala Gln Trp His Asp Arg Gly Glu Gln Glu Val Phe Glu
            100                 105                 110

Tyr Cys Leu Glu Asp Gly Cys Leu Ile Arg Ala Thr Lys Asp His Lys
        115                 120                 125

Phe Met Thr Val Asp Gly Gln Met Met Pro Ile Asp Glu Ile Phe Glu
    130                 135                 140

Arg Glu Leu Asp Leu Met Arg Val Asp Asn Leu Pro Asn Gly Thr Ala
145                 150                 155                 160

Ala Asn Asp Glu Asn Tyr Ala Leu Ala Ala
                165                 170

<210> SEQ ID NO 2
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 2

His His His His His His
1               5

<210> SEQ ID NO 3
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 3

Gly Glu Asn Leu Tyr Phe Lys Leu Gln Ala Met Gly Met Ile Lys Ile
1               5                   10                  15

Ala Thr Arg Lys Tyr Leu Gly Lys Gln Asn Val Tyr Asp Ile Gly Val
            20                  25                  30

Glu Arg Tyr His Asn Phe Ala Leu Lys Asn Gly Phe Ile Ala Ser Asn
        35                  40                  45

<210> SEQ ID NO 4
<211> LENGTH: 115
<212> TYPE: PRT
<213> ORGANISM: Artificial sequence
<220> FEATURE:
<223> OTHER INFORMATION: Synthetic polypeptide
```

```
<400> SEQUENCE: 4

Cys Leu Ser Tyr Asp Thr Glu Ile Leu Thr Val Glu Tyr Gly Ile Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Cys
        50                  55                  60

Leu Ile Arg Ala Thr Lys Asp His Lys Phe Met Thr Val Asp Gly Gln
65                  70                  75                  80

Met Met Pro Ile Asp Glu Ile Phe Glu Arg Glu Leu Asp Leu Met Arg
                85                  90                  95

Val Asp Asn Leu Pro Asn Gly Thr Ala Ala Asn Asp Glu Asn Tyr Ala
                100                 105                 110

Leu Ala Ala
        115

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Cys Leu Leu Phe Val Tyr
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic vector

<400> SEQUENCE: 6

His Cys Leu Leu Phe Val Tyr
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 7

Thr Ala Phe Asp Arg
1               5
```